(12) United States Patent
Zuchner et al.

(10) Patent No.: US 12,083,168 B2
(45) Date of Patent: Sep. 10, 2024

(54) TREATMENT AND DETECTION OF INHERITED NEUROPATHIES AND ASSOCIATED DISORDERS

(71) Applicants: University of Miami, Miami, FL (US); University of Rochester, Rochester, NY (US); UCL Business LTD, London (GB)

(72) Inventors: Stephan L. Zuchner, Miami, FL (US); Adriana Rebelo, Miami, FL (US); Andrea Cortese, London (GB); Rong Grace Zhai, Miami, FL (US); David N. Herrmann, Rochester, NY (US)

(73) Assignees: University of Miami, Miami, FL (US); University of Rochester, Rochester, NY (US); UCL Business LTD, London (GB)

(*) Notice: Subject to any disclaimer, the term of this patent is extended or adjusted under 35 U.S.C. 154(b) by 0 days.

(21) Appl. No.: 17/719,580

(22) Filed: Apr. 13, 2022

(65) Prior Publication Data

US 2022/0249624 A1 Aug. 11, 2022
US 2023/0293642 A9 Sep. 21, 2023

Related U.S. Application Data

(63) Continuation of application No. 17/517,227, filed on Nov. 2, 2021, now abandoned, which is a continuation of application No. PCT/US2020/031708, filed on May 6, 2020.

(60) Provisional application No. 62/987,151, filed on Mar. 9, 2020, provisional application No. 62/844,370, filed on May 7, 2019.

(51) Int. Cl.
| | |
|---|---|
| A61K 38/44 | (2006.01) |
| A61K 31/198 | (2006.01) |
| A61K 31/352 | (2006.01) |
| A61K 31/4184 | (2006.01) |
| A61K 31/4188 | (2006.01) |
| A61K 31/426 | (2006.01) |
| A61K 31/428 | (2006.01) |
| A61K 31/473 | (2006.01) |
| A61K 31/499 | (2006.01) |
| A61K 31/502 | (2006.01) |
| A61K 31/517 | (2006.01) |
| A61K 31/7105 | (2006.01) |
| A61K 38/46 | (2006.01) |
| A61K 48/00 | (2006.01) |
| A61P 25/28 | (2006.01) |
| C12N 9/04 | (2006.01) |
| C12N 15/113 | (2010.01) |
| C12N 15/86 | (2006.01) |
| C12Q 1/6883 | (2018.01) |
| G01N 33/66 | (2006.01) |

(52) U.S. Cl.
CPC .......... *A61K 38/443* (2013.01); *A61K 31/198* (2013.01); *A61K 31/352* (2013.01); *A61K 31/4184* (2013.01); *A61K 31/4188* (2013.01); *A61K 31/426* (2013.01); *A61K 31/428* (2013.01); *A61K 31/473* (2013.01); *A61K 31/499* (2013.01); *A61K 31/502* (2013.01); *A61K 31/517* (2013.01); *A61K 31/7105* (2013.01); *A61K 38/465* (2013.01); *A61K 48/005* (2013.01); *A61P 25/28* (2018.01); *C12N 9/0006* (2013.01); *C12N 15/1137* (2013.01); *C12N 15/86* (2013.01); *C12Q 1/6883* (2013.01); *C12Y 101/01014* (2013.01); *G01N 33/66* (2013.01); *C12N 2310/11* (2013.01); *C12N 2750/14143* (2013.01); *C12Q 2600/156* (2013.01)

(58) Field of Classification Search
CPC ...... A61P 25/28; A61K 38/443; C12N 15/111
USPC ..................... 435/6.1, 91.1, 91.31, 455, 458; 514/44 A, 44 R; 536/23.1, 24.5
See application file for complete search history.

(56) References Cited

U.S. PATENT DOCUMENTS

| | | | |
|---|---|---|---|
| 4,868,301 A | 9/1989 | Mylari et al. | |
| 4,939,140 A | 7/1990 | Larson et al. | |
| 4,954,629 A | 9/1990 | Mylari et al. | |
| 4,996,204 A | 2/1991 | Mylari et al. | |
| 5,155,259 A | 10/1992 | Suzuki et al. | |
| 5,304,557 A | 4/1994 | Mylari | |
| 5,677,342 A | 10/1997 | Malamas et al. | |
| 5,728,704 A | 3/1998 | Mylari et al. | |
| 6,159,976 A | 12/2000 | Lambert et al. | |
| 6,544,756 B1 | 4/2003 | Uchida et al. | |
| 6,570,013 B2 | 5/2003 | Mylari | |
| 6,579,879 B2 | 6/2003 | Mylari | |
| 6,696,407 B1 | 2/2004 | Longo et al. | |
| 6,849,629 B2 | 2/2005 | Mylari | |
| 6,916,824 B1 | 7/2005 | Hua et al. | |
| 7,572,910 B2 | 8/2009 | Mylari | |
| 8,916,563 B2 | 12/2014 | Wasmuth et al. | |

(Continued)

FOREIGN PATENT DOCUMENTS

| | | | |
|---|---|---|---|
| CA | 1299178 | 4/1992 | |
| CA | 2366858 | * 12/2000 | ........... A61K 31/505 |

(Continued)

OTHER PUBLICATIONS

U.S. Appl. No. 17/517,227, filed 2012.*

(Continued)

*Primary Examiner* — Jane J Zara
(74) *Attorney, Agent, or Firm* — Hogan Lovells US LLP

(57) ABSTRACT

The present disclosure relates to methods of detecting and treating inherited neuropathy.

14 Claims, 35 Drawing Sheets

Specification includes a Sequence Listing.

(56) References Cited

U.S. PATENT DOCUMENTS

| | | | |
|---|---|---|---|
| 9,650,383 B2 | 5/2017 | Wasmuth et al. | |
| 9,921,221 B2 * | 3/2018 | King | A61K 45/06 |
| 10,052,324 B2 | 8/2018 | Wasmuth et al. | |
| 10,150,779 B2 | 12/2018 | Wasmuth et al. | |
| 10,639,306 B2 | 5/2020 | Wasmuth et al. | |
| 10,647,726 B2 | 5/2020 | Wasmuth et al. | |
| 10,870,658 B2 | 12/2020 | Wasmuth et al. | |
| 2002/0068740 A1 | 6/2002 | Mylari | |
| 2006/0293265 A1 | 12/2006 | Srivastava et al. | |
| 2006/0293371 A1 | 12/2006 | Kamitama | |
| 2007/0060533 A1 | 3/2007 | Yoshikawa et al. | |
| 2010/0215726 A1 | 8/2010 | Roth | |
| 2011/0092566 A1 | 4/2011 | Srivastava et al. | |
| 2013/0029983 A1 | 1/2013 | Ballatore et al. | |
| 2013/0225592 A1 | 8/2013 | Wasmuth et al. | |
| 2014/0113380 A1 | 4/2014 | Lawrence et al. | |
| 2015/0018240 A1 | 1/2015 | Jackson et al. | |
| 2015/0072989 A1 | 3/2015 | Wasmuth et al. | |
| 2015/0079104 A1 | 3/2015 | Zhou et al. | |
| 2015/0079105 A1 | 3/2015 | Chambers et al. | |
| 2016/0029983 A1 | 2/2016 | Verna et al. | |
| 2017/0216291 A1 | 8/2017 | Wasmuth et al. | |
| 2017/0216292 A1 | 8/2017 | Wasmuth et al. | |
| 2017/0319584 A1 | 11/2017 | Wasmuth et al. | |
| 2017/0362237 A1 | 12/2017 | Mylari | |
| 2018/0085437 A1 | 3/2018 | Fan et al. | |
| 2018/0209997 A1 | 7/2018 | Pharnext | |
| 2018/0237451 A1 | 8/2018 | Wasmuth et al. | |
| 2018/0271865 A1 | 9/2018 | Wasmuth et al. | |
| 2018/0312828 A1 | 11/2018 | Liu et al. | |
| 2019/0201400 A1 | 7/2019 | Wasmuth et al. | |
| 2020/0028345 A1 | 1/2020 | Roy et al. | |
| 2020/0131203 A1 | 4/2020 | Shendelman | |
| 2020/0230139 A1 | 7/2020 | Shendelman | |
| 2020/0268755 A1 | 8/2020 | Wasmuth et al. | |
| 2020/0283451 A1 | 9/2020 | Wasmuth et al. | |
| 2020/0289512 A1 | 9/2020 | Wasmuth et al. | |
| 2021/0284652 A1 | 9/2021 | Wasmuth et al. | |
| 2022/0017535 A1 | 1/2022 | Wasmuth | |
| 2022/0071880 A1 | 3/2022 | Shendelman | |
| 2022/0125890 A1 | 4/2022 | Zuchner et al. | |
| 2022/0226323 A1 | 7/2022 | Perfetti et al. | |
| 2022/0249624 A1 * | 8/2022 | Zuchner | A61K 38/443 |
| 2023/0058134 A1 | 2/2023 | Shendelman | |
| 2023/0121312 A1 | 4/2023 | Shendelman | |

FOREIGN PATENT DOCUMENTS

| | | | |
|---|---|---|---|
| CN | 101143868 | 3/2008 | |
| CN | 102512407 | 6/2012 | |
| EP | 0189272 | 7/1986 | |
| EP | 0256629 | 2/1988 | |
| EP | 0325375 | 7/1989 | |
| EP | 0397350 | 11/1990 | |
| EP | 0401981 | 12/1990 | |
| EP | 0436307 | 7/1991 | |
| EP | 0222576 | 3/1992 | |
| EP | 2065038 | 3/2009 | |
| EP | 3597650 | 1/2020 | |
| EP | 3757107 | 12/2020 | |
| ES | 2639019 T3 * | 10/2017 | A61K 31/14 |
| FR | 2647676 | 12/1990 | |
| JP | S62-114988 | 5/1987 | |
| JP | 2003-155274 | 5/2003 | |
| WO | 1989005791 A1 | 6/1989 | |
| WO | 1989-06651 | 7/1989 | |
| WO | 1991-09019 | 6/1991 | |
| WO | 1995026347 A1 | 10/1995 | |
| WO | 1999-050268 | 10/1997 | |
| WO | 1998042324 A2 | 10/1998 | |
| WO | 1999-15529 | 4/1999 | |
| WO | WO-0059510 A1 * | 10/2000 | C04B 35/632 |
| WO | 2002-079198 | 10/2002 | |
| WO | 2003-061660 | 7/2003 | |
| WO | 2008-002678 | 3/2008 | |
| WO | 2009068668 A1 | 6/2009 | |
| WO | 2012009553 A1 | 1/2012 | |
| WO | 2014113380 | 7/2014 | |
| WO | 2014126885 A1 | 8/2014 | |
| WO | 2017-191274 | 11/2017 | |
| WO | 2017223179 A1 | 12/2017 | |
| WO | 2018-090006 | 5/2018 | |
| WO | 2018200258 A1 | 11/2018 | |
| WO | 2019-023648 | 1/2019 | |
| WO | 2019023648 A1 | 1/2019 | |
| WO | 2020040831 A1 | 2/2020 | |
| WO | 2020167937 A1 | 8/2020 | |
| WO | 2020205846 A1 | 10/2020 | |
| WO | 2020-227430 | 11/2020 | |
| WO | 2021071965 A1 | 4/2021 | |
| WO | 2021202523 A1 | 10/2021 | |
| WO | 2021222165 A1 | 11/2021 | |

OTHER PUBLICATIONS

U.S. Appl. No. 17/517,227 (Year: 2021).*
Roy, Thomas M. et al., "The effect of an aldose reductase inhibitor on cardiovascular performance in patients with diabetes melitus", Diabetes Research and Clinical Practice 1990, vol. 10, pp. 91-97.
Cannon, "Chapter Nineteen: Analog Design," Burger's Medicinal Chemistry and Drug Discovery: fifth edition, vol. 1: Principles and Practice, Wiley-Inter science, pp. 783-802 (1995).
Kinoshita, "A thirty year journey in the polyol pathway", Exp. Eye. Res., vol. 50, No. 6, pp. 567-573 (1990).
Sheridan, "The most common replacements in Drug-like compounds", J. Chem. Inf. Comput. Sci., vol. 42, pp. 103-108 (2002).
Cheng et al., "The effect of high glucose and oxidative stress on lens metabolism, aldose reductase, and senile cataractogenesis", Abstract only, Metabolism, Apr. 1986, vol. 35, No. 4 Suppl. 1, pp. 10-14.
Gu et al., "Effects of lignans extracted from Eucommia ulmoides and aldose reductase inhibitor epalrestant on hypertensive vascular remodeling", Abstract only, J. Ethnopharmacol, Jan. 17, 2011, vol. 133, No. 1, pp. 6-13.
Tawata et al., "Anti-platelet action of isoliquiritigenin, an aldose reductase inhibitor in licorice", Eur. J. Pharmacol, Feb. 25, 1992, vol. 212, No. 1, pp. 87-92.
Zeng et al., "Efficacy and safety of berberine for congestive heart failure secondary to ischemic or idiopathic dilated cardiomyophaty", abstract only, Am. J. Cardiol. Jul. 15, 2003, vol. 92, No. 2, pp. 173-176.
Zhou et al., "Neuroprotective effects of berberine on stroke modles in vitro and in vivo", abstract only, Neurosci. Lett., Dec. 5, 2008, vol. 447, No. 1, pp. 31-36.
Zhu, "Aldose Reductase Inhibitors as Potential Therapeutics Drugs of Diabetic Complications", Diabeties Mellitus—Insights and Persoectives Jan. 23, 2013, Chapter 2, pp. 17-46.
Mylari et al., "A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfony)-2H-pyridazin-3-one and Cibgebers", J. Med. Chem., 48, pp. 6326-6339 (2005).
Hartsock et al., "A Mouse Model of Retinal Ischemia-Reperfusion Injury Through Elevation of Intraocular Pressure", Journal of Visualized Experiments, 113, e54065, 6 pages (2016).
Alexander et al., "(Acyloxy)alkyl carbamates as novel bioreversible prodrugs for amines: increased permeation through biological membranes", J. Med. Chem., 31, pp. 318-322 (1988).
Ayres et al., "Synthesis of derivates of cyclobuteno[c]thiophen and attempts to synthesise thiophen analogues of bipheneylene", Tetrahedron, 31, pp. 1755-1760 (1975).
Carbone et al., "Structure of Aldehyde reductase in ternary complex with a 5-arylidene-2,4-thiazolidinedione aldose reductase inhibitor", European Journal of Medicinal Chemistry, 45(3):1140-1145, Mar. 31, 2010 available online Dec. 21, 2009 (5 pages).
Tammali et al., "Inhibitor of Aldose Reductase Prevents Angiogenesis in vitro and in vivo", published in final edited form as: Angiogenesis, 14(2), pp. 209-221 (May 2011) 19 pages.
Grewal et al., "Updates on Aldose Reductase Inhibitors for Management of Diabetic Complications and Non-diabetic Diseases"

(56) References Cited

OTHER PUBLICATIONS (Mini-Reviews in Medicinal Chemistry, 2016, vol. 16(2), pp. 120-162, [online], [retrieved Mar. 17, 2022] found in PubMed, RMS: 26349493, doi: 10.2174/1389557515666150909143737).

Tianhong Xu et al., "Indomethacin has a potent antiviral activity against SARS COV-2 in vitro and canine coronavirus in vivo" bioRxiv, Apr. 5, 2020, XP055742348, DOI: 10.1101/2020.04.01.017624 Retrieved from the Internet: URL: https://www.biorxiv.org/content/10.1101/2020.04.01.017624v1.full.pdf p. 5, para 2-3.

Ghosh Sutapa et al., "Recent Advances in Drug Discovery Research Using Structure-Based Virtual Screening Techniques: Examples of Success for Diverse Protein Targets" in "Drug Discovery Research", Jun. 8, 2007, John Wiley & Sons, Inc., Hoboken NJ, USA, XP055514110, ISBN: 978-0-471-67200-5 pp. 24-62, DOI: 10.1002/9780470131862.ch2 Retrieved from the Internet: https://doi.org/10.1002/9780470131862.ch2.

Li et al., "Decarboxylative borylation", Science, 2017, 356 (6342), 16 pages.

Pubchem, Substance Record for SID 227698804, Available Date: Feb. 12, 2015, Retrieved from the internet: https://pubchem.ncbi.nlm.nih.gov/substance/227698804 (7pages).

Clinical Trials.gov, "Ezetimibe Versus Nutraceuticals in Statin-intolerant Patients (ECLIPSE)", ClinicalTrials.Gov identifier No. NTC01490229, Fisrts received Dec. 8, 2011, 4 pages.

Clinical Trials.gov, "Low-dose Statins, and Nutraceuticals in High-intensity Statin-intolerant Patients (ADHERENCE)", ClinicalTrials.Gov identifier No. NTC02001883, first receiced Nov. 24, 2013, 4 pages.

Coelho et al. "Sweet and sour: an update on classic galactosemia" Journal of Inherited Metabolic Disease Mar. 9, 2017 vol. 40, p. 325-342; p. 331, left col. Para 4, p. 332, left col, para 4, p. 33, left col, para 3.

Aydin-Azemir et al. "Galactosemia and phantom absence seizures" Journal of Pediatric Neurosciences, Dec. 2014, vol. 9, p. 253-256; p. 1, introduction: para 1.

Sato et al. "Dose-Dependent Prevention of Sugar Cataracts in Galactose-fed Dogs by the Aldose Reductase Inhibitor M79175" Laboratory of Ocular Therapeutics, National Eye Institute, National Institutes of Health, Exo. Eye Res/ (1998) 66:217-222.

Maratha et al. Classical Galactosaemia and CDG, the N-Glycosylation Interface. A Review. JIMD Reports, Aug. 9, 2016, vol. 34, pp. 33-42; p. 34.

Xu et al. "Indomethacin has a potent antiviral activity against SARS CoV-2 in vitro and canine coranvirus in vivo" bioRxiv, Apr. 5, 2020, XP055742348, DOI: 10.1101/2020.04.01.017624 Retrieved from the Internet: URL: https://www.biorxiv.org/content/10.1101/2020.04.01.017624v1full.pdf p. 5, para 2-3.

Coyle et al. "A Recovered Case of COVID-19 Myocarditis and ARDS Treated with Corticosteroids, Tocilizumba, and Experimental AT-001", JACC. Case Reports, vol. 2, No. 9, Jul. 15, 2020, pp. 1331-1336, XP009528095, ISSN: 2666-0849, DOI: 10.1016/J.JACCAS Apr. 25, 2020 [retrieved on May 3, 2020] example 4.

Iyer et al. "Repurposing the aldose reductase inhibitor and diabetic neuropathy drug epalrestat for the congenital disorder of glycosylation PMM2-CDG" Dis. Model. Mech. (2019) 12(11). bioRxiv preprint first posted online May 3, 2019; doi: http://dx.doi.org/10.1101/626697.

Lao et al. "Yeast Models of Phosphomannomutase 2 Deficiency, a Congenital Disorder of Glycosylation" G3 (Bethesda, Md.), Feb. 7, 2019, 9(2):413-423.

Zhang et al. "Bioactivity Focus of α-Cyano-4-hydroxycinnamic acid (CHCA) Leads to Effective Multifunctional Aldose Reductase Inhibitors" Sci. Rep. (2016) 6:24942.

Maratha et al. "Classical Galactosaemia and CDG, the N-Glycosylation Interface. A Review" JIMD Reports, Aug. 9, 2016, vol. 34, 33-42.

International Search Report issued on PCT/US2021/024876 mailed on Jun. 30, 2021.

International Search Report and Written Opinion for PCT/US2020/017913 mailed on Jun. 16, 2020.

International Search Report issued on PCT/US2018/044199 mailed on Oct. 24, 2018.

International Search Report issued on PCT/US2020/017913 mailed on Jun. 16, 2020.

International Search Report issued on PCT/US2020/054607 mailed on Jan. 28, 2021.

Trippier et al."Boronic Acids in Medicinal Chemistry: anticancer, antibacterial and antiviral applications", Med. Chem. Commun 2010, vol. 1, pp. 183-198. p. 183, col. 1, para 4: p. 185, Table 2.

Chatzopoulou et al. "Novel Aldose Reductase Inhibitors: a patent survey (2006-present)", Expert Opinion on Therapeutic Patents, 2012, vol. 22:11, pp. 1303-1323, p. 1307, Figure 4.

Veves, "Aldose Reductase Inhibitors for the treatment of Diabetic Neuropathy", Contemporary Diabetes: Diabetic Neuropathy: Clinical Management, Second edition, Humana Press, chapter 18, pp. 309-320 (2007).

Kajiwara et al., "Lower incidence of myocardial infarction in type 2 duabetic patients with polyneuropathy who were treated with an aldoses reductacse inhibitor (epalrestat): a retrospective study", Presentation Abstract, Presentation No. 1241, 47th EASD Annual Meeting, Lisbon, 2011.

Hotta et al., "Stratified analyses for selecting appropriate target patients with diabetic peripheral neuropathy for long-term treatment with an aldose reductase inhibitor, epalrestant", Diabet. Med. (2008), vol. 25, No. 7, pp. 818-825.

Yagihashi et al., "Neuropathy in diabetic mice overexpressing human aldose reducatse and effects of aldose reductase inhibitor", Abstract only, Brain, Dec. 2001, vol. 124, Pt. 12, pp. 2448-2458.

Hu et al., "Efficacy and Safety of aldose reductase inhibitor for the treatment of diabetic cardiovascular autonomic neuropathy: systematic review and meta-analysis", Plos One, 9(2), e87096, pp. 1-11 (2014).

Satoh et al., "Effect of Ranirestat on Sensory and Motor Nerve Function in Japanese Patients with Diabetic Polyneuropathy: A Randomized Double-Blind Placebo-Controlled Study", J. Diabetes Res. 2016, article ID 5383797, 8 pages (2016).

Hotta et al., "Short Report: Treatment—Long-term clinical effects of epalrestat, an aldose reductase inhibitor, on progression of diabetics neuropathy and other microvascular complications; multiverse epodemiological analysis based on patient background factors and severity of diabetic neuropathy", Diabetic Medicine, 29:1529-1533, 2012 (5 pages).

Hotta et al. "Long-Term Clinical Effects of Epalrestat, an Aldose Reductase Inhibitor, on Diabetic Peripheral Neuropathy", Diabetes Care, 29(7), pp. 1538-1544 (Jul. 2006).

Il et al., "Redox State-Dependent and Sorbitol Accumulation-Independent Diabetic Albuminuria in Mice with Transgene-Derived Human Aldose Reductase and Sorbitol Dehydrogenase Deficiency", Diabetologia, Feb. 14, 2004, vol. 47, No. 3, pp. 541-548 entire document.

Cortese et al., "Biallelic Mutations in SORD cause a common and Potentially Treatable Hereditary Neuropathy with Implications for Diabetes", Nature Genetics, Articles https://doi.org/10.1038/s41588-020-0615-4, 19 pages.

Ridel et al., "An Updated Review of the Long-Term Neurological Effects of Galactosemia," Pediatric Neurology(2005) 33(3):153-161.

Hohman et al. "Probing the Inhibitor-binding site of aldose reductase with site-directed mutagenesis", Eur. J. Biochem 1998, vol. 256, pp. 310-316.

Mylari, Banavara L. et al., "Novel, Potent Aldose Reductase Inhibitors: 3,4-Dihydro-4-oxo-3-[[5-(trifluoromethyl)-2-benzothiazolyl]-1-phthalazine-acetic Acid (Zopolrestat) and Congeners", J. Med. Chem., 1991, vol. 34, pp. 108-122.

Mylari, Banavara L., et al.,"Potent, Orally Active Aldose Reductase Inhibitors Related to Zopolrestant: Sirrogates for Benzothiazole Side Chain", J. Med. Chem., 1992, vol. 35, pp. 457-465.

Hwang et al., "Central role for aldose reductase pathway in myocardial ischemic injury" The FASEB Journal, Aug. 2004, vol. 18, No. 11, pp. 1192-1199.

Mylari et al., "Orally active aldose reductase inhibitors related to Zopolrestat: Surrogates for Benzothiazole Side Chain", J. Med. Chem. Vol. 35, pp. 2155-2162 (1992).

(56) References Cited

OTHER PUBLICATIONS

Wilson et al., "Refined 1.8 a structure of human aldose reductase comlexed with the potent inhibitor zopolrestat", Proc. Natl. Acad. Sci. USA, vol. 90, No. 21, pp. 9847-9841 (Nov. 1993).
Kalofoutis et al., "Type II diabetes mellitus and cardiovascular risk factors: current therapeutic approaches" Exp. Clin. Cardiol., 2007, vol. 12, No. 1 pp. 17-28.
Zhu, C. "Diabetes Mellitus-insights and perspectives", chapter 2, book edited by Oluwafemi O. Oguntibeju, published: Jan. 23, 2013 under CC BY 3.0 License.
Lightman, S. Does Aldose Reductase have a role in the development of the ocular complications of diabetes? Eye, 1993, vol. 7, pp. 238-241.
Digiacomao, M. "Synthesis and functional evaluation of novel aldose reductase inhibitors" The Open Medicinal Chemistry Journal, Apr. 2017, vol. 11, abstract.
Ramasamy et al., "Aldose reductase and cardiovascular diseases, creating human-like diabetic complications in an experimental model" Circ Res, May 2010, vol. 106, No. 9, pp. 1449-1458.
Nour et al. "Ischemia-Reperfusion Injury in Stroke" Intervent Neurol, 2012, vol. 1, pp. 185-199.
Jacoby et al., "Acute Myocardial Infarction in the Diabetic Patient: Pathophysiology, Clinical course and Prognosis", J. Am. Coll. Cardio., vol. 20, No. 3, pp. 736-744 (1992).
Beyer-Mears et al., Glomerular Polyol Accumulation in Diabetes and its Prevention by Oral Sorbinil, Diabetes, Jun. 1984, vol. 33, No. 6, pp. 604-607.
Caliceti et al., "New Insights from Pharmacological Aspects to Clinical Evidences in the Management of Metabolic Disorders", Abstract only, Curr. Med. Chem. (2016) vol. 23, No. 14, pp. 1460-1476.
Cheung et al., "Aldose Reductase Deficiency Prevents Diabetes-Induced Blood-Retinal Barrier Breakdown, Apoptosis, and Glial Reactivation in the Retina of db/db Mice," Diabetes, Nov. 2005, vol. 54, No. 11 pp. 3119-3125.
Johnson et al., "Cardiac Abnormalities in Diabetic Patients with Neuropathy", Diabetes Care, Feb. 2004, vol. 27, No. 2, pp. 448-454.
Kasajima et al., "Enhanced in situ expression of aldose reductase in peripheral nerve and renal glomeruli in diabetic patients", Abstract only, Virchows Arch., Jul. 2001, vol. 439, No. 1.
Li et al., "Polyol pathway and modulation of ischemia-reperfusion injury in Type2 diabetic BBZ rat hearts", Cardiovascular Diabetology, Oct. 28, 2008, vol. 7, No. 33, 11 pages.
Liu et al., "Genetic deficiency of aldose reductase counteracts the development of diabetic nephropathy in C57BL/6 mice", Diabetologia, Jan. 27, 2011, vol. 54, No. 5, pp. 1242-1251.
Marin-Neto et al., Cardiovascular effects of berberine in patients with severe congestive heart failure, Clin. Cardiol., Apr. 1988, vol. 11, No. 4, pp. 253-260.
Price et al., "Mitogen-Activated Protein Kinase p38 Mediates Reduced Nerve Conduction Velocity in Experimental Diabetic Neuropathy", Diabetes, Jul. 2004, vol. 53, No. 7 pp. 1851-1856.
Schulz et al., "Identification of novel downstream targets of platelet glycoprotein VI activation by differential proteome analysis: implications for thrombus formation", Blood, May 20, 2010, vol. 115, No. 20, pp. 4102-4110.
Tang et al., "Aldose reductase, oxidative stress, and diabetic mellitus", Frontiers in Pharmacology, May 9, 2012, vol. 3, Article 87, 8 pages.
Tang et al., "Glucose and collagen regulate human platelet activity through aldose reductase induction of thromboxane", The Journal of Clinical Investigation, No. 2011, vol. 121, No. 11 pp. 4462-4476.
Vedantham et al., "Human Aldose Reductase Expression Accelerates Atherosclerosis in Diabetic apolipoprotein E-/-Mice Reductase", Arteriosler. Thromb. Vasc. Biol. vol. 31, No. 8 pp. 1805-1813, Author Manuscript Aug. 1, 2012.
Lorenzi, "The Polyol Pathway as a Mechanism for Diabetic Retinopathy: Attractive, Elusive and Resilient", Experimental Diabetes Research, vol. 2007, Article ID 61038, 10 pages (2007).
Antonetti et al., "Vascular Permeability in Experimental Diabetes is Associates with Reduced Endothelial Occludin Content: Vascular Endothelial Growth Factor Decreases Occludin in Retinal Endothlial Cells", Diabetes, 47, pp. 1953-1959 (Dec. 1998).
Berge et al., "Pharmaceutical Salts", J. Pharm. Sci., 66(1), pp. 1-19 (1977).
Ramana et al., "Inhibitor of aldose reductase prevents growth factor-induced G1-S phase transition through the AKT/phosphoinositide 3-kinase/E2F-1 pathway in human colon cancer cells", Mol. Cancer Therapeutics, 9(4), pp. 813-824 (2010).
Srivasrava et al., "Aldose reductase inhibition suppressed oxidative stress-induced inflammatory disorders", author manuscript, published in final edited form as : Chem. Biol. Interact, 1991, pp. 330-338 (2011), 19 pages.
International Search Report and Written Opinion mailed on Jul. 11, 2018 for PCT/US2018/027960.
International Search Report and Written Opinion mailed on Jun. 17, 2020 for PCT/US2020/025928.
International Search Report and Written Opinion mailed Aug. 12, 2020 for PCT/US2020/031708.
International Search Report and Written Opinion mailed Dec. 6, 2011 for PCT/US2011/044038.
International Search Report and Written Opinion mailed Aug. 11, 2021 for PCT/US2021/029286.
International Search Report and Written Opinion mailed on Oct. 13, 2017 for PCT/US2017/038505.
"Learn the Genetics of Diabetes" [online] American Diabetes Association, [retrieved on Nov. 9, 2022]. Retrieved from the Internet: <URL: https://diabetes.org/diabetes/genetics-diabetes>.
Kamijo, M et al. "Galactosemia produces ARI-preventable nodal changes similar to those of diabetic neuropathy," Diabetes Research and Clinical Practice (1994) 25:117-129.
Monticelli, et al., "β-Glucose-1,6-Bisphosphate Stabilizes Pathological Phophomannomutase2 Mutants In Vitro and Represents a Lead Compound to Develop Pharmacological Chaperones for the Most Common Disorder of Glycosylation, PMM2-CDG", International Journal of Molecular Sciences (2019) 20(4164):3-15.
Patil et al., "The Fate of Aldose Reductase Inhibition and Sorbitol Dehydrogenase Activation", Austin Journal of Endocrinology and Diabetes (2019) 6(1):1-7.
Hao, W. et al., "Hyperglycemia Promotes Schwann Cell De-differentiation and De-myelination via Sorbitol Accumulation and Igf1 Protein Down-regulation", The Journal of Biological Chemistry (2015) 290(28):17106-17115.
Miyamoto, S., et al., "Recent advances in aldose reductace inhibitors: potential agents for the treatment of diabetic complications", Expert Opin. Ther. Pat. (2002) 12(5):621-631.
Nambu, H., et al., "Attenuation of aldose reductase gene suppresses high-glucose-induced apoptosis and oxidative stress in rat lens epithelial cells", Diabetes Res Clin Pract (2008) 82(1):18-24.
Hoyle, J.C. et al., "The genetics of Charcot-Marie-Tooth disease: current trends and future implications for diagnosis and management", The Application of Clinical Genetics (2015) vol. 8, pp. 235-243.
Klein, C.J. et al., "Inherited neuropathies: Clinical overview and update", Muscle Nerve (2013) 48(4):604-622.

\* cited by examiner

SORD exon 7   GTAGATGCCGCTGGATGGAGGCCTCTGCCCCGTGCACTCGATGGTGACTTCCGGCTTGCACCCCAGCTGA
SEQ ID NO:43
_ORD2P exon 7  GTAGATGCCTGCTGGATGGAGGCCTCTGCCCCGTGCACTCGATGGTGACTTCCGGCTTGCACCCCAGCAGA
SEQ ID NO:44

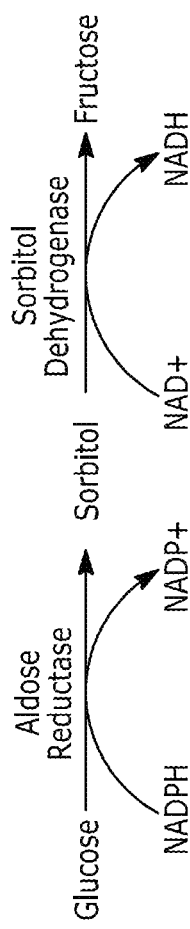
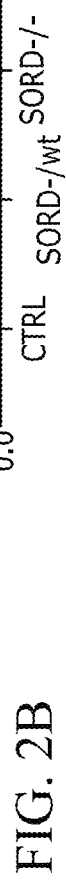
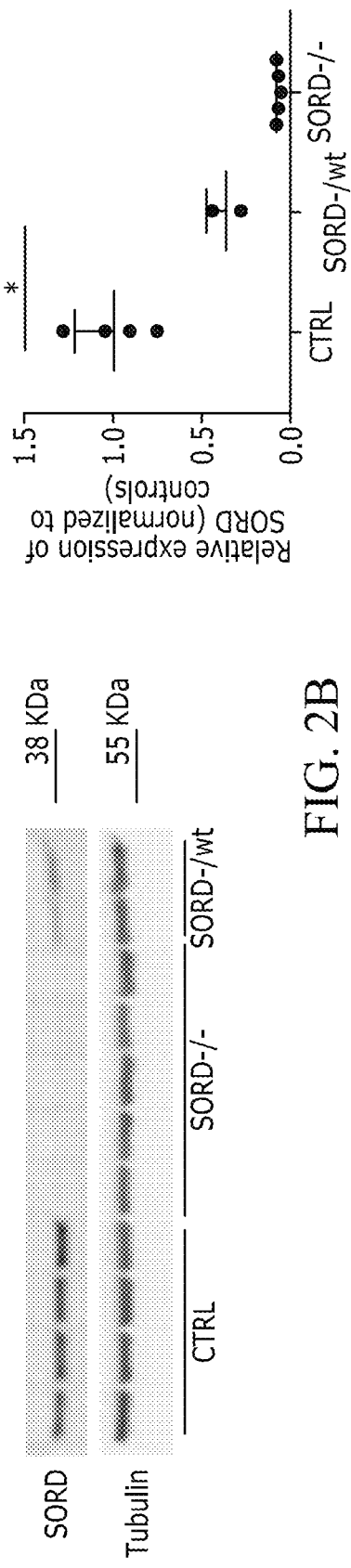
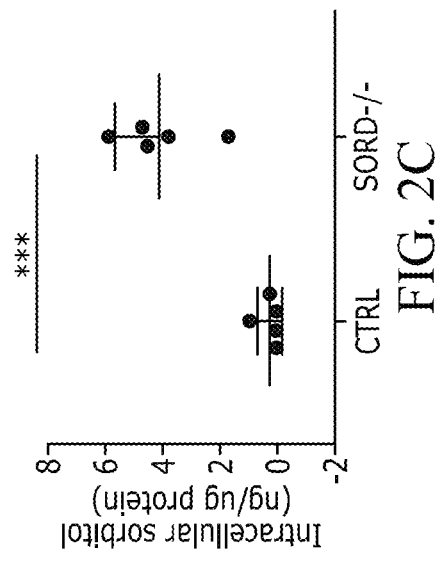
FIG. 2A
FIG. 2B
FIG. 2C

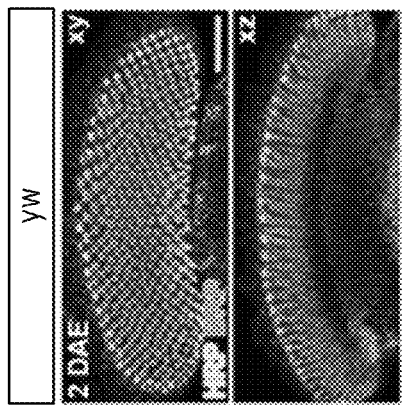
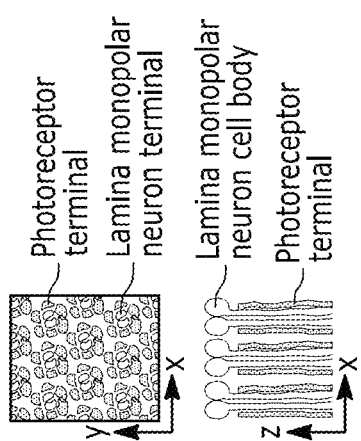
FIG. 3B
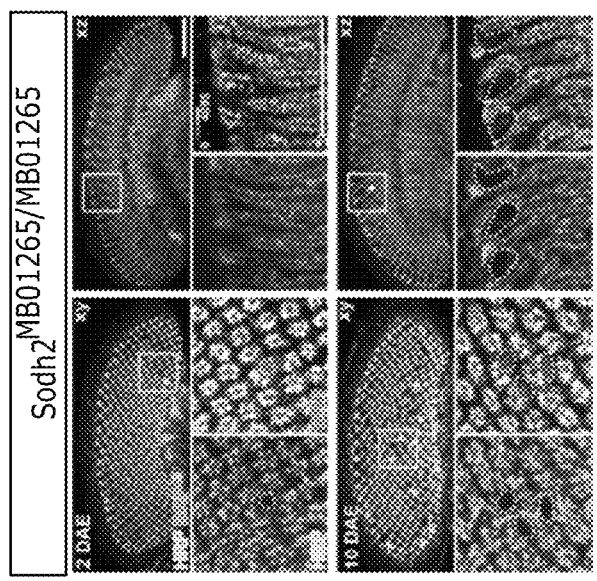
FIG. 3C
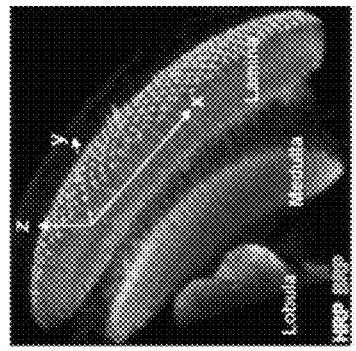
FIG. 3A

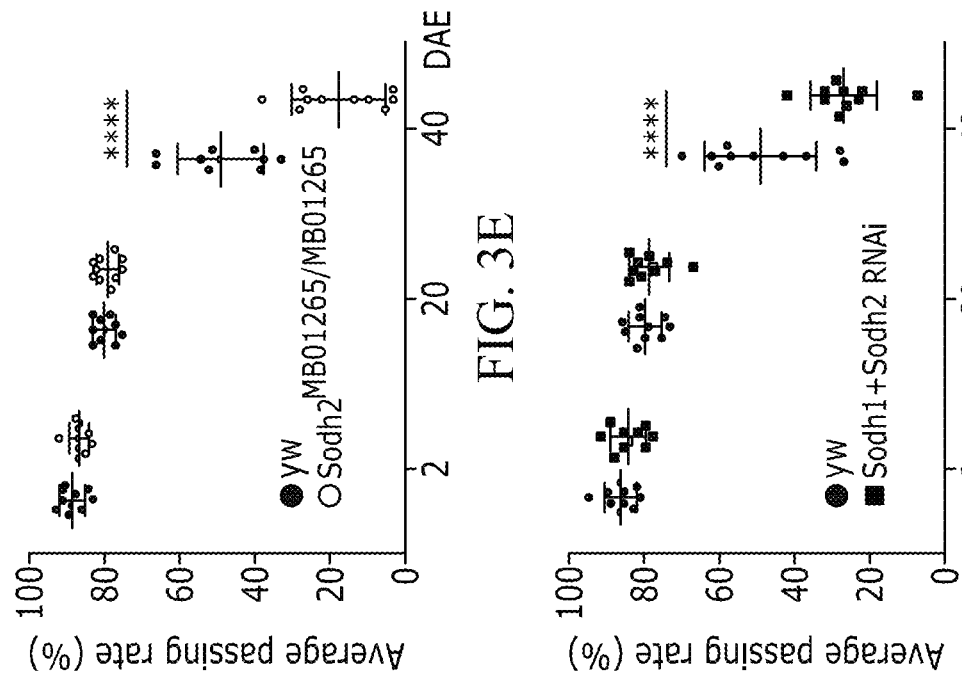
FIG. 3E
FIG. 3F
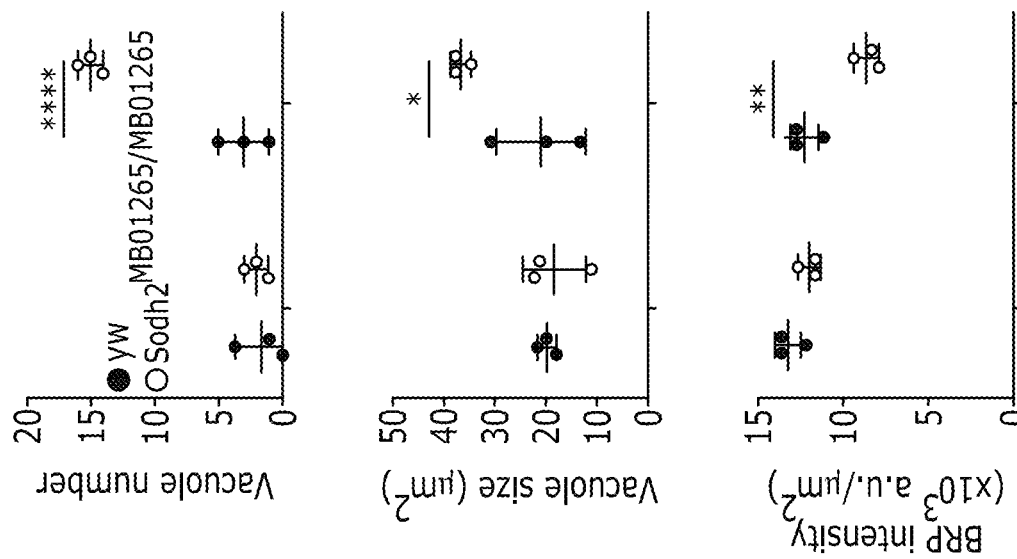
FIG. 3D

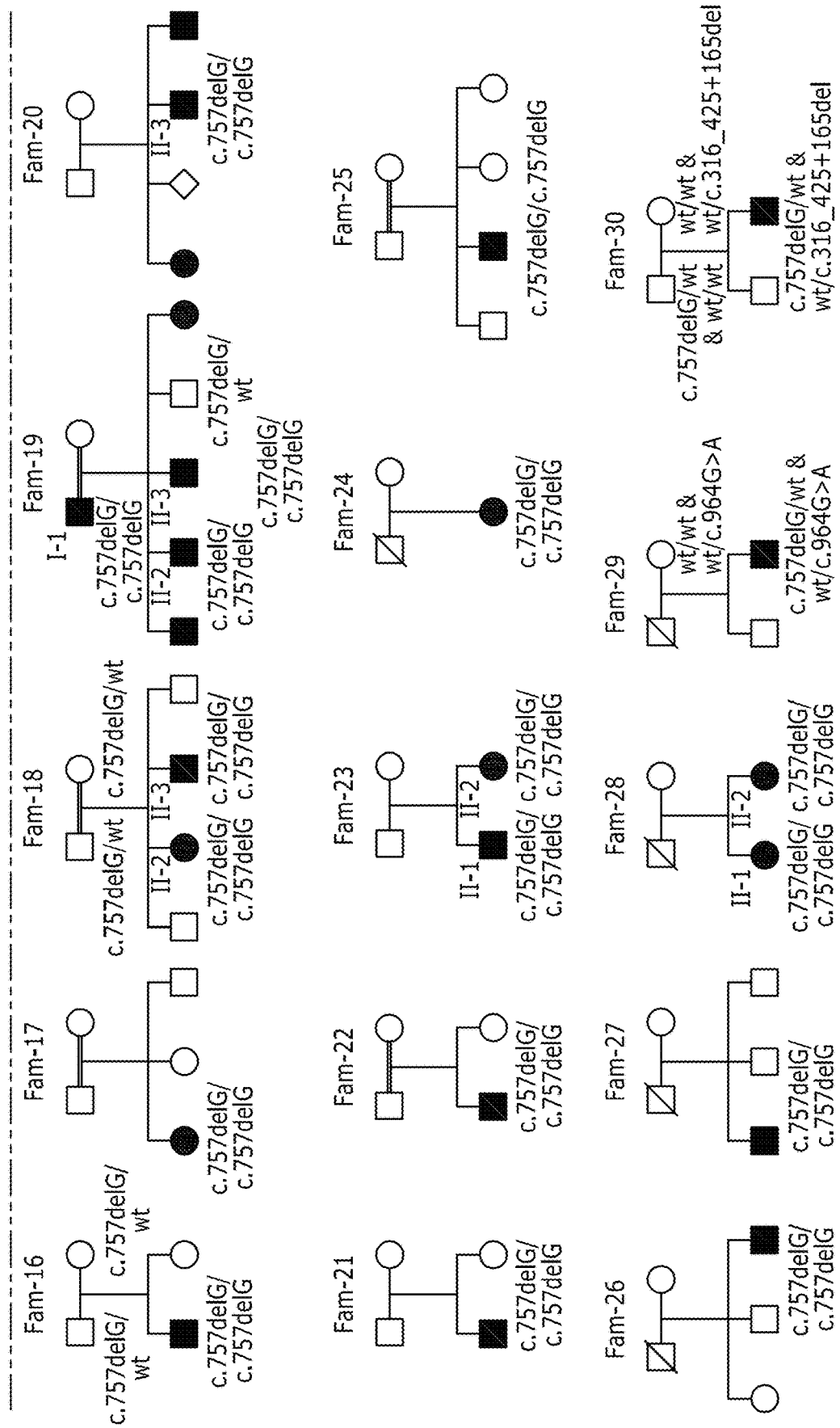
FIG. 5CONT.

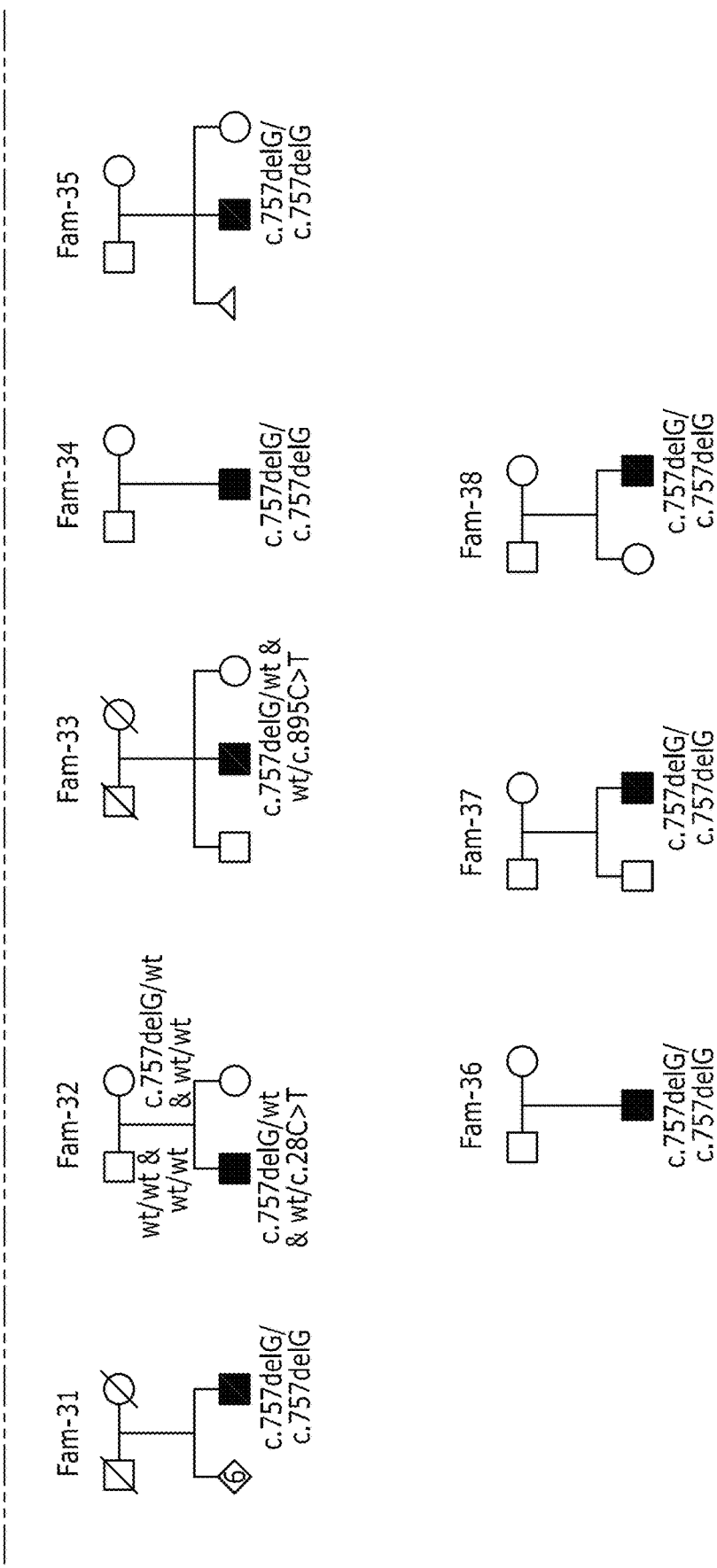
FIG. 5CONT.

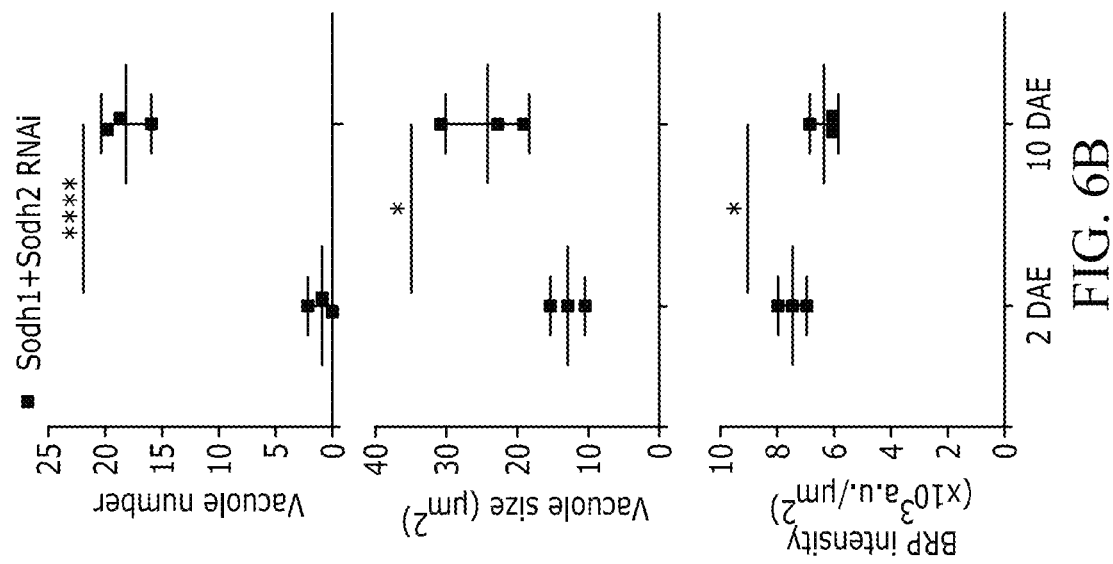
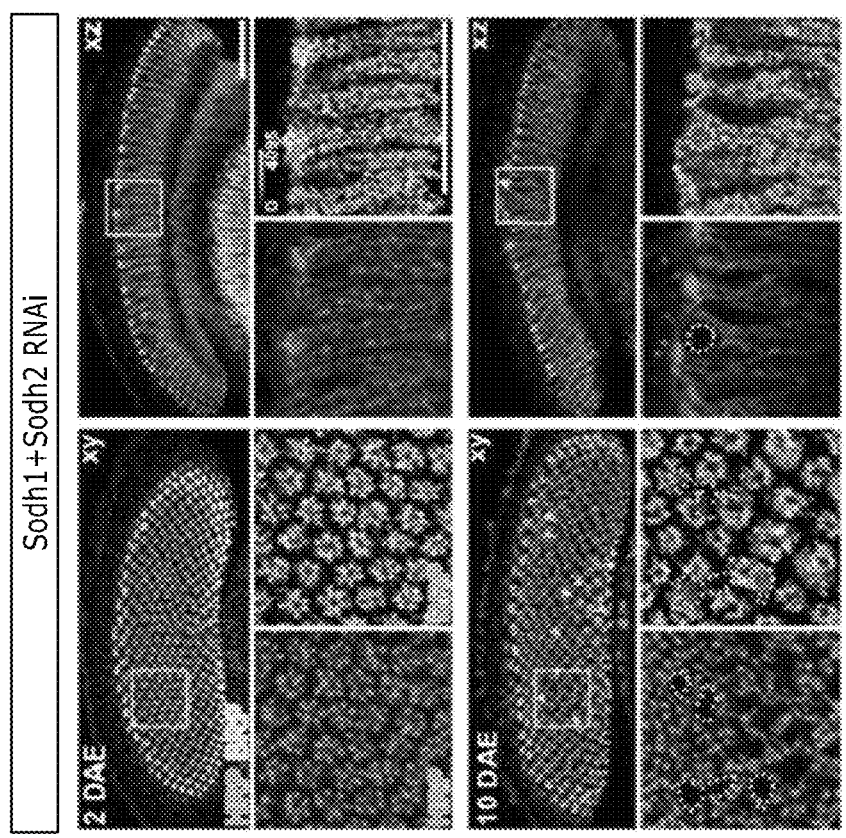
FIG. 6A
FIG. 6B

> [pAAV-SORD.xdna] - 5756 bp SEQ ID NO: 48
CCTGCAGGCAGCTGCGCGCTCGCTCGCTCACTGAGGCCGCCCGGGCAAAGCCCGGGCGTCGGGCGACCTTTGGTCGCCCG
GCCTCAGTGAGCGAGCGAGCGCGCAGAGAGGGAGTGGCCAACTCCATCACTAGGGGTTCCTGCGGCCGCAACCGTCTAGT
TATTAATAGTAATCAATTACGGGGTCATTAGTTCATAGCCCATATATGGAGTTCCGCGTTACATAACTTACGGTAAATGG
CCCGCCTGGCTGACCGCCCAACGACCCCCGCCCATTGACGTCAATAATGACGTATGTTCCCATAGTAACGCCAATAGGGA
CTTTCCATTGACGTCAATGGGTGGAGTATTTACGGTAAACTGCCCACTTGGCAGTACATCAAGTGTATCATATGCCAAGT
ACGCCCCCTATTGACGTCAATGACGGTAAATGGCCCGCCTGGCATTATGCCCAGTACATGACCTTATGGGACTTTCCTAC
TTGGCAGTACATCTACGTATTAGTCATCGCTATTACCATGGTGATGCGGTTTTGGCAGTACATCAATGGGCGTGGATAGC
GGTTTGACTCACGGGGATTTCCAAGTCTCCACCCCATTGACGTCAATGGGAGTTTGTTTTGGCACCAAAATCAACGGGAC
TTTCCAAAATGTCGTAACAACTCCGCCCCATTGACGCAAATGGGCGGTAGGCGTGTACGGTGGGAGGTCTATATAAGCAG
AGCTCGTTTAGTGAACCGTCAGATCGCCTGGAGACGCCATCCACGCTGTTTTGACCTCCATAGAAGACACCGGGACCGAT
CCAGCCTCCGCGGATTCGAATCCCGGCCGGGAACGGTGCATTGGAACGCGGATTCCCCGTGCCAAGAGTGACGTAAGTAC
CGCCTATAGAGTCTATAGGCCCACAAAAAATGCTTTCTTCTTTTAATATACTTTTTTGTTTATCTTATTTCTAATACTTT
CCCTAATCTCTTTCTTTCAGGGCAATAATGATACAATGTATCATGCCTCTTTGCACCATTCTAAAGAATAACAGTGATAA
TTTCTGGGTTAAGGCAATAGCAATATTTCTGCATATAAATATTTCTGCATATAAATTGTAACTGATGTAAGAGGTTTCAT
ATTGCTAATAGCAGCTACAATCCAGCTACCATTCTGCTTTTATTTTATGGTTGGGATAAGGCTGGATTATTCTGAGTCCA
AGCTAGGCCCTTTTGCTAATCATGTTCATACCTCTTATCTTCCTCCCACAGCTCCTGGGCAACGTGCTGGTCTGTGTGCT
GGCCCATCACTTTGGCAAAGAATTGGGATTCGAACATCGATCCGACAGAGATCTGCGACCGCGATCGCCGGCGCCATGG
CGGCGGCGGCCAAGCCCAACAACCTTTCCCTGGTGGTGCACGGACCGGGGGACTTGCGCCTGGAGAACTATCCTATCCCT
GAACCAGGCCCAAATGAGGTCTTGCTGAGGATGCATTCTGTTGGAATCTGTGGCTCAGATGTCCACTACTGGGAGTATGG
TCGAATTGGGAATTTTATTGTGAAAAAGCCCATGGTGCTGGGACATGAAGCTTCGGGAACAGTCGAAAAAGTGGGATCAT
CGGTAAAGCACCTAAAACCAGGTGATCGTGTTGCCATCGAGCCTGGTGCTCCCCGAGAAAATGATGAATTCTGCAAGATG
GGCCGATACAATCTGTCACCTTCCATCTTCTTCTGTGCCACGCCCCCCGATGACGGGAACCTCTGCCGGTTCTATAAGCA
CAATGCAGCCTTTTGTTACAAGCTTCCTGACAATGTCACCTTTGAGGAAGGCGCCCTGATCGAGCCACTTTCTGTGGGGA
TCCATGCCTGCAGGAGAGGCGGAGTTACCCTGGGACACAAGGTCCTTGTGTGTGGAGCTGGGCCAATCGGGATGGTCACT
TTGCTCGTGGCCAAAGCAATGGGAGCAGCTCAAGTAGTGGTGACTGATCGTGTCTGCTACCCGATTGTCAAAGCCAAGGA
GATTGGGGCTGATTTAGTCCTCCAGATCTCCAAGGAGAGCCCTCAGGAAATCGCCAGGAAAGTAGAAGGTCAGCTGGGGT
GCAAGCCGGAAGTCACCATCGAGTGCACGGGGCAGAGGCCTCACTCCAGGCGGGCATCTACGCCACTCGCTCTGGTGGG
AACCTCGTGCTTGTGGGGCTGGGCTCTGAGATGACCACCGTACCCCTACTGCATGCAGCCATCCGGGAGGTGGATATCAA
GGGCGTGTTTCGATACTGCAACACGTGGCCAGTGGCGATTTCGATGCTTGCGTCCAAGTCTGTGAATGTAAAACCCTCG
TCACCCATAGGTTTCCTCTGGAGAAAGCTCTGGAGGCCTTTGAAACATTTAAAAAGGGATTGGGGTTGAAAATCATGCTC
AAGTGTGACCCCAGTGACCAGAATCCCTGAAGATCTCAAGCTTAACTAGCTAGCGGACCGACGCGTACGCGGCCGCTCGT
TTAAACGGCCGCGGATCTACGGGTGGCATCCCTGTGACCCCTCCCCAGTGCCTCTCCTGGCCCTGGAAGTTGCCACTC
CAGTGCCCACCAGCCTTGTCCTAATAAAATTAAGTTGCATCATTTTGTCTGACTAGGTGTCCTTCTATAATATTATGGG
TGGAGGGGGTGGTATGGAGCAAGGGCAAGTTGGGAAGACAACCTGTAGGGCCTGCGGGGTCTATTGGGAACCAAGCTG
GAGTGCAGTGGCACAATCTTGGCTCACTGCAATCTCCGCCTCCTGGGTTCAAGCGATTCTCCTGCCTCAGCCTCCCGAGT
TGTTGGGATTCCAGGCATGCATGACCAGGCTCAGCTAATTTTTGTTTTTTGGTAGAGACGGGGTTTCACCATATTGGCC
AGGCTGGTCTCCAACTCCTAATCTCAGGTGATCTACCCACCTTGGCCTCCCAAATTGCTGGGATTACAGGCGTGAACCAC
TGCTCCCTTCCCTGTCCTTCTGATTTTGTAGGTAACCACGTGCGGACCGAGCGGCCGCAGGAACCCCTAGTGATGGAGTT
GGCCACTCCCTCTCTGCGCGCTCGCTCGCTCACTGAGGCCGGGCGACCAAAGGTCGCCCGACGCCCGGGCTTTGCCCGGG
CGGCCTCAGTGAGCGAGCGAGCGCGCAGCTGCCTGCAGGGGCGCCTGATGCGGTATTTTCTCCTTACGCATCTGTGCGGT
ATTTCACACCGCATACGTCAAAGCAACCATAGTACGCGCCCTGTAGCGGCGCATTAAGCGCGGCGGGTGTGGTGGTTACG
CGCAGCGTGACCGCTACACTTGCCAGCGCCCTAGCGCCCGCTCCTTTCGCTTTCTTCCCTTCCTTTCTCGCCACGTTCGC
CGGCTTTCCCCGTCAAGCTCTAAATCGGGGGCTCCCTTTAGGGTTCCGATTTAGTGCTTTACGGCACCTCGACCCCAAAA
AACTTGATTTGGGTGATGGTTCACGTAGTGGGCCATCGCCCTGATAGACGGTTTTTCGCCCTTTGACGTTGGAGTCCACG
TTCTTTAATAGTGGACTCTTGTTCCAAACTGGAACAACACTCAACTCTATCTCGGGCTATTCTTTTGATTTATAAGGGAT
TTTGCCGATTTCGGTCTATTGGTTAAAAAATGAGCTGATTTAACAAAAATTTAACGCGAATTTTAACAAAATATTAACGT
TTACAATTTTATGGTGCACTCTCAGTACAATCTGCTCTGATGCCGCATAGTTAAGCCAGCCCCGACACCCGCCAACACCC
GCTGACGCGCCCTGACGGGCTTGTCTGCTCCCGGCATCCGCTTACAGACAAGCTGTGACCGTCTCCGGGAGCTGCATGTG
TCAGAGGTTTTCACCGTCATCACCGAAACGCGCGAGACGAAAGGGCCTCGTGATACGCCTATTTTTATAGGTTAATGTCA
TGATAATAATGGTTTCTTAGACGTCAGGTGGCACTTTTCGGGGAAATGTGCGCGGAACCCCTATTTGTTTATTTTTCTAA
ATACATTCAAATATGTATCCGCTCATGAGACAATAACCCTGATAAATGCTTCAATAATATTGAAAAAGGAAGAGTATGAG
TATTCAACATTTCCGTGTCGCCCTTATTCCCTTTTTTGCGGCATTTTGCCTTCCTGTTTTTGCTCACCCAGAAACGCTGG
TGAAAGTAAAAGATGCTGAAGATCAGTTGGGTGCACGAGTGGGTTACATCGAACTGGATCTCAACAGCGGTAAGATCCTT
GAGAGTTTTCGCCCCGAAGAACGTTTTCCAATGATGAGCACTTTTAAAGTTCTGCTATGTGGCGCGGTATTATCCCGTAT
TGACGCCGGGCAAGAGCAACTCGGTCGCCGCATACACTATTCTCAGAATGACTTGGTTGAGTACTCACCAGTCACAGAAA
AGCATCTTACGGATGGCATGACAGTAAGAGAATTATGCAGTGCTGCCATAACCATGAGTGATAACACTGCGGCCAACTTA
CTTCTGACAACGATCGGAGGACCGAAGGAGCTAACCGCTTTTTTGCACAACATGGGGGATCATGTAACTCGCCTTGATCG
TTGGGAACCGGAGCTGAATGAAGCCATACCAAACGACGAGCGTGACACCACGATGCCTGTAGCAATGGCAACAACGTTGC
GCAAACTATTAACTGGCGAACTACTTACTCTAGCTTCCCGGCAACAATTAATAGACTGGATGGAGGCGGATAAAGTTGCA
GGACCACTTCTGCGCTCGGCCCTTCCGGCTGGCTGGTTTATTGCTGATAAATCTGGAGCCGGTGAGCGTGGGTCTCGCGG
TATCATTGCAGCACTGGGGCCAGATGGTAAGCCCTCCCGTATCGTAGTTATCTACACGACGGGGAGTCAGGCAACTATGG
ATGAACGAAATAGACAGATCGCTGAGATAGGTGCCTCACTGATTAAGCATTGGTAACTGTCAGACCAAGTTTACTCATAT
ATACTTTAGATTGATTTAAAACTTCATTTTTAATTTAAAAGGATCTAGGTGAAGATCCTTTTTGATAATCTCATGACCAA
AATCCCTTAACGTGAGTTTTCGTTCCACTGAGCGTCAGACCCCGTAGAAAAGATCAAAGGATCTTCTTGAGATCCTTTTT
TTCTGCGCGTAATCTGCTGCTTGCAAACAAAAAAACCACCGCTACCAGCGGTGGTTTGTTTGCCGGATCAAGAGCTACCA
ACTCTTTTTCCGAAGGTAACTGGCTTCAGCAGAGCGCAGATACCAAATACTGTTCTTCTAGTGTAGCCGTAGTTAGGCCA
CCACTTCAAGAACTCTGTAGCACCGCCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGCGGTCGGGCTGAACGGGGGGTTCGTGC
ACACAGCCCAGCTTGGAGCGAACGACCTACACCGAACTGAGATACCTACAGCGTGAGCTATGAGAAAGCGCCACGCTTCC
CGAAGGGAGAAAGGCGGACAGGTATCCGGTAAGCGGCAGGGTCGGAACAGGAGAGCGCACGAGGGAGCTTCCAGGGGGAA
ACGCCTGGTATCTTTATAGTCCTGTCGGGTTTCGCCACCTCTGACTTGAGCGTCGATTTTTGTGATGCTCGTCAGGGGGG
CGGAGCCTATGGAAAAACGCCAGCAACGCGGCCTTTTTACGGTTCCTGGCCTTTTGCTGGCCTTTTGCTCACATGT

*FIG. 9*

Supplemental Table 1 | Primers sequences and thermocycling conditions

| | Primers | SEQ ID NO: | Reagents | Thermocycling conditions |
|---|---|---|---|---|
| SORD Exon 1 | Fw/sequencing: CAGGCTGGCACAAAGGAG<br>Rv: AGTGAGGCAGGATCGGTATG | 2<br>3 | Faststart Master Mix 2X (Roche)<br>Primers 0.5 mM<br>genomic DNA 50 ng | 95°C 4 min<br>[95°C 30 s<br>65°C 30 s - Each cycle decreasing by 0.5°C<br>72°C 1 min] X18 cycles<br>[95°C 30s<br>55°C 30s<br>72°C 1 min] X18 cycles<br>72°C 5 min |
| SORD Exon 2 | Fw/sequencing: AGCGTGCCATTAGCGTATC<br>Rv: GCAGTAGACTCGTTCTCAGCCTAAC | 4<br>5 | | |
| SORD Exon 3 | Fw ACCTTTTCTCATAAATAGATACGAATCC<br>Rv/sequencing TCTTGTTCCCTGCTGTACCC | 6<br>7 | | |
| SORD Exon 4 | Fw and sequencing GCATGCAAGCCTTCATAACA<br>Rv CGAGGTCATTGTTGTTATGACG | 8<br>9 | | |
| SORD Exon 5 | Fw/sequencing CGTGGCCATGTTAACTCCTT<br>Rv GTTCCCTGAATTCCCAGTCA | 10<br>11 | | |
| SORD Exon 6 | Fw/sequencing ATGTTAATATTTCACGAACATATTCC<br>Rv GCTGTTTCCCAGTCAAGGAG | 12<br>13 | | |
| SORD exon 7 | Fw TGAGTCATCAGATTTCTCTGTTTG<br>Rv AGCCTGGGCGACTGAGTGAG<br>Sequencing AAAAGAAAACATAGATGGCAAAAGA | 14<br>15<br>16 | | |
| SORD exon 8 | Fw/sequencing TCCCGCTCAGTTAAGTTTGG<br>Rv GCTTCAAAATCCCCCCTTC | 17<br>18 | | |
| SORD exon 9 | Fw/sequencing CACCTGGCTCTTTCCTCTTG<br>Rv CCCTGAGAGATCCCAAGACTG | 19<br>20 | | |
| SORD2P exon 7 | Fw<br>Rv | | | |

PCR: polymerase chain reaction; Fw: forward; Rv: reverse

FIG. 10

| Case ID | Family ID | Gender | Age of onset | Age at exam | Ethnicity and origin | Family history | Diagnosis | Symptom at onset | Additional symptoms and signs | motor NCS | sensory NCS UL/LL | Disease severity | c.753delG; p.(Ala253GlnfsTer27) variant in SORD | Second variant in SORD |
|---|---|---|---|---|---|---|---|---|---|---|---|---|---|---|
| 1 | Fam 1 | female | 10 | 43 | White American | yes | CMT2 | walking difficulties | | axonal | not available | mild | homozygous | |
| 2 | Fam 1 | female | 10 | 38 | White American | yes | CMT2 | distal atrophy of lower limbs | | axonal | not available | mild | homozygous | c.298C>T; p.(Arg100Ter) (absent in the mother, father deceased) |
| 3 | Fam 2 | male | 15 | 39 | White Greek | no | CMT2 (motor predominant) | unable to stand on toes and heels | Rapid onset after flu-like syndrome, upper limb tremor | axonal | reduced/absent | mild | heterozygous (maternal) | |
| 4 | Fam 3 | male | 13 | 17 | White French | no | CMT intermediate | difficulties running and jumping, ankle sprains | upper limb tremor, mild hearing loss | intermediate | reduced/reduced | moderate | heterozygous (paternal) | c.329G>C; p.(Arg110Pro) (maternal) |
| 5 | Fam 4 | male | 14 | 20 | White American | no | CMT2 (motor predominant) | unable to stand on toes, walking difficulties | muscle ache, raised CK up to 1200 iU, scapular winging | axonal | reduced/normal | mild | homozygous | |
| 6 | Fam 5 | male | 12 | 23 | White American | no | dHMN | walking and running difficulties, decreased sport performance | upper limb tremor | axonal | normal/normal | mild | homozygous | |
| 7 | Fam 6 | female | 28 | 59 | White American | no | dHMN | unsteadiness | | axonal | normal/normal | mild | homozygous | |
| 8 | Fam 7 | male | 14 | 29 | Middle Eastern Iraqi | yes | dHMN | not available | balance problems during pregnancy | axonal | normal/reduced | mild | homozygous | |
| 9 | Fam 8 | female | 20 | 32 | White American | no | dHMN | | rapid worsening | intermediate | normal/normal | mild | homozygous | |
| 10 | Fam 9 | male | 12 | 15 | White American | no | CMT intermediate | walking difficulty | upper limb tremor | intermediate | reduced/normal | mild | homozygous | |
| 11 | Fam 10 | female | 12 | 23 | Mixed White and African American | no | CMT2 | walking difficulty | | intermediate | normal/reduced | mild | homozygous | |
| 12 | Fam 11 | male | 15 | 34 | White British | no | dHMN | unable to stand on toes | stress fractures | axonal | reduced/normal | mild | homozygous | |

FIG. 11

| # | Family | Sex | Age 1 | Age 2 | Ethnicity | Consang. | Diagnosis | Symptom | Other features | Type | Reflexes | Severity | Zygosity | Mutation |
|---|---|---|---|---|---|---|---|---|---|---|---|---|---|---|
| 13 | Fam 12 | male | 13 | 43 | White British | no | dHMN | unable to stand on toes | Left peroneal nerve mononeuropathy | axonal | reduced/normal | moderate | homozygous | |
| 14 | Fam 13 | male | 29 | 34 | White German | no | Complex CMT2 | walking difficulties | Complex spastic syndrome entailing mental retardation (since age 3), coarse facial features, bulky stature | axonal | not available /normal | mild | homozygous | c.458C>A; p.(Ala153Asp) (parents unavailable) |
| 15 | Fam 14 II-1 | male | 10 | 27 | White Austrian | no | CMT2 | walking difficulties | upper limb distal weakness and tremor | intermediate | reduced/not available | moderate | heterozygous (parents unavailable) | c.458C>A; p.(Ala153Asp) (parents unavailable) |
| 16 | Fam 14 II-2 | female | 20 | 36 | White Austrian | no | CMT2 | walking difficulties | | intermediate | reduced/not available | mild | heterozygous (parents unavailable) | |
| 17 | Fam 15 | female | 18 | 28 | Middle Eastern (Bedouin) Egyptian | no | dHMN | unable to stand on toes, unable to wear high heels | upper limb tremor | axonal | reduced/reduced | mild | homozygous | |
| 18 | Fam 16 | female | 15 | 55 | White British | no | dHMN | walking difficulties | | axonal | absent/normal | mild | homozygous | |
| 19 | Fam 17 | male | 12 | 23 | East Asian Singaporean | no | CMT intermediate | walking and running difficulties | | axonal | reduced/normal | moderate | homozygous | |
| 20 | Fam 18 II-1 | female | 12 | 20 | Middle Eastern Egyptian | yes | CMT2 | walking difficulties | burning pain in hands and feet | intermediate | normal/absent | moderate | homozygous | |
| 21 | Fam 18 II-2 | male | 15 | 17 | Middle Eastern Egyptian | yes | CMT2 | walking difficulties | | intermediate | normal/absent | moderate | homozygous | |
| 22 | Fam 19 II-1 | male | 40 | 70 | Middle Eastern Egyptian | yes | CMT2 | walking difficulties | | not available | not available | severe | homozygous | |
| 23 | Fam 19 II-2 | male | 29 | 39 | Middle Eastern Egyptian | yes | CMT2 | walking difficulties | | not available | not available | moderate | homozygous | |
| 24 | Fam 19 II-3 | male | 16 | 19 | Middle Eastern Egyptian | yes | CMT2 | walking difficulties | | not available | not available | mild | homozygous | |
| 25 | Fam 19 II-3 | male | 18 | 26 | Middle Eastern Kuwaiti | yes | CMT2 (motor predominant) | Difficulties running and jumping | | intermediate | normal/reduced | mild | homozygous | |

*FIG. 11 CONT.*

| # | Family | Sex | | | Ethnicity | Consang. | Phenotype | First symptom | Additional features | Neuropathy | Reflexes | Severity | Zygosity | Mutation |
|---|---|---|---|---|---|---|---|---|---|---|---|---|---|---|
| 26 | Fam 21 | female | 20 | 29 | White Italian | no | CMT2 (motor predominant) | walking difficulties | | axonal | normal/reduced | moderate | homozygous | |
| 27 | Fam 22 | male | 15 | 31 | White Italian | yes | dHMN | distal atrophy of lower limbs | | axonal | normal/normal | mild | homozygous | |
| | | | | | | | | | epilepsy, vascular encephalopathy, upper limb tremor, scoliosis. Has a normal sural nerve biopsy | | | | | |
| 28 | Fam 23 II-1 | male | 25 | 52 | White Italian | no | dHMN | walking difficulties | | axonal | normal/normal | mild | homozygous | |
| 29 | Fam 23 II-2 | female | 20 | 45 | White Italian | yes | CMT2 | pes cavus | | axonal | reduced/reduced | mild | homozygous | |
| 30 | Fam 24 | female | 20 | 42 | White Italian | no | dHMN | walking difficulties | brisk reflexes | axonal | normal/normal | moderate | homozygous | |
| 31 | Fam 25 | male | 14 | 46 | White Italian | no | dHMN | walking difficulties | | axonal | normal/normal | mild | homozygous | |
| 32 | Fam 26 | male | 12 | 41 | White Italian | no | CMT2 (motor predominant) | walking difficulties | split hand | axonal | reduced/normal | moderate | homozygous | |
| 33 | Fam 27 | male | 13 | 28 | White Italian | no | dHMN | walking difficulties | scoliosis, raised CK | axonal | normal/normal | moderate | homozygous | |
| 34 | Fam 28 II-1 | female | 40 | 48 | White Italian | yes | dHMN | walking difficulties | brisk reflexes | axonal | normal/normal | mild | homozygous | |
| 35 | Fam 28 II-2 | female | 20 | 52 | White Italian | yes | dHMN | walking difficulties | brisk reflexes | axonal | normal/normal | mild | homozygous | c.964G>A; p.(Val322Ile) (maternal) |
| 36 | Fam 29 | male | 2 | 10 | White Italian | no | CMT2 | retarded developmental milestone | scoliosis | axonal | absent/absent | moderate | heterozygous (absent in the mother, father unavailable) | c.316_425+165del (maternal) |
| 37 | Fam 30 | male | 15 | 18 | White Italian | no | CMT2 | falls | scoliosis | intermediate | reduced/absent | mild | heterozygous (paternal) | |
| 38 | Fam 31 | male | 30 | 42 | White Italian | no | CMT2 | walking difficulties | scoliosis | intermediate | reduced/absent | moderate | homozygous | |
| 39 | Fam 32 | male | 18 | 29 | White Italian | no | dHMN | walking difficulties, cramps | raised CK | axonal | normal/normal | mild | heterozygous (mother) | c.28C>T; p.Leu10Phe) (de novo) |
| 40 | Fam 33 | male | 15 | 60 | White Italian | no | CMT2 (motor predominant) | falls | mild hearing loss | axonal | normal/reduced | moderate | heterozygous (parents unavailable) | c.895C>T; p.(Arg299Ter) |
| 41 | Fam 34 | male | 25 | 36 | White American | no | CMT intermediate | distal atrophy of lower limbs | | intermediate | normal/normal | mild | homozygous | |
| | Fam 35 | | | | Mixed, Native American (Alaska) and White | | | | | | | | | |
| 42 | | male | 12 | 16 | White American | no | dHMN | running difficulties | | axonal | reduced/normal | mild | homozygous | |

*FIG. 11 CONT.*

| | | | | East Asian (Han) Chinese | sporadic | CMT2 (motor predominant) | foot drop and walking difficulties | axonal | normal/normal | mild | homozygous |
|---|---|---|---|---|---|---|---|---|---|---|---|
| 43 | Fam 36 | male | 10 | 29 | | | | | | | | |
| 44 | Fam 37 | male | 10 | 24 | East Asian (Han) Chinese | sporadic | CMT2 | walking difficulties | axonal | normal/reduced | mild | homozygous |
| 45 | Fam 38 | male | 16 | 26 | East Asian (Han) Chinese | sporadic | CMT2 | walking difficulties | axonal | normal/reduced | mild | homozygous |

*FIG. 11 CONT.*

|  | N=45 |
|---|---|
| Male | 32 (71%) |
| Age of onset | 17 ± 8 (2-40) |
| Age at examination | 34 ± 14 (10-70) |
| Family history of neuropathy | 13 (29%) |
| CMT subtype | |
| CMT2 | 23 (51%) |
| dHMN | 18 (40%) |
| CMT intermediate | 4 (9%) |
| Foot deformities | 31 (69%) |
| Upper limb weakness | |
| Proximal muscle groups | 0/44 (0%) |
| Distal muscle groups | 26/44 (59%) |
| Lower limb weakness | |
| Proximal muscle groups | 2/44 (5%) |
| Distal muscle groups | 43/44 (98%) |
| Prominent involvement of foot plantar flexion | 15/37 (41%) |
| Reduced vibratory sensation | 17/40 (42%) |
| Reduced pinprick superficial sensation | 13/39 (33%) |
| Disease severity | |
| Mild | 30 (67%) |
| Moderate | 14 (31%) |
| Severe | 1 (2%) |
| Use of ankle-foot orthoses (AFOs) | 19 (42%) |
| Other walking aids | 2 (4%) |
| Nerve conduction study | |
| Reduced motor conduction velocity | 11/42 (26%) |
| Reduced sensory action potentials | 26/40 (65%) |

FIG. 12

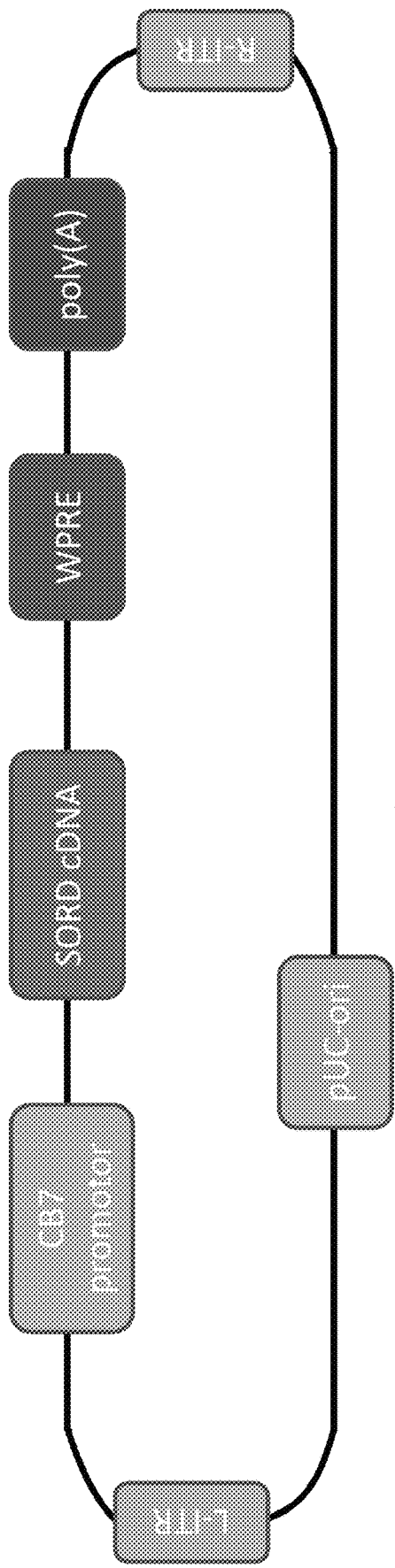

*FIG. 14A* atggcggcggcggccaagcccaacaacctttccctggtggtgcacggaccgggggactttgcctggcctggagaactatcctatccctgaaccaggcccaaatgaggtcttgctgaggatgcattctgttggaatctgtgctcag
atgtccactactggagtatggtcgaattggtgaatttattgtgaaaaagcccatggtgctgggacatgaagcttcgtgggatcatcgaacagtcgaaaaagtggatcatcgtaaaaccaggtatcgtgttgccatcga
gcctggtgctccccgagaaatgatgaaattctgcaagatgggcgccctacttgtccatcctctgtgccacgcccccgatacgggaacctgtcctataagcacaatcagccttgttacaagctt
cctgacaatgtcacctttgaggaagggccgtcaagtagtagtcagctcggaagtcctgagctgtgactgatggtgtgctaccggttgtctgctaccgatcgtcgatcagctccaaaagcaagcagaagattggtgacttcctccagatctccagattccagatctccagaacgagagccctcaggaaatgccaggaaagtagaag
gtcagtcgggtgcaagccgaagtcaccatcgagtgcgaaggccagaggcctcatccaggcagggcatcaccgattttgatgcttgggctggcttgcctccactgtcgatgaaccgccgatgaccacgtacccctact
gcatgcagccatccggagagttgatatctcaaggggcgtgtttgaaatcatgtcaagtgtgacccagtgaccagtgaaaatcatgtcgaaatgctgaaatccctga
aggcctttgaaacatttaaaaaggattgggggtgtgaaaatcatgtcaagtgtgacccagtgaccagtgaaaatcatgtcgaaatgctgaaatccctga

*FIG. 14B* (SEQ ID NO: 45)

MAAAAKPNNLSLVVHGPGDLRLENYPIPEPGPNEVLLRMHSVGICGSDVHYWEYGRIGNFIVKKPMVLGHEASGTVEKVGSSVKHLKPGDRVAIEPGAPRENDEFCKMGRYN
LSPSIFFCATPPDDGNLCRFYKHNAAFCYKLPDNVTFEEGALIEPLSVGIHACRRGGVTLGHKVLVCGAGPIGMVTLLVAKAMGAAQVVTDLSATRLSKAKEIGADLVLQJSKES
PQEIARKVEGQLGCKPEVTIECTGAEASIQAGIYATRSGGNLVLVGLGSEMTTVPLLHAAIREVDIKGVFRYCNTWPVAISMLASKSVNVKPLVTHRFPLEKALEAFETFKKGLGLKI
MLKCDPSDQNP

*FIG. 14C* (SEQ ID NO: 46)

AR 1A
G*T*T*T*A*A*G#*A*T*C*A*T*C*T*C*C*A*C*C*T
[SEQ ID NO: 22]
AR-S 1A
T*A*T*T*A*C*A#*G*C*T*A*C*A*T*C*C*T*G*T*C
[SEQ ID NO: 47]
FIG. 15A
Underlined = MOE     * = PS     G# or A# = 2' – O – methyl
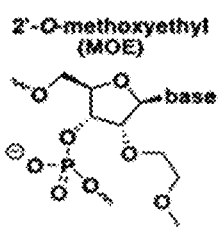
2'-O-methoxyethyl (MOE)
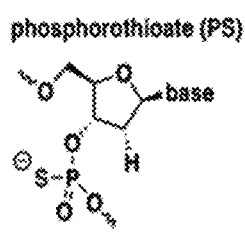
phosphorothioate (PS)
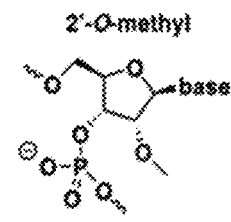
2'-O-methyl
FIG. 15B
(C)
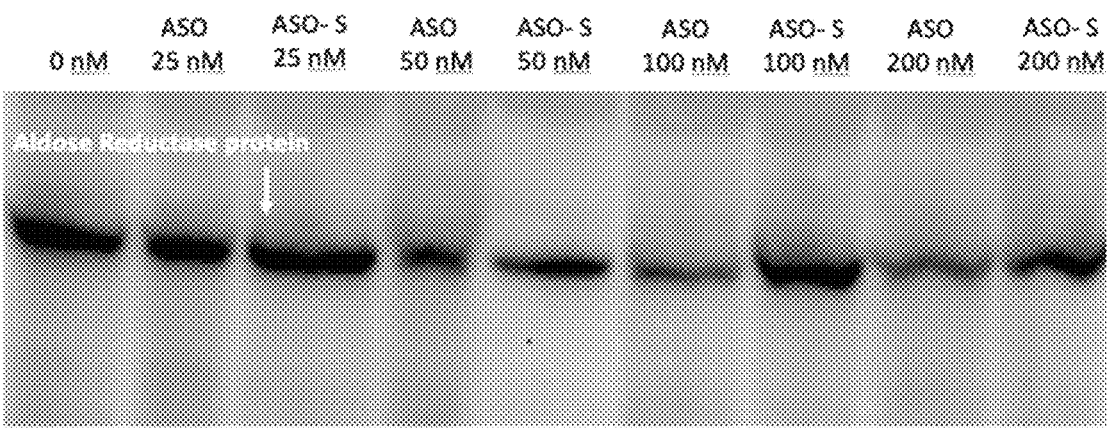
FIG. 15C

ASO sequences and corresponding target sites in *Homo sapiens* aldo-keto reductase family 1 member B (AKR1B1), exon targets only

| Rank | SEQ ID NO: | target sequence (5p --> 3p) | antisense oligo (5p --> 3p) | SEQ ID NO: | GC content | oligo binding energy (kcal/mol) |
|---|---|---|---|---|---|---|
| 1 | 49 | UCGCAGCCAAGCACAAUAAA | TTTATTGTGCTTGGCTGCGA | 50 | 45.00% | -16.3 |
| 2 | 51 | GCAGCCAAGCACAAUAAAAC | GTTTTATTGTGCTTGGCTGC | 52 | 45.00% | -16.3 |
| 3 | 53 | GAUCGCAGCCAAGCACAAUA | TATTGTGCTTGGCTGCGATC | 54 | 50.00% | -16.2 |
| 4 | 55 | AUCGCAGCCAAGCACAAUAA | TTATTGTGCTTGGCTGCGAT | 56 | 45.00% | -16.1 |
| 5 | 57 | CGCAGCCAAGCACAAUAAAA | TTTTATTGTGCTTGGCTGCG | 58 | 45.00% | -15.9 |
| 6 | 59 | GCCAAGCACAAUAAAACUAC | GTAGTTTTATTGTGCTTGGC | 60 | 40.00% | -15.7 |
| 7 | 61 | CGAUCGCAGCCAAGCACAAU | ATTGTGCTTGGCTGCGATCG | 62 | 55.00% | -15.6 |
| 8 | 63 | AGCACAAUAAAACUACAGCC | GGCTGTAGTTTTATTGTGCT | 64 | 40.00% | -15.2 |
| 9 | 65 | CAGCCAAGCACAAUAAAACU | AGTTTTATTGTGCTTGGCTG | 66 | 40.00% | -14.8 |
| 10 | 67 | GCGAUCGCAGCCAAGCACAA | TTGTGCTTGGCTGCGATCGC | 68 | 60.00% | -14.7 |
| 11 | 69 | GCACAAUAAAACUACAGCCC | GGGCTGTAGTTTTATTGTGC | 70 | 45.00% | -13.6 |
| 12 | 71 | AACCAGAUUGAGUGCCACCC | GGGTGGCACTCAATCTGGTT | 72 | 55.00% | -13 |
| 13 | 73 | ACCAGAUUGAGUGCCACCCA | TGGGTGGCACTCAATCTGGT | 74 | 55.00% | -13 |
| 14 | 75 | ACCUCCCACAAGGAUUACCC | GGGTAATCCTTGTGGGAGGT | 76 | 55.00% | -12.7 |
| 15 | 77 | CCUCCCACAAGGAUUACCCC | GGGGTAATCCTTGTGGGAGG | 78 | 60.00% | -12.6 |
| 16 | 79 | ACAACCUGAAUACCCUUUUC | GAAAAGGGTATTCAGGTTGT | 80 | 40.00% | -12.3 |
| 17 | 81 | CUCCCACAAGGAUUACCCCU | AGGGGTAATCCTTGTGGGAG | 82 | 55.00% | -12.2 |
| 18 | 83 | CCAGAUUGAGUGCCACCCAU | ATGGGTGGCACTCAATCTGG | 84 | 55.00% | -12.1 |
| 19 | 85 | CAACCUGAAUACCCUUUUCU | AGAAAAGGGTATTCAGGTTG | 86 | 40.00% | -12.1 |
| 20 | 87 | AGUACAACCUGAAUACCCUU | AAGGGTATTCAGGTTGTACT | 88 | 40.00% | -11.9 |
| 21 | 89 | GUACAACCUGAAUACCCUUU | AAAGGGTATTCAGGTTGTAC | 90 | 40.00% | -11.9 |
| 22 | 91 | AAGGCGAUCGCAGCCAAGCA | TGCTTGGCTGCGATCGCCTT | 92 | 60.00% | -11.8 |
| 23 | 93 | UCCCACAAGGAUUACCCCUU | AAGGGGTAATCCTTGTGGGA | 94 | 50.00% | -11.8 |

*FIG. 16*

| # | RNA sequence | # | DNA sequence | % | ΔG |
|---|---|---|---|---|---|
| 24 | AAGUACAACCUGAAUACCCU | 95 | AGGGTATTCAGGTTGTACTT | 40.00% | -11.8 |
| 25 | AACCUGAAUACCCUUUUCUG | 97 | CAGAAAAGGGTATTCAGGTT | 40.00% | -11.8 |
| 26 | ACCUGAAUACCCUUUUCUGA | 99 | TCAGAAAGGGTATTCAGGT | 40.00% | -11.7 |
| 27 | UACCUCCCACAAGGAUUACC | 101 | GGTAATCCTTGTGGGAGGTA | 50.00% | -11.5 |
| 28 | AAAGUACAACCUGAAUACCC | 103 | GGGTATTCAGGTTGTACTTT | 40.00% | -11.5 |
| 29 | CCUGAAUACCCUUUUCUGAC | 105 | GTCAGAAAAGGGTATTCAGG | 45.00% | -11.5 |
| 30 | UAACCAGAUUGAGUGCCACC | 107 | GGTGGCACTCAATCTGGTTA | 50.00% | -11.2 |
| 31 | AUUGAGUGCCACCAUAUCU | 109 | AGATATGGTGGCACTCAAT | 45.00% | -11.2 |
| 32 | GUGCCACCAUAUCUCACUC | 111 | GAGTGAGATATGGGTGGCAC | 55.00% | -11.2 |
| 33 | UGCCACCAUAUCUCACUCA | 113 | TGAGTGAGATATGGGTGGCA | 50.00% | -11.2 |
| 34 | CACAAUAAAACUACAGCCA | 115 | TGGGCTGTAGTTTTATTGTG | 40.00% | -11.2 |
| 35 | CCCACAAGGAUUACCCCUUC | 117 | GAAGGGGTAATCCTTGTGGG | 55.00% | -11.2 |
| 36 | CUGAAUACCCUUUUCUGACC | 119 | GGTCAGAAAAGGGTATTCAG | 45.00% | -11.2 |
| 37 | GAUUGAGUGCCACCAUAUC | 121 | GATATGGTGGCACTCAATC | 50.00% | -11.1 |
| 38 | AGUGCCACCAUAUCUCACU | 123 | AGTGAGATATGGTGGCACT | 50.00% | -11.1 |
| 39 | GCCACCAUAUCUCACUCAG | 125 | CTGAGTGAGATATGGGTGGC | 55.00% | -11.1 |
| 40 | GAGUGCCACCAUAUCUCAC | 127 | GTGAGATATGGTGGCACTC | 55.00% | -11 |
| 41 | UGAAUACCCUUUUCUGACCA | 129 | TGGTCAGAAAAGGGTATTCA | 40.00% | -11 |
| 42 | UUGAGUGCCACCAUAUCUC | 131 | GAGATATGGTGGCACTCAA | 50.00% | -10.9 |
| 43 | UGAGUGCCACCAUAUCUCA | 133 | TGAGATATGGGTGGCACTCA | 50.00% | -10.9 |
| 44 | AGAUUGAGUGCCACCAUAU | 135 | ATATGGTGGCACTCAATCT | 45.00% | -10.8 |
| 45 | CCACCCAUAUCUCACUCAGG | 137 | CCTGAGTGAGATATGGGTGG | 55.00% | -10.8 |
| 46 | CAGAUUGAGUGCCACCAUA | 139 | TATGGTGGCACTCAATCTG | 50.00% | -10.7 |
| 47 | CCACAAGGAUUACCCCUUCC | 141 | GGAAGGGGTAATCCTTGTGG | 55.00% | -10.6 |
| 48 | GAAAUACAACCUGAAUACC | 143 | GGTATTCAGGTTGTACTTTC | 40.00% | -10.6 |
| 49 | GAAUACCCUUUUCUGACCAA | 145 | TTGGTCAGAAAAGGGTATTC | 40.00% | -10.5 |
| 50 | ACAAUAAAACUACAGCCCAG | 147 | CTGGGCTGTAGTTTTATTGT | 40.00% | -10.4 |
| 51 | GUACCUCCCACAAGGAUUAC | 149 | GTAATCCTTGTGGGAGGTAC | 50.00% | -10.3 |
| 52 | AAACAAACCUGGCUUGAAGU | 151 | ACTTCAAGCCAGGTTTGTTT | 40.00% | -10.1 |

FIG. 16 CONT.

| # | SEQ ID | RNA Sequence | SEQ ID | DNA Sequence | % GC | ΔG |
|---|---|---|---|---|---|---|
| 53 | 153 | UCAAGGGCGAUCGCAGCCAAG | 154 | CTTGGCTGCGATCGCCTTGA | 60.00% | -10.1 |
| 54 | 155 | AUGGCAAGCCGUCUCCUGCU | 156 | AGCAGGAGACGGCTTGCCAT | 60.00% | -10 |
| 55 | 157 | GAUCUUAAACAAACCUGGCU | 158 | AGCCAGGTTTGTTTAAGATC | 40.00% | -10 |
| 56 | 159 | UGAUCUUAAACAAACCUGGC | 160 | GCCAGGTTTGTTTAAGATCA | 40.00% | -9.9 |
| 57 | 161 | UAAACAAACCUGGCUUGAAG | 162 | CTTCAAGCCAGGTTTGTTTA | 40.00% | -9.8 |
| 58 | 163 | AACAAACCUGGCUUGAAGUA | 164 | TACTTCAAGCCAGGTTTGTT | 40.00% | -9.8 |
| 59 | 165 | CUCAGCAGUGGGACAGCAAC | 166 | GTTGCTGTCCCACTGCTGAG | 60.00% | -9.8 |
| 60 | 167 | UCAGCAGUGGGACAGCAACC | 168 | GGTTGCTGTCCCACTGCTGA | 60.00% | -9.8 |
| 61 | 169 | CAGCAGUGGGACAGCAACCU | 170 | AGGTTGCTGTCCCACTGCTG | 60.00% | -9.8 |
| 62 | 171 | AGCAGUGGGACAGCAACCUG | 172 | CAGGTTGCTGTCCCACTGCT | 60.00% | -9.8 |
| 63 | 173 | GCAGUGGGACAGCAACCUGU | 174 | ACAGGTTGCTGTCCCACTGC | 60.00% | -9.7 |
| 64 | 175 | CAGUGGGACAGCAACCUGUA | 176 | TACAGGTTGCTGTCCCACTG | 55.00% | -9.7 |
| 65 | 177 | AGUGGGACAGCAACCUGUAG | 178 | CTACAGGTTGCTGTCCCACT | 55.00% | -9.7 |
| 66 | 179 | UGUACCUCCCACAAGGAUUA | 180 | TAATCCTTGTGGGAGGTACA | 45.00% | -9.6 |
| 67 | 181 | AAGUGACCUAUACCUGUGUU | 182 | AACACAGGTATAGGTCACTT | 40.00% | -9.6 |
| 68 | 183 | GUGGGACAGCAACCUGUAGA | 184 | TCTACAGGTTGCTGTCCCAC | 55.00% | -9.6 |
| 69 | 185 | UAGUGCCACUACUAACGGUU | 186 | AACCGTTAGTAGTGGCACTA | 50.00% | -9.6 |
| 70 | 187 | AGUGCCACUACUAACGGUUG | 188 | CAACCGTTAGTAGTGGCACT | 50.00% | -9.6 |
| 71 | 189 | AGGUGGAGAUGAUCUUAAAC | 190 | GTTTAAGATCATCTCCACCT | 40.00% | -9.5 |
| 72 | 191 | UGGGACAGCAACCUGUAGAG | 192 | CTCTACAGGTTGCTGTCCCA | 55.00% | -9.5 |
| 73 | 193 | AUAGUGCCACUAACGGUUGA | 194 | TCAACCGTTAGTGGCACTAT | 45.00% | -9.5 |
| 74 | 195 | CAAGUGACCUAUACCUGUGU | 196 | ACACAGGTATAGGTCACTTG | 45.00% | -9.4 |
| 75 | 197 | AGUGACCUAUACCUGUGUUU | 198 | AAACACAGGTATAGGTCACT | 40.00% | -9.4 |
| 76 | 199 | GCAAGCCGUCUCCUGCUCAA | 200 | TTGAGCAGGAGACGGCTTGC | 60.00% | -9.3 |
| 77 | 201 | CAAGCCGUCUCCUGCUCAAC | 202 | GTTGAGCAGGAGACGGCTTG | 60.00% | -9.3 |
| 78 | 203 | AAGCCGUCUCCUGCUCAACA | 204 | TGTTGAGCAGGAGACGGCTT | 55.00% | -9.3 |
| 79 | 205 | UCUUAAACAAACCUGGCUUG | 206 | CAAGCCAGGTTTGTTTAAGA | 40.00% | -9.3 |
| 80 | 207 | UCUGUGACACCAGAACGCAU | 208 | ATGCGTTCTGGTGTCACAGA | 50.00% | -9.3 |
| 81 | 209 | CUGUGACACCAGAACGCAUU | 210 | AATGCGTTCTGGTGTCACAG | 50.00% | -9.3 |

*FIG. 16 CONT.*

| # | SEQ ID | RNA Sequence | SEQ ID | DNA Sequence | % | Value |
|---|---|---|---|---|---|---|
| 82 | 211 | UGUGACACCAGAAACGCAUUG | 212 | CAATGCGTTTCTGGTGTCACA | 50.00% | -9.3 |
| 83 | 213 | AACUUCAACCAUCUCCAGGU | 214 | ACCTGGAGATGGTTGAAGTT | 45.00% | -9.2 |
| 84 | 215 | ACAAACCUGGCUUGAAGUAU | 216 | ATACTTCAAGCCAGGTTTGT | 40.00% | -9.2 |
| 85 | 217 | UUAACCAGAUUGAGUGCCAC | 218 | GTGGCACTCAATCTGGTTAA | 45.00% | -9.2 |
| 86 | 219 | GUGACACCAGAAACGCAUUGC | 220 | GCAATGCGTTTCTGGTGTCAC | 55.00% | -9.2 |
| 87 | 221 | UGACACCAGAAACGCAUUGCU | 222 | AGCAATGCGTTTCTGGTGTCA | 50.00% | -9.1 |
| 88 | 223 | AUUACCCUUCCAUGAAGAG | 224 | CTCTTCATGGAAGGGTAAT | 45.00% | -9.1 |
| 89 | 225 | GGGACAGCAACCUGUAGAGU | 226 | ACTCTACAGGTTGCTGTCCC | 55.00% | -9.1 |
| 90 | 227 | AUACCCUUUUCUGACCAAAG | 228 | CTTTGGTCAGAAAAGGGTAT | 40.00% | -9.1 |
| 91 | 229 | AUCAAGGCGAUCGCAGCCAA | 230 | TTGGCTGCGATCGCCTTGAT | 55.00% | -9 |
| 92 | 231 | AGUCUGUGACACCAGAACGC | 232 | GCGTTCTGGTGTCACAGACT | 55.00% | -9 |
| 93 | 233 | CUGUACCUCCCACAAGGAUU | 234 | AATCCTTGTGGGAGGTACAG | 50.00% | -9 |
| 94 | 235 | CACAAGGAUUACCCUUCCA | 236 | TGGAAGGGTAATCCTTGTG | 50.00% | -9 |
| 95 | 237 | GAUUACCCCUUCCAUGAAGA | 238 | TCTTCATGGAAGGGGTAATC | 45.00% | -9 |
| 96 | 239 | UUACCCCUUCCAUGAAGAGU | 240 | ACTCTTCATGGAAGGGGTAA | 45.00% | -9 |
| 97 | 241 | UACCCCUUCCAUGAAGAGUU | 242 | AACTCTTCATGGAAGGGGTA | 45.00% | -9 |
| 98 | 243 | CACCCAUAUCUCACUCAGGA | 244 | TCCTGAGTGAGATATGGGTG | 50.00% | -8.9 |
| 99 | 245 | GGAUUACCCCUUCCAUGAAG | 246 | CTTCATGGAAGGGGTAATCC | 50.00% | -8.9 |
| 100 | 247 | ACUCAGCAGUGGGACAGCAA | 248 | TTGCTGTCCCACTGCTGAGT | 55.00% | -8.9 |
| 101 | 249 | AAGCCUGCAGUUAACCAGAU | 250 | ATCTGGTTAACTGCAGGCTT | 45.00% | -8.8 |
| 102 | 251 | GUCUGUGACACCAGAACGCA | 252 | TGCGTTCTGGTGTCACAGAC | 55.00% | -8.8 |
| 103 | 253 | GCUGUACCUCCCACAAGGAU | 254 | ATCCTTGTGGGAGGTACAGC | 55.00% | -8.8 |
| 104 | 255 | AGGAUUACCCCUUCCAUGAA | 256 | TTCATGGAAGGGGTAATCCT | 45.00% | -8.8 |
| 105 | 257 | AGCCUGCAGUUAACCAGAUU | 258 | AATCTGGTTAACTGCAGGCT | 45.00% | -8.7 |
| 106 | 259 | CCAAGUGACCUAUACCUGUG | 260 | CACAGGTATAGGTCACTTGG | 50.00% | -8.7 |
| 107 | 261 | ACUUCAACCAUCUCCAGGUG | 262 | CACCTGGAGATGGTTGAAGT | 50.00% | -8.6 |
| 108 | 263 | UUGAGCUGUACCUCCCACAA | 264 | TTGTGGGAGGTACAGCTCAA | 50.00% | -8.6 |
| 109 | 265 | UGAGCUGUACCUCCCACAAG | 266 | CTTGTGGGAGGTACAGCTCA | 55.00% | -8.6 |
| 110 | 267 | GAGCUGUACCUCCCACAAGG | 268 | CCTTGTGGGAGGTACAGCTC | 60.00% | -8.6 |

*FIG. 16 CONT.*

| | | | | | |
|---|---|---|---|---|---|
| 111 | 269 | AGCUGUACCUCCCACAAGGA | 270 | TCCTTGTGGGAGGTACAGCT | 55.00% | -8.6 |
| 112 | 271 | ACCCCUUCCAUGAAGAGUUU | 272 | AAACTCTTCATGGAAGGGGT | 45.00% | -8.6 |
| 113 | 273 | GGAAAGUACAACCUGAAUAC | 274 | GTATTCAGGTTGTACTTTCC | 40.00% | -8.6 |
| 114 | 275 | GGAAUUUUCCCAUUGGAUG | 276 | CATCCAATGGGAAAAATTCC | 40.00% | -8.5 |
| 115 | 277 | GGUGGAGAUGAUCUUAAACA | 278 | TGTTTAAGATCATCTCCACC | 40.00% | -8.5 |
| 116 | 279 | GCCUGCAGUUAACCAGAUUG | 280 | CAATCTGGTTAACTGCAGGC | 50.00% | -8.5 |
| 117 | 281 | ACAAGGAUUACCCUUCCAU | 282 | ATGGAAGGGTAATCCTTGT | 45.00% | -8.5 |
| 118 | 283 | AGCCGUCCUGCUCUCAACAA | 284 | TTGTTGAGCAGGAGACGGCT | 55.00% | -8.4 |
| 119 | 285 | AUUGGAUGAGUCGGGCAAUG | 286 | CATTGCCCGACTCATCCAAT | 50.00% | -8.4 |
| 120 | 287 | UAAGCCUGCAGUUAACCAGA | 288 | TCTGGTTAACTGCAGGCTTA | 45.00% | -8.4 |
| 121 | 289 | CCCAAGUCUGUGACACCAG | 290 | CTGGTGTCACAGACTTGGGG | 60.00% | -8.4 |
| 122 | 291 | GUGACCUAUACCUGUGUUUC | 292 | GAAACACAGGTATAGGTCAC | 45.00% | -8.4 |
| 123 | 293 | GGACAGCAACCUGUAGAGUG | 294 | CACTCTACAGGTTGCTGTCC | 55.00% | -8.4 |
| 124 | 295 | CUUAAACAAACCUGGCUUGA | 296 | TCAAGCCAGGTTTGTTTAAG | 40.00% | -8.3 |
| 125 | 297 | CAAUAAAACUACAGCCCAGG | 298 | CCTGGGCTGTAGTTTTATTG | 45.00% | -8.3 |
| 126 | 299 | AAGCUGUGACACCAGAACG | 300 | CGTTCTGGTGTCACAGACTT | 50.00% | -8.3 |
| 127 | 301 | GUUGAGCUGUACCUCCCACA | 302 | TGTGGGAGGTACAGCTCAAC | 55.00% | -8.3 |
| 128 | 303 | UACCCUUUUCUGACCAAAGA | 304 | TCTTTGGTCAGAAAAGGGTA | 40.00% | -8.3 |
| 129 | 305 | ACCCAUAUCUCACUCAGGAG | 306 | CTCCTGAGTGAGATATGGGT | 50.00% | -8.2 |
| 130 | 307 | AUCCCAAGUCUGUGACACC | 308 | GGTGTCACAGACTTGGGAT | 55.00% | -8.2 |
| 131 | 309 | UCCCCAAGUCUGUGACACCA | 310 | TGGTGTCACAGACTTGGGGA | 55.00% | -8.2 |
| 132 | 311 | CAAGGAUUACCCUUCCAUG | 312 | CATGGAAGGGTAATCCTTG | 50.00% | -8.2 |
| 133 | 313 | AAGGAUUACCCUUCCAUGA | 314 | TCATGGAAGGGTAATCCTT | 45.00% | -8.2 |
| 134 | 315 | AAUAGUGCCACUAACGGUUG | 316 | CAACCGTTAGTGGCACTATT | 45.00% | -8.2 |
| 135 | 317 | UUGGAUGAGUCGGGCAAUGU | 318 | ACATTGCCCGACTCATCCAA | 50.00% | -8.1 |
| 136 | 319 | CAACUUCAACCAUCUCCAGG | 320 | CCTGGAGATGGTTGAAGTTG | 50.00% | -8.1 |
| 137 | 321 | AUAAGCCUGCAGUUAACCAG | 322 | CTGGTTAACTGCAGGCTTAT | 45.00% | -8.1 |
| 138 | 323 | CCUGCAGUUAACCAGAUUGA | 324 | TCAATCTGGTTAACTGCAGG | 45.00% | -8.1 |
| 139 | 325 | GAUCCCAAGUCUGUGACAC | 326 | GTGTCACAGACTTGGGATC | 55.00% | -8.1 |

*FIG. 16 CONT.*

| | | | | | |
|---|---|---|---|---|---|
| 140 | 327 | UGUUGAGCUGUGUACCUCCCAC | 328 | GTGGGAGGTACAGCTCAACA | 55.00% | -8.1 |
| 141 | 329 | CACUCAGCAGUGGGACAGCA | 330 | TGCTGTCCCACTGCTGAGTG | 60.00% | -8.1 |
| 142 | 331 | UGGAUGAGUCGGGCAAUGUG | 332 | CACATTGCCCGACTCATCCA | 55.00% | -8 |
| 143 | 333 | AAUGUGGUUCCAGUGACAC | 334 | GTGTCACTGGGAACCACATT | 50.00% | -8 |
| 144 | 335 | GAUCAAGGCGAUCGGCAGCCA | 336 | TGGCTGCGATCGCCTTGATC | 60.00% | -8 |

*FIG. 16 CONT.*

ASO sites in homo sapiens aldo-keto reductase family 1 member B (AKR1B1), exon targets only

| Rank | SEQ ID NO: | target sequence (5p --> 3p) | antisense oligo (5p --> 3p) | SEQ ID NO: | GC content | average unpaired probability for target site nucleotides | binding site disruption energy (kcal/mol) |
|---|---|---|---|---|---|---|---|
| 1 | 337 | UCGCAGCCAAGCACAAUAAA | TTTATTGTGCTTGGCTGCGA | 338 | 45.00% | 0.819 | 8.6 |
| 2 | 339 | CGCAGCCAAGCACAAUAAAA | TTTTATTGTGCTTGGCTGCG | 340 | 45.00% | 0.818 | 9 |
| 3 | 341 | GCCCUUCUUUCUACCUGCU | AGCAGGGTAGAAAGAAGGGC | 342 | 55.00% | 0.735 | 9.9 |
| 4 | 343 | GACCUCACGGGCUAUUUAAA | TTTAAATAGCCCGTGAGGTC | 344 | 45.00% | 0.698 | 7.8 |
| 5 | 345 | UACCUCCACAAGGAUUACC | GGTAATCCTTGTGGGAGGTA | 346 | 50.00% | 0.694 | 7.3 |
| 6 | 347 | CCCUUCUUUCUACCUGCUG | CAGCAGGTAGAAAGAAGGG | 348 | 55.00% | 0.693 | 9.9 |
| 7 | 349 | ACCUCCACAAGGAUUACCC | GGGTAATCCTTGTGGGAGGT | 350 | 55.00% | 0.69 | 7.4 |
| 8 | 351 | ACCUCACGGGCUAUUUAAAG | CTTTAAATAGCCCGTGAGGT | 352 | 45.00% | 0.684 | 9.9 |
| 9 | 353 | AUUGAGUGCCACCAUAUCU | AGATATGGTGGCACTCAAT | 354 | 45.00% | 0.668 | 6.7 |
| 10 | 355 | GAUCUAAACAAACCUGGCU | AGCCAGGTTTGTTTAAGATC | 356 | 40.00% | 0.666 | 12 |
| 11 | 357 | UGAUCUAAACAAACCUGGC | GCCAGGTTTGTTTAAGATCA | 358 | 40.00% | 0.664 | 12.7 |
| 12 | 359 | AAGGCGAUCGCAGCAAGCA | TGCTTGCTGCGATCGCCTT | 360 | 60.00% | 0.663 | 9.4 |
| 13 | 361 | GAUUGAGUGCCACCAUAUC | GATATGGTGGCACTCAATC | 362 | 50.00% | 0.649 | 6.2 |
| 14 | 363 | CAGAUUGAGUGCCACCAUA | TATGGTGGCACTCAATCTG | 364 | 50.00% | 0.644 | 5.8 |
| 15 | 365 | CCAGAUUGAGUGCCACCAU | ATGGGTGGCACTCAATCTGG | 366 | 55.00% | 0.643 | 5.6 |
| 16 | 367 | UCAAGGCGAUCGCAGCAAG | CTTGCTGCGATCGCCTTGA | 368 | 60.00% | 0.639 | 10.1 |
| 17 | 369 | UAAACAAACCUGGCUUGAAG | CTTCAAGCCAGGTTTGTTTA | 370 | 40.00% | 0.636 | 9.3 |
| 18 | 371 | UUACCCCUUCCAUGAAGAGU | ACTCTTCATGGAAGGGGTAA | 372 | 45.00% | 0.633 | 8.6 |
| 19 | 373 | AAACAAACCUGGCUUGAAGU | ACTTCAAGCCAGGTTTGTTT | 374 | 40.00% | 0.631 | 8.5 |
| 20 | 375 | UACCCCUUCCAUGAAGAGUU | AACTCTTCATGGAAGGGGTA | 376 | 45.00% | 0.627 | 8.6 |

FIG. 17

ASO sites in homo sapiens aldo-keto reductase family 1 member B (AKR1B1), hg19_dna range=chr7:134127102-134143944 (intronic targets only)

| Rank | SEQ ID NO: | target sequence (5p --> 3p) | antisense oligo (5p --> 3p) | SEQ ID NO: | GC content | average unpaired probability for target site nucleotides | binding site disruption energy (kcal/mol) |
|---|---|---|---|---|---|---|---|
| 1 | 377 | AAUACAAAAAUUAGCCCGGC | GCCGGGCTAATTTTTGTATT | 378 | 40.00% | 0.859 | 7.5 |
| 2 | 379 | AAUACCAUCUCCUUCGGCC | GCCGAAGAGGAGATGGTATT | 380 | 50.00% | 0.818 | 3.8 |
| 3 | 381 | AAAUACCAUCUCCUUCGG | CCGAAGAGGAGATGGTATTT | 382 | 45.00% | 0.817 | 3.8 |
| 4 | 383 | AUACCAUCUCCUUCGGCU | AGCCGAAGAGGAGATGGTAT | 384 | 50.00% | 0.812 | 3.8 |
| 5 | 385 | CACUACCUUAUUCUUGUCU | AGACAAGAATAAGGGTAGTG | 386 | 40.00% | 0.812 | 4.3 |
| 6 | 387 | AUACAAAAAUUAGCCCGGCA | TGCCGGGCTAATTTTTGTAT | 388 | 40.00% | 0.811 | 7.6 |
| 7 | 389 | UCACUACCUUAUUCUUGUC | GACAAGAATAAGGGTAGTGA | 390 | 40.00% | 0.805 | 3 |
| 8 | 391 | UACCAUCUCCUUCGGCUG | CAGCCGAAGAGGAGATGGTA | 392 | 55.00% | 0.802 | 4.1 |
| 9 | 393 | ACACCCAUUCAGUCAUUUG | CAAATGACTGAATGGGTGT | 394 | 40.00% | 0.795 | 0.5 |
| 10 | 395 | GACACCCAUUCAGUCAUUU | AAAATGACTGAATGGGTGTC | 396 | 40.00% | 0.787 | 1.9 |
| 11 | 397 | UCAUGAUAAUCUCCCAGAAC | GTTCTGGGAGATTATCATGA | 398 | 40.00% | 0.783 | 4 |
| 12 | 399 | CAGUUUAUCUUAUCGCUCCU | AGGAGCGATAAGATAAACTG | 400 | 40.00% | 0.783 | 10 |
| 13 | 401 | AGUUUAUCUUAUCGCUCCUC | GAGGAGCGATAAGATAAACT | 402 | 40.00% | 0.782 | 9.9 |
| 14 | 403 | ACCUCCCAAGGAGAUUACCC | GGGTAATCCTTGTGGGAGGT | 404 | 55.00% | 0.777 | 7.3 |
| 15 | 405 | CCUCCCAAGGAGAUUACCC | GGGTAATCCTTGTGGGAGG | 406 | 60.00% | 0.767 | 7.3 |
| 16 | 407 | CAUGAGGUCAGAAGAAUAGAG | CTCTATCTTCTGACCTCATG | 408 | 45.00% | 0.761 | 7.5 |
| 17 | 409 | CUUCAUGAUAAUCUCCCAGA | TCTGGGAGATTATCATGAAG | 410 | 40.00% | 0.759 | 1.6 |
| 18 | 411 | AUGAGGUCAGAAGAUAGA | TCTATCTTCTGACCTCAT | 412 | 40.00% | 0.757 | 8 |
| 19 | 413 | ACUGUUUCUCCUUUCUCCU | AGGAGAAAGGAGAAACAGT | 414 | 40.00% | 0.755 | 7.2 |
| 20 | 415 | UUCUCCUUUCUCCUGACAGC | GCTGTCAGGAGAAAGGAGAA | 416 | 50.00% | 0.753 | 7.2 |
| 21 | 417 | AGACCAGCCUCCUUUCCCU | AGGGAAAGGAGGCTGGGTCT | 418 | 60.00% | 0.751 | 10.9 |
| 22 | 419 | CCCUUAUUCUUGUCUGAGCU | AGCTCAGACAAGAATAAGGG | 420 | 45.00% | 0.75 | 3.4 |

FIG. 18

| | | | | | |
|---|---|---|---|---|---|
| 23 | 421 | CUCUCCCAUUCAUCCGUCUU | AAGACGGATGAATGGGAGAG | 50.00% | 0.749 | 5 |
| 24 | 423 | CAUGAUAAUCUCCCAGAACC | GGTTCTGGGAGATTATCATG | 45.00% | 0.747 | 8.5 |
| 25 | 425 | UCUCCCAUUCAUCCGUCUCU | AGACGGATGAATGGGAGAGA | 50.00% | 0.747 | 4.3 |
| 26 | 427 | CCUAUUCUGUCUGAGCUC | GAGCTCAGACAAGAATAAGG | 45.00% | 0.744 | 3.4 |
| 27 | 429 | UCUCUCACUACCUUAUUCU | AGAATAAGGGTAGTGAGAGA | 40.00% | 0.734 | 4.8 |
| 28 | 431 | CCUUUCUGCCCUCUCUGUC | GACAGAGAGGGCAAGAAAGG | 55.00% | 0.718 | -0.1 |
| 29 | 433 | CCAAUCUGUCCAUUCCAUUU | AAATGGAATGGACAGATTGG | 40.00% | 0.716 | 3.8 |
| 30 | 435 | CUCUCCCUUUAGUACUUCC | GGAAGTACTAAAGGAGAGAG | 45.00% | 0.716 | 5.6 |
| 31 | 437 | UCUCUCCUUUAGUACUUCCU | AGGAAGTACTAAAGGAGAGA | 40.00% | 0.715 | 4.6 |
| 32 | 439 | CCUGAGCCUGAUUAUCUGAA | TTCAGATAATCAGGCTCAGG | 45.00% | 0.709 | 2.7 |
| 33 | 441 | CCAUCUUUUGCCAUGAUCAC | GTGATCATGGCAAAAGATGG | 45.00% | 0.709 | 1.6 |
| 34 | 443 | UUUCCAUCUUUUGCCAUG | CATGGCAAAAGATGGAGAAA | 40.00% | 0.708 | 2.3 |
| 35 | 445 | GCCAAUCUGUCCAUUCCAUU | AATGGAATGGACAGATTGGC | 45.00% | 0.708 | 3.8 |
| 36 | 447 | UCCAUCUUUUGCCAUGAUCA | TGATCATGGCAAAAGATGGA | 40.00% | 0.707 | 1.6 |
| 37 | 449 | CUGAGCCUGAUUAUCUGAAA | TTTCAGATAATCAGGCTCAG | 40.00% | 0.706 | 3 |
| 38 | 451 | CUUCUUGUGACCUCUCUUGCA | TGCAAGAGGTCACGAAGAAG | 50.00% | 0.696 | 5.3 |
| 39 | 453 | AUUGACUUCCCAAACAACA | TGTTGTTTGGGAAGTCAAT | 40.00% | 0.691 | 13 |
| 40 | 455 | CUAGAAAAACCUCUCACAAC | GTTGTGAGAGGTTTTCTAG | 40.00% | 0.688 | 5.3 |
| 41 | 457 | UUGACUUCCCAAACAACAG | CTGTTGTTTGGGAAGTCAA | 45.00% | 0.688 | 13.1 |
| 42 | 459 | UAGCCUGAGCCUGAUUAUCU | AGATAATCAGGCTCAGGCTA | 45.00% | 0.686 | 2.9 |
| 43 | 461 | ACGUAUCCAGUCACCGGCCAU | ATGGCCGTGACTGGATACGTT | 55.00% | 0.684 | 8.3 |
| 44 | 463 | ACACUCAAUACAGCUACACU | AGTGTAGCTGTATTGAGTGT | 40.00% | 0.68 | 5.9 |
| 45 | 465 | GCUUCUUGUGACCUCUUGC | GCAAGAGGTCACGAAGAAGC | 55.00% | 0.677 | 6.6 |
| 46 | 467 | AUAGCCUGAGCCUGAUUAUC | GATAATCAGGCTCAGGCTAT | 45.00% | 0.676 | 2.5 |
| 47 | 469 | GUAACUAGCAAGACCUGUAA | TTACAGGTCTTGCTAGTTAC | 40.00% | 0.676 | 5.3 |
| 48 | 471 | AUAAGCAUCUCAAGAGCCGGUA | TACCGGCTTGAGATGCTTAT | 45.00% | 0.672 | 4.2 |
| 49 | 473 | AAACGUAUCACCCACGGCCA | TGGCCGTGGGTGATACGTTT | 55.00% | 0.672 | 8.7 |
| 50 | 475 | CCGUAGCUAGUUGAUAAUUC | GAATTATCAACTAGCTACGG | 40.00% | 0.67 | 6.8 |
| 51 | 477 | AUUUGUUUCUACCCCAGCUC | GAGCTGGGGTAGAAACAAAT | 45.00% | 0.67 | 7.5 |

*FIG. 18 CONT.*

| | | | | | |
|---|---|---|---|---|---|
| 52 | 479 | AAUAAGCAUCUCAGCCGGU | ACCGGCTTGAGATGCTTATT | 480 | 45.00% | 0.669 | 4.2 |
| 53 | 481 | UUUGUUUCUACCCAGCUCU | AGAGCTGGGGTAGAAACAAA | 482 | 45.00% | 0.669 | 7.6 |
| 54 | 483 | ACGUAUCACCCAGGCCAUA | TATGGCCTGGGTGATACGT | 484 | 55.00% | 0.669 | 9.4 |
| 55 | 485 | UAAAACCUCAACACCACACA | TGTGTGGTGTTGAGGTTTA | 486 | 40.00% | 0.668 | 6.7 |
| 56 | 487 | GUCCCUCUUAACCACACC | GGTGTGGGTTAAGAGGGGAC | 488 | 60.00% | 0.667 | 11.1 |
| 57 | 489 | GUCUCAGCUCCAGCCGUUU | AAACGGGCTGGAGCTGAGAC | 490 | 60.00% | 0.663 | 8.3 |
| 58 | 491 | AGUCUCAGCUCCAGCCCGUU | AACGGGCTGGAGCTGAGACT | 492 | 60.00% | 0.656 | 5.3 |
| 59 | 493 | AAAACCUCAACACCACACAG | CTGTGTGGTGTTGAGGTTTT | 494 | 45.00% | 0.65 | 8.6 |
| 60 | 495 | CCCGUAGCUAGUUGAUAAUU | AATTATCAACTAGCTACGGG | 496 | 40.00% | 0.644 | 8.9 |
| 61 | 497 | UAGUGUCCAUGUCUCCGUCU | AGACGGAGACATGGACACTA | 498 | 50.00% | 0.644 | 9.2 |
| 62 | 499 | CUCACAACCAUUCACAGCAU | ATGCTGTGAATGGTTGTGAG | 500 | 45.00% | 0.643 | 13.6 |
| 63 | 501 | ACAACCAUUCACAGCAUCAU | ATGATGCTGTGAATGGTTGT | 502 | 40.00% | 0.641 | 12.4 |
| 64 | 503 | GCAUUUUGUUAUUCUGUCCC | GGGACAGAATAACAAAATGC | 504 | 40.00% | 0.633 | 8.6 |
| 65 | 505 | UCCGUCUGACAGUCAGCU | AGCTGAGACTGTCAGACGGA | 506 | 55.00% | 0.632 | 9.5 |
| 66 | 507 | CAUUCCAUUUUGUGUCCUCU | AGAGGACACAAAATGGAATG | 508 | 40.00% | 0.631 | 9 |
| 67 | 509 | UUAGAGUCCCGUGCUGAUGA | TCATCAGCACGGGACTCTAA | 510 | 50.00% | 0.627 | 6.8 |
| 68 | 511 | GUUUUAUUGCACCACAGCAU | ATGCTGTGGTGCAATAAAAC | 512 | 40.00% | 0.626 | 6.1 |
| 69 | 513 | UAAGCAUCUCAAGCCGGUAG | CTACCGGCTTGAGATGCTTA | 514 | 50.00% | 0.624 | 6.5 |
| 70 | 515 | UGCCCCUCACAACCAUUCACA | TGTGAATGGTTGTGAGGGCA | 516 | 50.00% | 0.623 | 11.9 |
| 71 | 517 | UAUCACCACGGCCAUACAG | CTGTATGGCCGTGGGTGATA | 518 | 55.00% | 0.621 | 14.3 |
| 72 | 519 | AUGACACCAAGCUAAUUCC | GGAAATTAGCTTGGTGTCAT | 520 | 40.00% | 0.618 | 9 |
| 73 | 521 | UUAUUGCACCACAGCAUAUC | GATATGCTGTGGTGCAATAA | 522 | 40.00% | 0.616 | 6.4 |
| 74 | 523 | GCAUGGGCUCUUAGAUUAAU | ATTAATCTAAGAGCCCATGC | 524 | 40.00% | 0.616 | 9.9 |
| 75 | 525 | AUUCCAUUUUGUGUCCUCUG | CAGAGGACACAAAATGGAAT | 526 | 40.00% | 0.613 | 11.3 |
| 76 | 527 | GGCUAAUCUUUUUCUUCCC | GGGAAGAAAAAGATTAGCC | 528 | 40.00% | 0.601 | 14.3 |
| 77 | 528 | ACAGAUGCUCGACAGAAGAU | ATCTTCTGTCGAGCATCTGT | 530 | 45.00% | 0.6 | 7.2 |
| 78 | 531 | GAUGCUCGACAGAAGAUGUG | CACATCTTCTGTCGAGCATC | 532 | 50.00% | 0.599 | 8.6 |
| 79 | 533 | UUGUUUCCUCCAAAACUCC | GGAGTTTTTGGAGGAAACAA | 534 | 40.00% | 0.597 | 9.6 |
| 80 | 535 | GUACUUAACCUAUGUAGGCU | AGCCTACATAGGTTAAGTAC | 536 | 40.00% | 0.594 | 6.6 |

*FIG. 18 CONT.*

SEQUENCE LISTING

<160> NUMBER OF SEQ ID NOS: 557

<210> SEQ ID NO 1
<211> LENGTH: 5756
<212> TYPE: DNA
<213> ORGANISM: Artificial Sequence
<220> FEATURE:
<223> OTHER INFORMATION: Description of Artificial Sequence:
      Synthetic polynucleotide

<400> SEQUENCE: 1

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca accgtctagt tattaatagt aatcaattac     180
ggggtcatta gttcatagcc catatatgga gttccgcgtt acataactta cggtaaatgg     240
cccgcctggc tgaccgccca acgaccccccg cccattgacg tcaataatga cgtatgttcc     300
catagtaacg ccaataggga cttttccattg acgtcaatgg gtggagtatt tacggtaaac     360
tgcccacttg gcagtacatc aagtgtatca tatgccaagt acgccccta ttgacgtcaa     420 tgacggtaaa tggcccgcct ggcattatgc ccagtacatg accttatggg actttcctac     480
ttggcagtac atctacgtat tagtcatcgc tattaccatg gtgatgcggt tttggcagta     540
catcaatggg cgtggatagc ggtttgactc acggggattt ccaagtctcc accccattga     600
cgtcaatggg agtttgtttt ggcaccaaaa tcaacgggac tttccaaaat gtcgtaacaa     660
ctccgcccca ttgacgcaaa tgggcggtag gcgtgtacgg tgggaggtct atataagcag     720
agctcgttta gtgaaccgtc agatcgcctg gagacgccat ccacgctgtt tgacctcca     780 tagaagacac cgggaccgat ccagcctccg cggattcgaa tcccggccgg aacggtgca     840 ttggaacgcg gattcccgt gccaagagtg acgtaagtac cgcctataga gtctataggc     900
ccacaaaaaa tgctttcttc ttttaatata cttttttgtt tatcttattt ctaatacttt     960
ccctaatctc tttctttcag ggcaataatg atacaatgta tcatgcctct ttgcaccatt    1020
ctaaagaata acagtgataa tttctgggtt aaggcaatag caatatttct gcatataaat    1080
atttctgcat ataaattgta actgatgtaa gaggtttcat attgctaata gcagctacaa    1140
```

```
tccagctacc attctgcttt tattttatgg ttgggataag gctggattat tctgagtcca    1200
agctaggccc ttttgctaat catgttcata cctcttatct tcctcccaca gctcctgggc    1260
aacgtgctgg tctgtgtgct ggcccatcac tttggcaaag aattgggatt cgaacatcga    1320
tccgaggaga tctgccgccg cgatcgccgg cgcgccatgg cggcggcggc caagcccaac    1380
aacctttccc tggtggtgca cggaccgggg gacttgcgcc tggagaacta tcctatccct    1440
gaaccaggcc caaatgaggt cttgctgagg atgcattctg ttggaatctg tggctcagat    1500
gtccactact gggagtatgg tcgaattggg aattttattg tgaaaaagcc catggtgctg    1560
ggacatgaag cttcgggaac agtcgaaaaa gtgggatcat cggtaaagca cctaaaacca    1620
ggtgatcgtg ttgccatcga gcctggtgct ccccgagaaa atgatgaatt ctgcaagatg    1680
ggccgataca atctgtcacc ttccatcttc tctgtgcca cgcccccga tgacgggaac     1740 ctctgccggt tctataagca caatgcagcc ttttgttaca gcttcctga caatgtcacc     1800 tttgaggaag gcgccctgat cgagccactt tctgtgggga tccatgcctg caggagaggc    1860
ggagttaccc tgggacacaa ggtccttgtg tgtggagctg ggccaatcgg gatggtcact    1920
ttgctcgtgg ccaaagcaat gggagcagct caagtagtgg tgactgatct gtctgctacc    1980
cgattgtcca aagccaagga gatttgggct gatttagtcc tccagatctc caaggagagc    2040
cctcaggaaa tcgccaggaa agtagaaggt cagctggggt gcaagccgga agtcaccatc    2100
gagtgcacgg gggcagaggc ctccatccag gcgggcatct acgccactcg ctctggtggg    2160
aacctcgtgc ttgtggggct gggctctgag atgaccaccg taccccact gcatgcagcc    2220 atccggggagg tggatatcaa gggcgtgttt cgatactgca acacgtggcc agtggcgatt    2280
tcgatgcttg cgtccaagtc tgtgaatgta aaacccctcg tcacccatag gtttcctctg    2340
gagaaagctc tggaggcctt tgaaacattt aaaaagggat tggggttgaa aatcatgctc    2400
aagtgtgacc ccagtgacca gaatccctga agatctcaag cttaactagc tagcggaccg    2460
acgcgtacgc ggccgctcgt ttaaacggcc ggcggatct acgggtggca tccctgtgac     2520
ccctccccag tgcctctcct ggccctggaa gttgccactc cagtgcccac cagccttgtc    2580
ctaataaaat taagttgcat cattttgtct gactaggtgt ccttctataa tattatgggg    2640 tggaggggg tggtatggag caaggggcaa gttgggaaga caacctgtag ggcctgcggg    2700
gtctattggg aaccaagctg gagtgcagtg gcacaatctt ggctcactgc aatctccgcc    2760
tcctgggttc aagcgattct cctgcctcag cctcccgagt tgttgggatt ccaggcatgc    2820
atgaccaggc tcagctaatt tttgtttttt tggtagagac ggggtttcac catattggcc    2880
aggctggtct ccaactccta atctcaggtg atctaccac cttggcctcc caaattgctg    2940
ggattacagg cgtgaaccac tgctcccttc cctgtcctc tgattttgta ggtaaccacg     3000
tgcggaccga gcggccgcag gaacccctag tgatggagtt ggccactccc tctctgcgcg    3060
ctcgctcgct cactgaggcc gggcgaccaa aggtcgcccg acgcccgggc tttgcccggg    3120
cggcctcagt gagcgagcga gcgcgcagct gcctgcaggg cgcctgatg cggtattttc     3180 tccttacgca tctgtgcggt atttcacacc gcatacgtca aagcaaccat agtacgcgcc    3240
ctgtagcggc gcattaagcg cggcgggtgt ggtggttacg cgcagcgtga ccgctacact    3300
tgccagcgcc ctagcgcccg ctcctttcgc tttcttccct tcctttctcg ccacgttcgc    3360
cggctttccc cgtcaagctc taaatcgggg gctcccttta gggttccgat ttagtgcttt    3420
acggcacctc gaccccaaaa aacttgattt gggtgatggt tcacgtagtg gccatcgcc     3480 ctgatagacg gttttttcgcc ctttgacgtt ggagtccacg ttctttaata gtggactctt    3540
```

```
gttccaaact ggaacaacac tcaactctat ctcgggctat tcttttgatt tataagggat    3600
tttgccgatt tcggtctatt ggttaaaaaa tgagctgatt taacaaaaat ttaacgcgaa    3660
ttttaacaaa atattaacgt ttacaatttt atggtgcact ctcagtacaa tctgctctga    3720
tgccgcatag ttaagccagc cccgacaccc gccaacaccc gctgacgcgc cctgacgggc    3780
ttgtctgctc ccggcatccg cttacagaca agctgtgacc gtctccggga gctgcatgtg    3840
tcagaggttt tcaccgtcat caccgaaacg cgcgagacga aagggcctcg tgatacgcct    3900 attttttatag gttaatgtca tgataataat ggtttcttag acgtcaggtg cacttttcg    3960 gggaaatgtg cgcggaaccc ctatttgttt attttttctaa atacattcaa atatgtatcc    4020
gctcatgaga caataaccct gataaatgct tcaataatat tgaaaaagga agagtatgag    4080
tattcaacat ttccgtgtcg cccttattcc ctttttttgcg cattttgcc ttcctgtttt    4140 tgctcaccca gaaacgctgg tgaaagtaaa agatgctgaa gatcagttgg gtgcacgagt    4200
gggttacatc gaactggatc tcaacagcgg taagatcctt gagagttttc gccccgaaga    4260
acgttttcca atgatgagca cttttaaagt tctgctatgt ggcgcggtat tatcccgtat    4320
tgacgccggg caagagcaac tcggtcgccg catacactat tctcagaatg acttggttga    4380
gtactcacca gtcacagaaa agcatcttac ggatggcatg acagtaagag aattatgcag    4440
tgctgccata accatgagtg ataacactgc ggccaactta cttctgacaa cgatcggagg    4500
accgaaggag ctaaccgctt ttttgcacaa catgggggat catgtaactc gccttgatcg    4560
ttgggaaccg gagctgaatg aagccatacc aaacgacgag cgtgacacca cgatgcctgt    4620
agcaatggca acaacgttgc gcaaactatt aactggcgaa ctacttactc tagcttcccg    4680
gcaacaatta atagactgga tggaggcgga taaagttgca ggaccacttc tgcgctcggc    4740
ccttccggct ggctggttta ttgctgataa atctggagcc ggtgagcgtg gtctcgcgg    4800 tatcattgca gcactggggc cagatggtaa gccctcccgt atcgtagtta tctacacgac    4860
ggggagtcag gcaactatgg atgaacgaaa tagacagatc gctgagatag gtgcctcact    4920
gattaagcat tggtaactgt cagaccaagt ttactcatat atactttaga ttgatttaaa    4980
acttcatttt taatttaaaa ggatctaggt gaagatcctt tttgataatc tcatgaccaa    5040
aatcccttaa cgtgagtttt cgttccactg agcgtcagac cccgtagaaa agatcaaagg    5100
atcttcttga tccttttttt ttctgcgcgt aatctgctgc ttgcaaacaa aaaaaccacc    5160
gctaccagcg gtggtttgtt tgccggatca agagctacca actctttttc cgaaggtaac    5220
tggcttcagc agagcgcaga taccaaatac tgttcttcta gtgtagccgt agttaggcca    5280
ccacttcaag aactctgtag caccgcctac atacctcgct ctgctaatcc tgttaccagt    5340
ggctgctgcc agtggcgata gtcgtgtct taccgggttg gactcaagac gatagttacc    5400
ggataaggcg cagcggtcgg gctgaacggg gggttcgtgc acacagccca gcttggagcg    5460
aacgacctac accgaactga gatacctaca gcgtgagcta tgagaaagcg ccacgcttcc    5520
cgaagggaga aaggcggaca ggtatccggt aagcggcagg gtcggaacag gagagcgcac    5580
gagggagctt ccagggggaa acgcctggta tctttatagt cctgtcgggt ttcgccacct    5640
ctgacttgag cgtcgatttt tgtgatgctc gtcaggggg cggagcctat ggaaaaacgc    5700
cagcaacgcg gccttttac ggttcctggc cttttgctgg ccttttgctc acatgt       5756
```

<210> SEQ ID NO 2
<211> LENGTH: 18
<212> TYPE: DNA

```
<213> ORGANISM: Artificial Sequence
<220> FEATURE:
<223> OTHER INFORMATION: Description of Artificial Sequence:
      Synthetic oligonucleotide

<400> SEQUENCE: 2
caggctggca caaaggag                                                 18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 3
agtgaggcag gatcggtatg                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 4
agcgtgccat ttagcgtatc                                               20

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 5
gcagtagact ctgttctcag cctaac                                        26

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 6
accttttctc ataaatagat acgaatcc                                      28

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 7
tcttgttccc tgctgtaccc                                               20

<210> SEQ ID NO 8
<211> LENGTH: 20
<212> TYPE: DNA
<213> ORGANISM: Artificial Sequence
```

```
<220> FEATURE:
<223> OTHER INFORMATION: Description of Artificial Sequence:
      Synthetic oligonucleotide

<400> SEQUENCE: 8
gcatgcaagc cttcataaca                                              20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 9
cgaggtcatt gttgttatga cg                                           22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 10
cgtggccatg ttaactcctt                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 11
gttccctgaa ttcccagtca                                              20

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 12
atgtttaata tttcacgaac atattcc                                      27

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 13
gctgtttccc agtcaaggag                                              20

<210> SEQ ID NO 14
<211> LENGTH: 25
<212> TYPE: DNA
<213> ORGANISM: Artificial Sequence
<220> FEATURE:
```

```
<223> OTHER INFORMATION: Description of Artificial Sequence:
      Synthetic oligonucleotide

<400> SEQUENCE: 14
tgagtcatca gatttctctt gtttg                                            25

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 15
agcctgggcg actgagtgag                                                  20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 16
aaaagaaaac atagatggca aaaga                                            25

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 17
tcccgctcag ttaagtttgg                                                  20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 18
gcttcaaaat cccctccttc                                                  20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 19
cacctggctc tttcctcttg                                                  20

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence:
```

Synthetic oligonucleotide

<400> SEQUENCE: 20
ccctgagatc ccaagactg                                                19

<210> SEQ ID NO 21
<211> LENGTH: 20
<212> TYPE: RNA
<213> ORGANISM: Homo sapiens

<400> SEQUENCE: 21
agguggagau gaucuuaaac                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 22
gtttaagatc atctccacct                                               20

<210> SEQ ID NO 23
<211> LENGTH: 20
<212> TYPE: RNA
<213> ORGANISM: Homo sapiens

<400> SEQUENCE: 23
gguggagaug aucuuaaaca                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 24
tgtttaagat catctccacc                                               20

<210> SEQ ID NO 25
<211> LENGTH: 20
<212> TYPE: RNA
<213> ORGANISM: Homo sapiens

<400> SEQUENCE: 25
ugaucuuaaa caaaccuggc                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 26
gccaggtttg tttaagatca                                               20

<210> SEQ ID NO 27
<211> LENGTH: 20
<212> TYPE: RNA

```
<213> ORGANISM: Homo sapiens

<400> SEQUENCE: 27
uaaacaaacc uggcuugaag                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 28
cttcaagcca ggtttgttta                                              20

<210> SEQ ID NO 29
<211> LENGTH: 22
<212> TYPE: RNA
<213> ORGANISM: Homo sapiens

<400> SEQUENCE: 29
cagguggaga ugaucuuaaa ca                                           22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 30
tgtttaagat catctccacc tg                                           22

<210> SEQ ID NO 31
<211> LENGTH: 22
<212> TYPE: RNA
<213> ORGANISM: Homo sapiens

<400> SEQUENCE: 31
gaucuuaaac aaaccuggcu ug                                           22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 32
caagccaggt ttgtttaaga tc                                           22

<210> SEQ ID NO 33
<211> LENGTH: 22
<212> TYPE: RNA
<213> ORGANISM: Homo sapiens

<400> SEQUENCE: 33
cuuaaacaaa ccuggcuuga ag                                           22

<210> SEQ ID NO 34
<211> LENGTH: 22
<212> TYPE: DNA
```

```
<213> ORGANISM: Artificial Sequence
<220> FEATURE:
<223> OTHER INFORMATION: Description of Artificial Sequence:
      Synthetic oligonucleotide

<400> SEQUENCE: 34
cttcaagcca ggtttgttta ag                                          22

<210> SEQ ID NO 35
<211> LENGTH: 22
<212> TYPE: RNA
<213> ORGANISM: Homo sapiens

<400> SEQUENCE: 35
aaguauaagc ugcaguuaa cc                                           22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 36
ggttaactgc aggcttatac tt                                          22

<210> SEQ ID NO 37
<211> LENGTH: 22
<212> TYPE: RNA
<213> ORGANISM: Homo sapiens

<400> SEQUENCE: 37
ucaaggcgau cgcagccaag ca                                          22

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 38
tgcttggctg cgatcgcctt ga                                          22

<210> SEQ ID NO 39
<211> LENGTH: 22
<212> TYPE: RNA
<213> ORGANISM: Homo sapiens

<400> SEQUENCE: 39
aaggcgaucg cagccaagca ca                                          22

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 40
tgtgcttggc tgcgatcgcc tt                                          22
```

```
<210> SEQ ID NO 41
<211> LENGTH: 22
<212> TYPE: RNA
<213> ORGANISM: Homo sapiens

<400> SEQUENCE: 41
accuguguuu cuugccucau uu                                              22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 42
aaatgaggca agaaacacag gt                                              22

<210> SEQ ID NO 43
<211> LENGTH: 73
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 43
gtagatgccc gcctggatgg aggcctctgc cccgtgcac tcgatggtga cttccggctt     60
gcaccccagc tga                                                        73

<210> SEQ ID NO 44
<211> LENGTH: 72
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 44
gtagatgcct gcctggatgg aggcctctgc cccgtgcact cgatggtgac ttccggcttg     60 cacccccagca ga                                                        72

<210> SEQ ID NO 45
<211> LENGTH: 1074
<212> TYPE: DNA
<213> ORGANISM: Homo sapiens

<400> SEQUENCE: 45
atggcggcgg cggccaagcc caacaacctt tccctggtgg tgcacggacc gggggacttg     60
cgcctggaga actatcctat ccctgaacca ggcccaaatg aggtcttgct gaggatgcat    120
tctgttggaa tctgtggctc agatgtccac tactgggagt atggtcgaat tgggaatttt    180
attgtgaaaa agcccatggt gctgggacat gaagcttcgg gaacagtcga aaagtggga    240 tcatcggtaa agcacctaaa accaggtgat cgtgttgcca tcgagcctgg tgctccccga    300
gaaaatgatg aattctgcaa gatgggccga tacaatctgt caccttccat cttcttctgt    360
gccacgcccc ccgatgacgg gaacctctgc cggttctata agcacaatgc agccttttgt    420
tacaagcttc ctgacaatgt caccttgag gaaggcgccc tgatcgagcc actttctgtg    480
gggatccatg cctgcaggag aggcggagtt accctgggac acaaggtcct tgtgtgtgga    540
gctgggccaa tcgggatggt cactttgctc gtggccaaag caatgggagc agctcaagta    600
```

```
gtggtgactg atctgtctgc tacccgattg tccaaagcca aggagattgg ggctgattta      660
gtcctccaga tctccaagga gagccctcag gaaatcgcca ggaaagtaga aggtcagctg      720
gggtgcaagc cggaagtcac catcgagtgc acggggcag aggcctccat ccaggcgggc       780
atctacgcca ctcgctctgg tgggaacctc gtgcttgtgg ggctgggctc tgagatgacc      840
accgtacccc tactgcatgc agccatccgg gaggtggata tcaagggcgt gtttcgatac      900
tgcaacacgt ggccagtggc gatttcgatg cttgcgtcca gtctgtgaa tgtaaaaccc      960 ctcgtcaccc ataggtttcc tctggagaaa gctctggagg cctttgaaac atttaaaaag     1020
ggattggggt tgaaaatcat gctcaagtgt gaccccagtg accagaatcc ctga           1074
```

<210> SEQ ID NO 46
<211> LENGTH: 357
<212> TYPE: PRT
<213> ORGANISM: Homo sapiens

<400> SEQUENCE: 46

```
Met Ala Ala Ala Lys Pro Asn Asn Leu Ser Leu Val Val His Gly
1               5                  10                  15

Pro Gly Asp Leu Arg Leu Glu Asn Tyr Pro Ile Pro Glu Pro Gly Pro
            20                  25                  30

Asn Glu Val Leu Leu Arg Met His Ser Val Gly Ile Cys Gly Ser Asp
        35                  40                  45

Val His Tyr Trp Glu Tyr Gly Arg Ile Gly Asn Phe Ile Val Lys Lys
    50                  55                  60

Pro Met Val Leu Gly His Glu Ala Ser Gly Thr Val Glu Lys Val Gly
65                  70                  75                  80

Ser Ser Val Lys His Leu Lys Pro Gly Asp Arg Val Ala Ile Glu Pro
                85                  90                  95

Gly Ala Pro Arg Glu Asn Asp Glu Phe Cys Lys Met Gly Arg Tyr Asn
            100                 105                 110

Leu Ser Pro Ser Ile Phe Phe Cys Ala Thr Pro Pro Asp Asp Gly Asn
        115                 120                 125

Leu Cys Arg Phe Tyr Lys His Asn Ala Ala Phe Cys Tyr Lys Leu Pro
    130                 135                 140

Asp Asn Val Thr Phe Glu Glu Gly Ala Leu Ile Glu Pro Leu Ser Val
145                 150                 155                 160

Gly Ile His Ala Cys Arg Arg Gly Gly Val Thr Leu Gly His Lys Val
                165                 170                 175

Leu Val Cys Gly Ala Gly Pro Ile Gly Met Val Thr Leu Leu Val Ala
            180                 185                 190

Lys Ala Met Gly Ala Ala Gln Val Val Val Thr Asp Leu Ser Ala Thr
        195                 200                 205

Arg Leu Ser Lys Ala Lys Glu Ile Gly Ala Asp Leu Val Leu Gln Ile
    210                 215                 220

Ser Lys Glu Ser Pro Gln Glu Ile Ala Arg Lys Val Glu Gly Gln Leu
225                 230                 235                 240

Gly Cys Lys Pro Glu Val Thr Ile Glu Cys Thr Gly Ala Glu Ala Ser
                245                 250                 255

Ile Gln Ala Gly Ile Tyr Ala Thr Arg Ser Gly Gly Asn Leu Val Leu
            260                 265                 270

Val Gly Leu Gly Ser Glu Met Thr Thr Val Pro Leu Leu His Ala Ala
        275                 280                 285
```

```
Ile Arg Glu Val Asp Ile Lys Gly Val Phe Arg Tyr Cys Asn Thr Trp
    290                 295                 300

Pro Val Ala Ile Ser Met Leu Ala Ser Lys Ser Val Asn Val Lys Pro
305                 310                 315                 320

Leu Val Thr His Arg Phe Pro Leu Glu Lys Ala Leu Glu Ala Phe Glu
                325                 330                 335

Thr Phe Lys Lys Gly Leu Gly Leu Lys Ile Met Leu Lys Cys Asp Pro
            340                 345                 350

Ser Asp Gln Asn Pro
        355

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 47
tattacagct acatcctgtc                                                20

<210> SEQ ID NO 48
<211> LENGTH: 5756
<212> TYPE: DNA
<213> ORGANISM: Homo sapiens

<400> SEQUENCE: 48
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccgca accgtctagt tattaatagt aatcaattac    180
ggggtcatta gttcatagcc catatatgga gttccgcgtt acataactta cggtaaatgg    240
cccgcctggc tgaccgccca cgacccccg cccattgacg tcaataatga cgtatgttcc     300
catagtaacg ccaataggga ctttccattg acgtcaatgg gtggagtatt tacggtaaac    360
tgcccacttg gcagtacatc aagtgtatca tatgccaagt acgccccta ttgacgtcaa     420 tgacggtaaa tggcccgcct ggcattatgc ccagtacatg accttatggg actttcctac    480
ttggcagtac atctacgtat tagtcatcgc tattaccatg gtgatgcggt tttggcagta    540
catcaatggg cgtggatagc ggtttgactc acggggattt ccaagtctcc accccattga    600
cgtcaatggg agtttgtttt ggcaccaaaa tcaacgggac tttccaaaat gtcgtaacaa    660
ctccgcccca ttgacgcaaa tgggcggtag gcgtgtacgg tgggaggtct atataagcag    720
agctcgttta gtgaaccgtc agatcgcctg gagacgccat ccacgctgtt ttgacctcca    780
tagaagacac cgggaccgat ccagcctccg cggattcgaa tcccggccgg gaacggtgca    840
ttggaacgcg gattcccgt gccaagagtg acgtaagtac cgcctataga gtctataggc     900
ccacaaaaaa tgctttcttc ttttaatata ctttttttgtt tatcttattt ctaatacttt    960
ccctaatctc tttctttcag ggcaataatg atacaatgta tcatgcctct tgcaccatt    1020 ctaaagaata acagtgataa tttctgggtt aaggcaatag caatatttct gcatataaat   1080
atttctgcat ataaattgta actgatgtaa gaggtttcat attgctaata gcagctacaa   1140
tccagctacc attctgcttt tattttatgg ttgggataag gctggattat tctgagtcca   1200
agctaggccc ttttgctaat catgttcata cctcttatct tcctcccaca gctcctgggc   1260
aacgtgctgg tctgtgtgct ggcccatcac tttggcaaag aattgggatt cgaacatcga   1320
```

```
tccgaggaga tctgccgccg cgatcgccgg cgcgccatgg cggcggcggc caagcccaac    1380
aacctttccc tggtggtgca cggaccgggg gacttgcgcc tggagaacta tcctatccct    1440
gaaccaggcc caaatgaggt cttgctgagg atgcattctg ttggaatctg tggctcagat    1500
gtccactact gggagtatgg tcgaattggg aattttattg tgaaaaagcc catggtgctg    1560
ggacatgaag cttcgggaac agtcgaaaaa gtgggatcat cggtaaagca cctaaaacca    1620
ggtgatcgtg ttgccatcga gcctggtgct ccccgagaaa atgatgaatt ctgcaagatg    1680
ggccgataca atctgtcacc ttccatcttc ttctgtgcca cgccccccga tgacgggaac    1740
ctctgccggt tctataagca caatgcagcc ttttgttaca agcttcctga caatgtcacc    1800
tttgaggaag gcgccctgat cgagccactt tctgtgggga tccatgcctg caggagaggc    1860
ggagttaccc tgggacacaa ggtccttgtg tgtggagctg gccaatcgg gatggtcact    1920 ttgctcgtgg ccaaagcaat gggagcagct caagtagtgg tgactgatct gtctgctacc    1980
cgattgtcca aagccaagga gatttgggct gatttagtcc tccagatctc caaggagagc    2040
cctcaggaaa tcgccaggaa agtagaaggt cagctggggt gcaagccgga agtcaccatc    2100
gagtgcacgg gggcagaggc ctccatccag gcgggcatct acgccactcg ctctggtggg    2160
aacctcgtgc ttgtggggct gggctctgag atgaccaccg tacccctact gcatgcagcc    2220
atccgggagg tggatatcaa gggcgtgttt cgatactgca acacgtggcc agtgcgatt     2280 tcgatgcttg cgtccaagtc tgtgaatgta aacccctcg tcacccatag gtttcctctg     2340
gagaaagctc tggaggcctt tgaaacattt aaaaagggat tggggttgaa aatcatgctc    2400
aagtgtgacc ccagtgacca gaatccctga agatctcaag cttaactagc tagcggaccg    2460
acgcgtacgc ggccgctcgt ttaaacggcc ggccggatct acgggtggca tccctgtgac    2520
ccctccccag tgcctctcct ggccctggaa gttgccactc cagtgcccac cagccttgtc    2580
ctaataaaat taagttgcat catttttgtct gactaggtgt ccttctataa tattatgggg    2640 tggaggggg tggtatggag caaggggcaa gttgggaaga caacctgtag ggcctgcggg    2700
gtctattggg aaccaagctg gagtgcagtg gcacaatctt ggctcactgc aatctccgcc    2760
tcctgggttc aagcgattct cctgcctcag cctcccgagt tgttgggatt ccaggcatgc    2820
atgaccaggc tcagctaatt tttgtttttt tggtagagac ggggtttcac catattggcc    2880
aggctggtct ccaactccta atctcaggtg atctacccac cttggcctcc caaattgctg    2940
ggattacagg cgtgaaccac tgctcccttc cctgtccttc tgattttgta ggtaaccacg    3000
tgcggaccga gcggccgcag gaaccctag tgatggagtt ggccactccc tctctgcgcg    3060
ctcgctcgct cactgaggcc gggcgaccaa aggtcgcccg acgcccggc tttgcccggg    3120 cggcctcagt gagcgagcga gcgcgcagct gcctgcaggg gcgcctgatg cggtattttc    3180
tccttacgca tctgtgcggt atttcacacc gcatacgtca aagcaaccat agtacgcgcc    3240
ctgtagcggc gcattaagcg cggcgggtgt ggtggttacg cgcagcgtga ccgctacact    3300
tgccagcgcc ctagcgcccg ctcctttcgc tttcttccct ccttctcg ccacgttcgc     3360 cggcttccc cgtcaagctc taaatcgggg ctccctttta gggttccgat ttagtgcttt    3420
acggcacctc gaccccaaaa aacttgattt gggtgatggt tcacgtagtg gccatcgcc    3480 ctgatagacg gtttttcgcc ctttgacgtt ggagtccacg ttctttaata gtggactctt    3540
gttccaaact ggaacaacac tcaactctat ctcgggctat tcttttgatt tataagggat    3600
tttgccgatt tcggtctatt ggttaaaaaa tgagctgatt taacaaaaat ttaacgcgaa    3660
```

| | |
|---|---|
| tttttaacaaa atattaacgt ttacaatttt atggtgcact ctcagtacaa tctgctctga | 3720 |
| tgccgcatag ttaagccagc cccgacaccc gccaacaccc gctgacgcgc cctgacgggc | 3780 |
| ttgtctgctc ccggcatccg cttacagaca agctgtgacc gtctccggga gctgcatgtg | 3840 |
| tcagaggttt tcaccgtcat caccgaaacg cgcgagacga aagggcctcg tgatacgcct | 3900 |
| attttatag gttaatgtca tgataataat ggtttcttag acgtcaggtg gcacttttcg | 3960 |
| gggaaatgtg cgcggaaccc ctatttgttt attttctaa atacattcaa atatgtatcc | 4020 |
| gctcatgaga caataaccct gataaatgct tcaataatat tgaaaaagga agagtatgag | 4080 |
| tattcaacat ttccgtgtcg cccttattcc cttttttgcg gcattttgcc ttcctgtttt | 4140 |
| tgctcaccca gaaacgctgg tgaaagtaaa agatgctgaa gatcagttgg gtgcacgagt | 4200 |
| gggttacatc gaactggatc tcaacagcgg taagatcctt gagagttttc gccccgaaga | 4260 |
| acgttttcca atgatgagca cttttaaagt tctgctatgt ggcgcggtat tatcccgtat | 4320 |
| tgacgccggg caagagcaac tcggtcgccg catacactat tctcagaatg acttggttga | 4380 |
| gtactcacca gtcacagaaa agcatcttac ggatggcatg acagtaagag aattatgcag | 4440 |
| tgctgccata accatgagtg ataacactgc ggccaactta cttctgacaa cgatcggagg | 4500 |
| accgaaggag ctaaccgctt ttttgcacaa catgggggat catgtaactc gccttgatcg | 4560 |
| ttgggaaccg gagctgaatg aagccatacc aaacgacgag cgtgacacca cgatgcctgt | 4620 |
| agcaatggca acaacgttgc gcaaactatt aactggcgaa ctacttactc tagcttcccg | 4680 |
| gcaacaatta atagactgga tggaggcgga taaagttgca ggaccacttc tgcgctcggc | 4740 |
| ccttccggct ggctggttta ttgctgataa atctggagcc ggtgagcgtg gtctcgcgg | 4800 |
| tatcattgca gcactggggc cagatggtaa gccctcccgt atcgtagtta tctacacgac | 4860 |
| ggggagtcag gcaactatgg atgaacgaaa tagacagatc gctgagatag gtgcctcact | 4920 |
| gattaagcat tggtaactgt cagaccaagt ttactcatat atactttaga ttgatttaaa | 4980 |
| acttcatttt taatttaaaa ggatctaggt gaagatcctt tttgataatc tcatgaccaa | 5040 |
| aatcccttaa cgtgagtttt cgttccactg agcgtcagac cccgtagaaa agatcaaagg | 5100 |
| atcttcttga tccttttttt ttctgcgcgt aatctgctgc ttgcaaacaa aaaaaccacc | 5160 |
| gctaccagcg gtggtttgtt tgccggatca agagctacca actcttttc cgaaggtaac | 5220 |
| tggcttcagc agagcgcaga taccaaatac tgttcttcta gtgtagccgt agttaggcca | 5280 |
| ccacttcaag aactctgtag caccgcctac atacctcgct ctgctaatcc tgttaccagt | 5340 |
| ggctgctgcc agtggcgata agtcgtgtct taccgggttg gactcaagac gatagttacc | 5400 |
| ggataaggcg cagcggtcgg gctgaacggg gggttcgtgc acacagccca gcttggagcg | 5460 |
| aacgacctac accgaactga gatacctaca gcgtgagcta tgagaaagcg ccacgcttcc | 5520 |
| cgaagggaga aaggcggaca ggtatccggt aagcggcagg gtcggaacag gagagcgcac | 5580 |
| gagggagctt ccagggggaa acgcctggta tctttatagt cctgtcgggt ttcgccacct | 5640 |
| ctgacttgag cgtcgatttt tgtgatgctc gtcaggggg cggagcctat ggaaaaacgc | 5700 |
| cagcaacgcg gcctttttac ggttcctggc cttttgctgg ccttttgctc acatgt | 5756 |

<210> SEQ ID NO 49
<211> LENGTH: 20
<212> TYPE: RNA
<213> ORGANISM: Homo sapiens

<400> SEQUENCE: 49

| | |
|---|---|
| ucgcagccaa gcacaauaaa | 20 |

```
<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 50
tttattgtgc ttggctgcga                                           20

<210> SEQ ID NO 51
<211> LENGTH: 20
<212> TYPE: RNA
<213> ORGANISM: Homo sapiens

<400> SEQUENCE: 51
gcagccaagc acaauaaaac                                           20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 52
gttttattgt gcttggctgc                                           20

<210> SEQ ID NO 53
<211> LENGTH: 20
<212> TYPE: RNA
<213> ORGANISM: Homo sapiens

<400> SEQUENCE: 53
gaucgcagcc aagcacaaua                                           20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 54
tattgtgctt ggctgcgatc                                           20

<210> SEQ ID NO 55
<211> LENGTH: 20
<212> TYPE: RNA
<213> ORGANISM: Homo sapiens

<400> SEQUENCE: 55
aucgcagcca agcacaauaa                                           20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide
```

```
<400> SEQUENCE: 56
ttattgtgct tggctgcgat                                          20

<210> SEQ ID NO 57
<211> LENGTH: 20
<212> TYPE: RNA
<213> ORGANISM: Homo sapiens

<400> SEQUENCE: 57
cgcagccaag cacaauaaaa                                          20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 58
ttttattgtg cttggctgcg                                          20

<210> SEQ ID NO 59
<211> LENGTH: 20
<212> TYPE: RNA
<213> ORGANISM: Homo sapiens

<400> SEQUENCE: 59
gccaagcaca auaaaacuac                                          20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 60
gtagttttat tgtgcttggc                                          20

<210> SEQ ID NO 61
<211> LENGTH: 20
<212> TYPE: RNA
<213> ORGANISM: Homo sapiens

<400> SEQUENCE: 61
cgaucgcagc caagcacaau                                          20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 62
attgtgcttg gctgcgatcg                                          20

<210> SEQ ID NO 63
<211> LENGTH: 20
<212> TYPE: RNA
<213> ORGANISM: Homo sapiens
```

```
<400> SEQUENCE: 63
agcacaauaa aacuacagcc                                              20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 64
ggctgtagtt ttattgtgct                                              20

<210> SEQ ID NO 65
<211> LENGTH: 20
<212> TYPE: RNA
<213> ORGANISM: Homo sapiens

<400> SEQUENCE: 65
cagccaagca caauaaaacu                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 66
agttttattg tgcttggctg                                              20

<210> SEQ ID NO 67
<211> LENGTH: 20
<212> TYPE: RNA
<213> ORGANISM: Homo sapiens

<400> SEQUENCE: 67
gcgaucgcag ccaagcacaa                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 68
ttgtgcttgg ctgcgatcgc                                              20

<210> SEQ ID NO 69
<211> LENGTH: 20
<212> TYPE: RNA
<213> ORGANISM: Homo sapiens

<400> SEQUENCE: 69
gcacaauaaa acuacagccc                                              20

<210> SEQ ID NO 70
<211> LENGTH: 20
<212> TYPE: DNA
<213> ORGANISM: Artificial Sequence
<220> FEATURE:
```

```
<223> OTHER INFORMATION: Description of Artificial Sequence:
      Synthetic oligonucleotide

<400> SEQUENCE: 70
gggctgtagt tttattgtgc                                              20

<210> SEQ ID NO 71
<211> LENGTH: 20
<212> TYPE: RNA
<213> ORGANISM: Homo sapiens

<400> SEQUENCE: 71
aaccagauug agugccaccc                                              20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 72
gggtggcact caatctggtt                                              20

<210> SEQ ID NO 73
<211> LENGTH: 20
<212> TYPE: RNA
<213> ORGANISM: Homo sapiens

<400> SEQUENCE: 73
accagauuga gugccaccca                                              20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 74
tgggtggcac tcaatctggt                                              20

<210> SEQ ID NO 75
<211> LENGTH: 20
<212> TYPE: RNA
<213> ORGANISM: Homo sapiens

<400> SEQUENCE: 75
accucccaca aggauuaccc                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 76
gggtaatcct tgtgggaggt                                              20

<210> SEQ ID NO 77
<211> LENGTH: 20
```

```
<212> TYPE: RNA
<213> ORGANISM: Homo sapiens

<400> SEQUENCE: 77
ccucccacaa ggauuacccc                                              20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 78
ggggtaatcc ttgtgggagg                                              20

<210> SEQ ID NO 79
<211> LENGTH: 20
<212> TYPE: RNA
<213> ORGANISM: Homo sapiens

<400> SEQUENCE: 79
acaaccugaa uacccuuuuc                                              20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 80
gaaaagggta ttcaggttgt                                              20

<210> SEQ ID NO 81
<211> LENGTH: 20
<212> TYPE: RNA
<213> ORGANISM: Homo sapiens

<400> SEQUENCE: 81
cucccacaag gauuaccccu                                              20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 82
aggggtaatc cttgtgggag                                              20

<210> SEQ ID NO 83
<211> LENGTH: 20
<212> TYPE: RNA
<213> ORGANISM: Homo sapiens

<400> SEQUENCE: 83
ccagauugag ugccacccau                                              20

<210> SEQ ID NO 84
<211> LENGTH: 20
```

```
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 84
atgggtggca ctcaatctgg                                              20

<210> SEQ ID NO 85
<211> LENGTH: 20
<212> TYPE: RNA
<213> ORGANISM: Homo sapiens

<400> SEQUENCE: 85
caaccugaau acccuuuucu                                              20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 86
agaaaagggt attcaggttg                                              20

<210> SEQ ID NO 87
<211> LENGTH: 20
<212> TYPE: RNA
<213> ORGANISM: Homo sapiens

<400> SEQUENCE: 87
aguacaaccu gaauacccuu                                              20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 88
aagggtattc aggttgtact                                              20

<210> SEQ ID NO 89
<211> LENGTH: 20
<212> TYPE: RNA
<213> ORGANISM: Homo sapiens

<400> SEQUENCE: 89
guacaaccug aauacccuuu                                              20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 90
aaagggtatt caggttgtac                                              20
```

```
<210> SEQ ID NO 91
<211> LENGTH: 20
<212> TYPE: RNA
<213> ORGANISM: Homo sapiens

<400> SEQUENCE: 91
aaggcgaucg cagccaagca                                               20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 92
tgcttggctg cgatcgcctt                                               20

<210> SEQ ID NO 93
<211> LENGTH: 20
<212> TYPE: RNA
<213> ORGANISM: Homo sapiens

<400> SEQUENCE: 93
ucccacaagg auuaccccuu                                               20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 94
aaggggtaat ccttgtggga                                               20

<210> SEQ ID NO 95
<211> LENGTH: 20
<212> TYPE: RNA
<213> ORGANISM: Homo sapiens

<400> SEQUENCE: 95
aaguacaacc ugaauacccu                                               20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 96
agggtattca ggttgtactt                                               20

<210> SEQ ID NO 97
<211> LENGTH: 20
<212> TYPE: RNA
<213> ORGANISM: Homo sapiens

<400> SEQUENCE: 97
aaccugaaua cccuuuucug                                               20
```

```
<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 98
cagaaaaggg tattcaggtt                                               20

<210> SEQ ID NO 99
<211> LENGTH: 20
<212> TYPE: RNA
<213> ORGANISM: Homo sapiens

<400> SEQUENCE: 99
accugaauac ccuuuucuga                                               20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 100
tcagaaaagg gtattcaggt                                               20

<210> SEQ ID NO 101
<211> LENGTH: 20
<212> TYPE: RNA
<213> ORGANISM: Homo sapiens

<400> SEQUENCE: 101
uaccucccac aaggauuacc                                               20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 102
ggtaatcctt gtgggaggta                                               20

<210> SEQ ID NO 103
<211> LENGTH: 20
<212> TYPE: RNA
<213> ORGANISM: Homo sapiens

<400> SEQUENCE: 103
aaaguacaac cugaauaccc                                               20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 104
```

```
gggtattcag gttgtacttt                                               20

<210> SEQ ID NO 105
<211> LENGTH: 20
<212> TYPE: RNA
<213> ORGANISM: Homo sapiens

<400> SEQUENCE: 105
ccugaauacc cuuuucugac                                               20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 106
gtcagaaaag ggtattcagg                                               20

<210> SEQ ID NO 107
<211> LENGTH: 20
<212> TYPE: RNA
<213> ORGANISM: Homo sapiens

<400> SEQUENCE: 107
uaaccagauu gagugccacc                                               20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 108
ggtggcactc aatctggtta                                               20

<210> SEQ ID NO 109
<211> LENGTH: 20
<212> TYPE: RNA
<213> ORGANISM: Homo sapiens

<400> SEQUENCE: 109
auugagugcc acccauaucu                                               20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 110
agatatgggt ggcactcaat                                               20

<210> SEQ ID NO 111
<211> LENGTH: 20
<212> TYPE: RNA
<213> ORGANISM: Homo sapiens

<400> SEQUENCE: 111
```

```
gugccaccca uaucucacuc                                            20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 112
gagtgagata tgggtggcac                                            20

<210> SEQ ID NO 113
<211> LENGTH: 20
<212> TYPE: RNA
<213> ORGANISM: Homo sapiens

<400> SEQUENCE: 113
ugccacccau aucucacuca                                            20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 114
tgagtgagat atgggtggca                                            20

<210> SEQ ID NO 115
<211> LENGTH: 20
<212> TYPE: RNA
<213> ORGANISM: Homo sapiens

<400> SEQUENCE: 115
cacaauaaaa cuacagccca                                            20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 116
tgggctgtag ttttattgtg                                            20

<210> SEQ ID NO 117
<211> LENGTH: 20
<212> TYPE: RNA
<213> ORGANISM: Homo sapiens

<400> SEQUENCE: 117
cccacaagga uuaccccuuc                                            20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence:
```

Synthetic oligonucleotide

<400> SEQUENCE: 118 gaagggtaa tccttgtggg                                              20

<210> SEQ ID NO 119
<211> LENGTH: 20
<212> TYPE: RNA
<213> ORGANISM: Homo sapiens

<400> SEQUENCE: 119
cugaauaccc uuuucugacc                                             20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 120
ggtcagaaaa gggtattcag                                             20

<210> SEQ ID NO 121
<211> LENGTH: 20
<212> TYPE: RNA
<213> ORGANISM: Homo sapiens

<400> SEQUENCE: 121
gauugagugc cacccauauc                                             20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 122
gatatgggtg gcactcaatc                                             20

<210> SEQ ID NO 123
<211> LENGTH: 20
<212> TYPE: RNA
<213> ORGANISM: Homo sapiens

<400> SEQUENCE: 123
agugccaccc auaucucacu                                             20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 124
agtgagatat gggtggcact                                             20

<210> SEQ ID NO 125
<211> LENGTH: 20
<212> TYPE: RNA

```
<213> ORGANISM: Homo sapiens

<400> SEQUENCE: 125
gccacccaua ucucacucag                                               20

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 126
ctgagtgaga tatgggtggc                                               20

<210> SEQ ID NO 127
<211> LENGTH: 20
<212> TYPE: RNA
<213> ORGANISM: Homo sapiens

<400> SEQUENCE: 127
gagugccacc cauaucucac                                               20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 128
gtgagatatg ggtggcactc                                               20

<210> SEQ ID NO 129
<211> LENGTH: 20
<212> TYPE: RNA
<213> ORGANISM: Homo sapiens

<400> SEQUENCE: 129
ugaauacccu uuucugacca                                               20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 130
tggtcagaaa agggtattca                                               20

<210> SEQ ID NO 131
<211> LENGTH: 20
<212> TYPE: RNA
<213> ORGANISM: Homo sapiens

<400> SEQUENCE: 131
uugagugcca cccauaucuc                                               20

<210> SEQ ID NO 132
<211> LENGTH: 20
<212> TYPE: DNA
```

```
<213> ORGANISM: Artificial Sequence
<220> FEATURE:
<223> OTHER INFORMATION: Description of Artificial Sequence:
      Synthetic oligonucleotide

<400> SEQUENCE: 132
gagatatggg tggcactcaa                                              20

<210> SEQ ID NO 133
<211> LENGTH: 20
<212> TYPE: RNA
<213> ORGANISM: Homo sapiens

<400> SEQUENCE: 133
ugagugccac ccauaucuca                                              20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 134
tgagatatgg gtggcactca                                              20

<210> SEQ ID NO 135
<211> LENGTH: 20
<212> TYPE: RNA
<213> ORGANISM: Homo sapiens

<400> SEQUENCE: 135
agauugagug ccacccauau                                              20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 136
atatgggtgg cactcaatct                                              20

<210> SEQ ID NO 137
<211> LENGTH: 20
<212> TYPE: RNA
<213> ORGANISM: Homo sapiens

<400> SEQUENCE: 137
ccacccauau cucacucagg                                              20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 138
cctgagtgag atatgggtgg                                              20
```

```
<210> SEQ ID NO 139
<211> LENGTH: 20
<212> TYPE: RNA
<213> ORGANISM: Homo sapiens

<400> SEQUENCE: 139
cagauugagu gccacccaua                                              20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 140
tatgggtggc actcaatctg                                              20

<210> SEQ ID NO 141
<211> LENGTH: 20
<212> TYPE: RNA
<213> ORGANISM: Homo sapiens

<400> SEQUENCE: 141
ccacaaggau uaccccuucc                                              20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 142
ggaaggggta atccttgtgg                                              20

<210> SEQ ID NO 143
<211> LENGTH: 20
<212> TYPE: RNA
<213> ORGANISM: Homo sapiens

<400> SEQUENCE: 143
gaaaguacaa ccugaauacc                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 144
ggtattcagg ttgtactttc                                              20

<210> SEQ ID NO 145
<211> LENGTH: 20
<212> TYPE: RNA
<213> ORGANISM: Homo sapiens

<400> SEQUENCE: 145
gaauacccuu uucugaccaa                                              20
```

```
<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 146
ttggtcagaa aagggtattc                                                 20

<210> SEQ ID NO 147
<211> LENGTH: 20
<212> TYPE: RNA
<213> ORGANISM: Homo sapiens

<400> SEQUENCE: 147
acaauaaaac uacagcccag                                                 20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 148
ctgggctgta gttttattgt                                                 20

<210> SEQ ID NO 149
<211> LENGTH: 20
<212> TYPE: RNA
<213> ORGANISM: Homo sapiens

<400> SEQUENCE: 149
guaccuccca caaggauuac                                                 20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 150
gtaatccttg tgggaggtac                                                 20

<210> SEQ ID NO 151
<211> LENGTH: 20
<212> TYPE: RNA
<213> ORGANISM: Homo sapiens

<400> SEQUENCE: 151
aaacaaaccu ggcuugaagu                                                 20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 152
```
acttcaagcc aggtttgttt                                              20

<210> SEQ ID NO 153
<211> LENGTH: 20
<212> TYPE: RNA
<213> ORGANISM: Homo sapiens

<400> SEQUENCE: 153
ucaaggcgau cgcagccaag                                              20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 154
cttggctgcg atcgccttga                                              20

<210> SEQ ID NO 155
<211> LENGTH: 20
<212> TYPE: RNA
<213> ORGANISM: Homo sapiens

<400> SEQUENCE: 155
auggcaagcc gucuccugcu                                              20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 156
agcaggagac ggcttgccat                                              20

<210> SEQ ID NO 157
<211> LENGTH: 20
<212> TYPE: RNA
<213> ORGANISM: Homo sapiens

<400> SEQUENCE: 157
gaucuuaaac aaaccuggcu                                              20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 158
agccaggttt gtttaagatc                                              20

<210> SEQ ID NO 159
<211> LENGTH: 20
<212> TYPE: RNA
<213> ORGANISM: Homo sapiens

<400> SEQUENCE: 159
ugaucuuaaa caaaccuggc                                           20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 160
gccaggtttg tttaagatca                                           20

<210> SEQ ID NO 161
<211> LENGTH: 20
<212> TYPE: RNA
<213> ORGANISM: Homo sapiens

<400> SEQUENCE: 161
uaaacaaacc uggcuugaag                                           20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 162
cttcaagcca ggtttgttta                                           20

<210> SEQ ID NO 163
<211> LENGTH: 20
<212> TYPE: RNA
<213> ORGANISM: Homo sapiens

<400> SEQUENCE: 163
aacaaaccug gcuugaagua                                           20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 164
tacttcaagc caggtttgtt                                           20

<210> SEQ ID NO 165
<211> LENGTH: 20
<212> TYPE: RNA
<213> ORGANISM: Homo sapiens

<400> SEQUENCE: 165
cucagcagug ggacagcaac                                           20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

```
<400> SEQUENCE: 166
gttgctgtcc cactgctgag                                              20

<210> SEQ ID NO 167
<211> LENGTH: 20
<212> TYPE: RNA
<213> ORGANISM: Homo sapiens

<400> SEQUENCE: 167
ucagcagugg gacagcaacc                                              20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 168
ggttgctgtc ccactgctga                                              20

<210> SEQ ID NO 169
<211> LENGTH: 20
<212> TYPE: RNA
<213> ORGANISM: Homo sapiens

<400> SEQUENCE: 169 cagcagugggg acagcaaccu                                             20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 170
aggttgctgt cccactgctg                                              20

<210> SEQ ID NO 171
<211> LENGTH: 20
<212> TYPE: RNA
<213> ORGANISM: Homo sapiens

<400> SEQUENCE: 171
agcaguggga cagcaaccug                                              20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 172
caggttgctg tcccactgct                                              20

<210> SEQ ID NO 173
<211> LENGTH: 20
<212> TYPE: RNA
<213> ORGANISM: Homo sapiens
```

```
<400> SEQUENCE: 173
gcagugggac agcaaccugu                                              20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 174
acaggttgct gtcccactgc                                              20

<210> SEQ ID NO 175
<211> LENGTH: 20
<212> TYPE: RNA
<213> ORGANISM: Homo sapiens

<400> SEQUENCE: 175
cagugggaca gcaaccugua                                              20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 176
tacaggttgc tgtcccactg                                              20

<210> SEQ ID NO 177
<211> LENGTH: 20
<212> TYPE: RNA
<213> ORGANISM: Homo sapiens

<400> SEQUENCE: 177
agugggacag caaccuguag                                              20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 178
ctacaggttg ctgtcccact                                              20

<210> SEQ ID NO 179
<211> LENGTH: 20
<212> TYPE: RNA
<213> ORGANISM: Homo sapiens

<400> SEQUENCE: 179
uguaccuccc acaaggauua                                              20

<210> SEQ ID NO 180
<211> LENGTH: 20
<212> TYPE: DNA
<213> ORGANISM: Artificial Sequence
```

```
<220> FEATURE:
<223> OTHER INFORMATION: Description of Artificial Sequence:
      Synthetic oligonucleotide

<400> SEQUENCE: 180
taatccttgt gggaggtaca                                              20

<210> SEQ ID NO 181
<211> LENGTH: 20
<212> TYPE: RNA
<213> ORGANISM: Homo sapiens

<400> SEQUENCE: 181
aagugaccua uaccuguguu                                              20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 182
aacacaggta taggtcactt                                              20

<210> SEQ ID NO 183
<211> LENGTH: 20
<212> TYPE: RNA
<213> ORGANISM: Homo sapiens

<400> SEQUENCE: 183
gugggacagc aaccuguaga                                              20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 184
tctacaggtt gctgtcccac                                              20

<210> SEQ ID NO 185
<211> LENGTH: 20
<212> TYPE: RNA
<213> ORGANISM: Homo sapiens

<400> SEQUENCE: 185
uagugccacu aacgguugag                                              20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 186
ctcaaccgtt agtggcacta                                              20

<210> SEQ ID NO 187
```

```
<211> LENGTH: 20
<212> TYPE: RNA
<213> ORGANISM: Homo sapiens

<400> SEQUENCE: 187
agugccacua acgguugagu                                           20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 188
actcaaccgt tagtggcact                                           20

<210> SEQ ID NO 189
<211> LENGTH: 20
<212> TYPE: RNA
<213> ORGANISM: Homo sapiens

<400> SEQUENCE: 189
agguggagau gaucuuaaac                                           20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 190
gtttaagatc atctccacct                                           20

<210> SEQ ID NO 191
<211> LENGTH: 20
<212> TYPE: RNA
<213> ORGANISM: Homo sapiens

<400> SEQUENCE: 191
ugggacagca accuguagag                                           20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 192
ctctacaggt tgctgtccca                                           20

<210> SEQ ID NO 193
<211> LENGTH: 20
<212> TYPE: RNA
<213> ORGANISM: Homo sapiens

<400> SEQUENCE: 193
auagugccac uaacgguuga                                           20

<210> SEQ ID NO 194
```

```
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 194
tcaaccgtta gtggcactat                                               20

<210> SEQ ID NO 195
<211> LENGTH: 20
<212> TYPE: RNA
<213> ORGANISM: Homo sapiens

<400> SEQUENCE: 195
caagugaccu auaccugugu                                               20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 196
acacaggtat aggtcacttg                                               20

<210> SEQ ID NO 197
<211> LENGTH: 20
<212> TYPE: RNA
<213> ORGANISM: Homo sapiens

<400> SEQUENCE: 197
agugaccuau accuguguuu                                               20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 198
aaacacaggt ataggtcact                                               20

<210> SEQ ID NO 199
<211> LENGTH: 20
<212> TYPE: RNA
<213> ORGANISM: Homo sapiens

<400> SEQUENCE: 199
gcaagccguc uccugcucaa                                               20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 200
ttgagcagga gacggcttgc                                               20
```

<210> SEQ ID NO 201
<211> LENGTH: 20
<212> TYPE: RNA
<213> ORGANISM: Homo sapiens

<400> SEQUENCE: 201
caagccgucu ccugcucaac                                              20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 202
gttgagcagg agacggcttg                                              20

<210> SEQ ID NO 203
<211> LENGTH: 20
<212> TYPE: RNA
<213> ORGANISM: Homo sapiens

<400> SEQUENCE: 203
aagccgucuc cugcucaaca                                              20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 204
tgttgagcag gagacggctt                                              20

<210> SEQ ID NO 205
<211> LENGTH: 20
<212> TYPE: RNA
<213> ORGANISM: Homo sapiens

<400> SEQUENCE: 205
ucuuaaacaa accuggcuug                                              20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 206
caagccaggt ttgtttaaga                                              20

<210> SEQ ID NO 207
<211> LENGTH: 20
<212> TYPE: RNA
<213> ORGANISM: Homo sapiens

<400> SEQUENCE: 207
ucugugacac cagaacgcau                                              20

```
<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 208
atgcgttctg gtgtcacaga                                              20

<210> SEQ ID NO 209
<211> LENGTH: 20
<212> TYPE: RNA
<213> ORGANISM: Homo sapiens

<400> SEQUENCE: 209
cugugacacc agaacgcauu                                              20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 210
aatgcgttct ggtgtcacag                                              20

<210> SEQ ID NO 211
<211> LENGTH: 20
<212> TYPE: RNA
<213> ORGANISM: Homo sapiens

<400> SEQUENCE: 211
ugugacacca gaacgcauug                                              20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 212
caatgcgttc tggtgtcaca                                              20

<210> SEQ ID NO 213
<211> LENGTH: 20
<212> TYPE: RNA
<213> ORGANISM: Homo sapiens

<400> SEQUENCE: 213
aacuucaacc aucuccaggu                                              20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide
```

```
<400> SEQUENCE: 214
acctggagat ggttgaagtt                                               20

<210> SEQ ID NO 215
<211> LENGTH: 20
<212> TYPE: RNA
<213> ORGANISM: Homo sapiens

<400> SEQUENCE: 215
acaaaccugg cuugaaguau                                               20

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 216
atacttcaag ccaggtttgt                                               20

<210> SEQ ID NO 217
<211> LENGTH: 20
<212> TYPE: RNA
<213> ORGANISM: Homo sapiens

<400> SEQUENCE: 217
uuaaccagau ugagugccac                                               20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 218
gtggcactca atctggttaa                                               20

<210> SEQ ID NO 219
<211> LENGTH: 20
<212> TYPE: RNA
<213> ORGANISM: Homo sapiens

<400> SEQUENCE: 219
gugacaccag aacgcauugc                                               20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 220
gcaatgcgtt ctggtgtcac                                               20

<210> SEQ ID NO 221
<211> LENGTH: 20
<212> TYPE: RNA
<213> ORGANISM: Homo sapiens
```

```
<400> SEQUENCE: 221
ugacaccaga acgcauugcu                                              20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 222
agcaatgcgt tctggtgtca                                              20

<210> SEQ ID NO 223
<211> LENGTH: 20
<212> TYPE: RNA
<213> ORGANISM: Homo sapiens

<400> SEQUENCE: 223
auuaccccuu ccaugaagag                                              20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 224
ctcttcatgg aagggtaat                                               20

<210> SEQ ID NO 225
<211> LENGTH: 20
<212> TYPE: RNA
<213> ORGANISM: Homo sapiens

<400> SEQUENCE: 225
gggacagcaa ccuguagagu                                              20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 226
actctacagg ttgctgtccc                                              20

<210> SEQ ID NO 227
<211> LENGTH: 20
<212> TYPE: RNA
<213> ORGANISM: Homo sapiens

<400> SEQUENCE: 227
auacccuuuu cugaccaaag                                              20

<210> SEQ ID NO 228
<211> LENGTH: 20
<212> TYPE: DNA
<213> ORGANISM: Artificial Sequence
<220> FEATURE:
```

-continued

```
<223> OTHER INFORMATION: Description of Artificial Sequence:
      Synthetic oligonucleotide

<400> SEQUENCE: 228
ctttggtcag aaaagggtat                                            20

<210> SEQ ID NO 229
<211> LENGTH: 20
<212> TYPE: RNA
<213> ORGANISM: Homo sapiens

<400> SEQUENCE: 229
aucaaggcga ucgcagccaa                                            20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 230
ttggctgcga tcgccttgat                                            20

<210> SEQ ID NO 231
<211> LENGTH: 20
<212> TYPE: RNA
<213> ORGANISM: Homo sapiens

<400> SEQUENCE: 231
agucugugac accagaacgc                                            20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 232
gcgttctggt gtcacagact                                            20

<210> SEQ ID NO 233
<211> LENGTH: 20
<212> TYPE: RNA
<213> ORGANISM: Homo sapiens

<400> SEQUENCE: 233
cuguaccucc cacaaggauu                                            20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 234
aatccttgtg ggaggtacag                                            20

<210> SEQ ID NO 235
<211> LENGTH: 20
```

```
<212> TYPE: RNA
<213> ORGANISM: Homo sapiens

<400> SEQUENCE: 235
cacaaggauu accccuucca                                              20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 236
tggaaggggt aatccttgtg                                              20

<210> SEQ ID NO 237
<211> LENGTH: 20
<212> TYPE: RNA
<213> ORGANISM: Homo sapiens

<400> SEQUENCE: 237
gauuaccccu uccaugaaga                                              20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 238
tcttcatgga agggtaatc                                               20

<210> SEQ ID NO 239
<211> LENGTH: 20
<212> TYPE: RNA
<213> ORGANISM: Homo sapiens

<400> SEQUENCE: 239
uuaccccuuc caugaagagu                                              20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 240
actcttcatg gaaggggtaa                                              20

<210> SEQ ID NO 241
<211> LENGTH: 20
<212> TYPE: RNA
<213> ORGANISM: Homo sapiens

<400> SEQUENCE: 241
uaccccuucc augaagaguu                                              20

<210> SEQ ID NO 242
<211> LENGTH: 20
```

-continued

```
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 242
aactcttcat ggaagggta                                                    20

<210> SEQ ID NO 243
<211> LENGTH: 20
<212> TYPE: RNA
<213> ORGANISM: Homo sapiens

<400> SEQUENCE: 243
cacccauauc ucacucagga                                                   20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 244
tcctgagtga gatatgggtg                                                   20

<210> SEQ ID NO 245
<211> LENGTH: 20
<212> TYPE: RNA
<213> ORGANISM: Homo sapiens

<400> SEQUENCE: 245
ggauuacccc uuccaugaag                                                   20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 246
cttcatggaa ggggtaatcc                                                   20

<210> SEQ ID NO 247
<211> LENGTH: 20
<212> TYPE: RNA
<213> ORGANISM: Homo sapiens

<400> SEQUENCE: 247
acucagcagu gggacagcaa                                                   20

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 248
ttgctgtccc actgctgagt                                                   20
```

<210> SEQ ID NO 249
<211> LENGTH: 20
<212> TYPE: RNA
<213> ORGANISM: Homo sapiens

<400> SEQUENCE: 249
aagccugcag uuaaccagau                                           20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 250
atctggttaa ctgcaggctt                                           20

<210> SEQ ID NO 251
<211> LENGTH: 20
<212> TYPE: RNA
<213> ORGANISM: Homo sapiens

<400> SEQUENCE: 251
gucugugaca ccagaacgca                                           20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 252
tgcgttctgg tgtcacagac                                           20

<210> SEQ ID NO 253
<211> LENGTH: 20
<212> TYPE: RNA
<213> ORGANISM: Homo sapiens

<400> SEQUENCE: 253
gcuguaccuc ccacaaggau                                           20

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 254
atccttgtgg gaggtacagc                                           20

<210> SEQ ID NO 255
<211> LENGTH: 20
<212> TYPE: RNA
<213> ORGANISM: Homo sapiens

<400> SEQUENCE: 255
aggauuaccc cuuccaugaa                                           20

-continued

```
<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 256
ttcatggaag gggtaatcct                                               20

<210> SEQ ID NO 257
<211> LENGTH: 20
<212> TYPE: RNA
<213> ORGANISM: Homo sapiens

<400> SEQUENCE: 257
agccugcagu uaaccagauu                                               20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 258
aatctggtta actgcaggct                                               20

<210> SEQ ID NO 259
<211> LENGTH: 20
<212> TYPE: RNA
<213> ORGANISM: Homo sapiens

<400> SEQUENCE: 259
ccaagugacc uauaccugug                                               20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 260
cacaggtata ggtcacttgg                                               20

<210> SEQ ID NO 261
<211> LENGTH: 20
<212> TYPE: RNA
<213> ORGANISM: Homo sapiens

<400> SEQUENCE: 261
acuucaacca ucuccaggug                                               20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 262
```

-continued cacctggaga tggttgaagt                                               20

<210> SEQ ID NO 263
<211> LENGTH: 20
<212> TYPE: RNA
<213> ORGANISM: Homo sapiens

<400> SEQUENCE: 263
uugagcugua ccucccacaa                                               20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 264
ttgtgggagg tacagctcaa                                               20

<210> SEQ ID NO 265
<211> LENGTH: 20
<212> TYPE: RNA
<213> ORGANISM: Homo sapiens

<400> SEQUENCE: 265
ugagcuguac cucccacaag                                               20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 266
cttgtgggag gtacagctca                                               20

<210> SEQ ID NO 267
<211> LENGTH: 20
<212> TYPE: RNA
<213> ORGANISM: Homo sapiens

<400> SEQUENCE: 267
gagcuguacc ucccacaagg                                               20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 268
ccttgtggga ggtacagctc                                               20

<210> SEQ ID NO 269
<211> LENGTH: 20
<212> TYPE: RNA
<213> ORGANISM: Homo sapiens

<400> SEQUENCE: 269

-continued agcuguaccu cccacaagga 20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 270
tccttgtggg aggtacagct 20

<210> SEQ ID NO 271
<211> LENGTH: 20
<212> TYPE: RNA
<213> ORGANISM: Homo sapiens

<400> SEQUENCE: 271
accccuucca ugaagaguuu 20

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 272
aaactcttca tggaaggggt 20

<210> SEQ ID NO 273
<211> LENGTH: 20
<212> TYPE: RNA
<213> ORGANISM: Homo sapiens

<400> SEQUENCE: 273
ggaaaguaca accugaauac 20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 274
gtattcaggt tgtactttcc 20

<210> SEQ ID NO 275
<211> LENGTH: 20
<212> TYPE: RNA
<213> ORGANISM: Homo sapiens

<400> SEQUENCE: 275
ggaauuuuuc ccauuggaug 20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence:

Synthetic oligonucleotide

<400> SEQUENCE: 276
catccaatgg gaaaaattcc                                          20

<210> SEQ ID NO 277
<211> LENGTH: 20
<212> TYPE: RNA
<213> ORGANISM: Homo sapiens

<400> SEQUENCE: 277
gguggagaug aucuuaaaca                                          20

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 278
tgtttaagat catctccacc                                          20

<210> SEQ ID NO 279
<211> LENGTH: 20
<212> TYPE: RNA
<213> ORGANISM: Homo sapiens

<400> SEQUENCE: 279
gccugcaguu aaccagauug                                          20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 280
caatctggtt aactgcaggc                                          20

<210> SEQ ID NO 281
<211> LENGTH: 20
<212> TYPE: RNA
<213> ORGANISM: Homo sapiens

<400> SEQUENCE: 281
acaaggauua ccccuuccau                                          20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 282
atggaagggg taatccttgt                                          20

<210> SEQ ID NO 283
<211> LENGTH: 20
<212> TYPE: RNA

<213> ORGANISM: Homo sapiens

<400> SEQUENCE: 283
agccgucucc ugcucaacaa                                               20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 284
ttgttgagca ggagacggct                                               20

<210> SEQ ID NO 285
<211> LENGTH: 20
<212> TYPE: RNA
<213> ORGANISM: Homo sapiens

<400> SEQUENCE: 285
auuggaugag ucgggcaaug                                               20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 286
cattgcccga ctcatccaat                                               20

<210> SEQ ID NO 287
<211> LENGTH: 20
<212> TYPE: RNA
<213> ORGANISM: Homo sapiens

<400> SEQUENCE: 287
uaagccugca guuaaccaga                                               20

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 288
tctggttaac tgcaggctta                                               20

<210> SEQ ID NO 289
<211> LENGTH: 20
<212> TYPE: RNA
<213> ORGANISM: Homo sapiens

<400> SEQUENCE: 289
ccccaagucu gugacaccag                                               20

<210> SEQ ID NO 290
<211> LENGTH: 20
<212> TYPE: DNA

```
<213> ORGANISM: Artificial Sequence
<220> FEATURE:
<223> OTHER INFORMATION: Description of Artificial Sequence:
      Synthetic oligonucleotide

<400> SEQUENCE: 290
ctggtgtcac agacttgggg                                                    20

<210> SEQ ID NO 291
<211> LENGTH: 20
<212> TYPE: RNA
<213> ORGANISM: Homo sapiens

<400> SEQUENCE: 291
gugaccuaua ccuguguuuc                                                    20

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 292
gaaacacagg tataggtcac                                                    20

<210> SEQ ID NO 293
<211> LENGTH: 20
<212> TYPE: RNA
<213> ORGANISM: Homo sapiens

<400> SEQUENCE: 293
ggacagcaac cuguagagug                                                    20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 294
cactctacag gttgctgtcc                                                    20

<210> SEQ ID NO 295
<211> LENGTH: 20
<212> TYPE: RNA
<213> ORGANISM: Homo sapiens

<400> SEQUENCE: 295
cuuaaacaaa ccuggcuuga                                                    20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 296
tcaagccagg tttgtttaag                                                    20
```

```
<210> SEQ ID NO 297
<211> LENGTH: 20
<212> TYPE: RNA
<213> ORGANISM: Homo sapiens

<400> SEQUENCE: 297
caauaaaacu acagcccagg                                              20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 298
cctgggctgt agttttattg                                              20

<210> SEQ ID NO 299
<211> LENGTH: 20
<212> TYPE: RNA
<213> ORGANISM: Homo sapiens

<400> SEQUENCE: 299
aagucuguga caccagaacg                                              20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 300
cgttctggtg tcacagactt                                              20

<210> SEQ ID NO 301
<211> LENGTH: 20
<212> TYPE: RNA
<213> ORGANISM: Homo sapiens

<400> SEQUENCE: 301
guugagcugu accucccaca                                              20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 302
tgtgggaggt acagctcaac                                              20

<210> SEQ ID NO 303
<211> LENGTH: 20
<212> TYPE: RNA
<213> ORGANISM: Homo sapiens

<400> SEQUENCE: 303
uacccuuuuc ugaccaaaga                                              20
```

```
<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 304
tctttggtca gaaaagggta                                          20

<210> SEQ ID NO 305
<211> LENGTH: 20
<212> TYPE: RNA
<213> ORGANISM: Homo sapiens

<400> SEQUENCE: 305
acccauaucu cacucaggag                                          20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 306
ctcctgagtg agatatgggt                                          20

<210> SEQ ID NO 307
<211> LENGTH: 20
<212> TYPE: RNA
<213> ORGANISM: Homo sapiens

<400> SEQUENCE: 307
auccccaagu cugugacacc                                          20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 308
ggtgtcacag acttggggat                                          20

<210> SEQ ID NO 309
<211> LENGTH: 20
<212> TYPE: RNA
<213> ORGANISM: Homo sapiens

<400> SEQUENCE: 309
uccccaaguc ugugacacca                                          20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 310
```

```
tggtgtcaca gacttgggga                                              20

<210> SEQ ID NO 311
<211> LENGTH: 20
<212> TYPE: RNA
<213> ORGANISM: Homo sapiens

<400> SEQUENCE: 311
caaggauuac cccuuccaug                                              20

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 312
catggaaggg gtaatccttg                                              20

<210> SEQ ID NO 313
<211> LENGTH: 20
<212> TYPE: RNA
<213> ORGANISM: Homo sapiens

<400> SEQUENCE: 313
aaggauuacc ccuuccauga                                              20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 314
tcatggaagg ggtaatcctt                                              20

<210> SEQ ID NO 315
<211> LENGTH: 20
<212> TYPE: RNA
<213> ORGANISM: Homo sapiens

<400> SEQUENCE: 315
aauagugcca cuaacgguug                                              20

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 316
caaccgttag tggcactatt                                              20

<210> SEQ ID NO 317
<211> LENGTH: 20
<212> TYPE: RNA
<213> ORGANISM: Homo sapiens

<400> SEQUENCE: 317
```

-continued uuggaugagu cgggcaaugu                          20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 318
acattgcccg actcatccaa                          20

<210> SEQ ID NO 319
<211> LENGTH: 20
<212> TYPE: RNA
<213> ORGANISM: Homo sapiens

<400> SEQUENCE: 319
caacuucaac caucuccagg                          20

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 320
cctggagatg gttgaagttg                          20

<210> SEQ ID NO 321
<211> LENGTH: 20
<212> TYPE: RNA
<213> ORGANISM: Homo sapiens

<400> SEQUENCE: 321
auaagccugc aguuaaccag                          20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 322
ctggttaact gcaggcttat                          20

<210> SEQ ID NO 323
<211> LENGTH: 20
<212> TYPE: RNA
<213> ORGANISM: Homo sapiens

<400> SEQUENCE: 323
ccugcaguua accagauuga                          20

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

```
<400> SEQUENCE: 324
tcaatctggt taactgcagg                                              20

<210> SEQ ID NO 325
<211> LENGTH: 20
<212> TYPE: RNA
<213> ORGANISM: Homo sapiens

<400> SEQUENCE: 325 gaucccaag ucugugacac                                               20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 326
gtgtcacaga cttggggatc                                              20

<210> SEQ ID NO 327
<211> LENGTH: 20
<212> TYPE: RNA
<213> ORGANISM: Homo sapiens

<400> SEQUENCE: 327
uguugagcug uaccucccac                                              20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 328
gtgggaggta cagctcaaca                                              20

<210> SEQ ID NO 329
<211> LENGTH: 20
<212> TYPE: RNA
<213> ORGANISM: Homo sapiens

<400> SEQUENCE: 329
cacucagcag ugggacagca                                              20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 330
tgctgtccca ctgctgagtg                                              20

<210> SEQ ID NO 331
<211> LENGTH: 20
<212> TYPE: RNA
<213> ORGANISM: Homo sapiens
```

-continued

<400> SEQUENCE: 331
uggaugaguc gggcaaugug                                                    20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 332
cacattgccc gactcatcca                                                    20

<210> SEQ ID NO 333
<211> LENGTH: 20
<212> TYPE: RNA
<213> ORGANISM: Homo sapiens

<400> SEQUENCE: 333
aaugugguuc ccagugacac                                                    20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 334
gtgtcactgg gaaccacatt                                                    20

<210> SEQ ID NO 335
<211> LENGTH: 20
<212> TYPE: RNA
<213> ORGANISM: Homo sapiens

<400> SEQUENCE: 335
gaucaaggcg aucgcagcca                                                    20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 336
tggctgcgat cgccttgatc                                                    20

<210> SEQ ID NO 337
<211> LENGTH: 20
<212> TYPE: RNA
<213> ORGANISM: Homo sapiens

<400> SEQUENCE: 337
ucgcagccaa gcacaauaaa                                                    20

<210> SEQ ID NO 338
<211> LENGTH: 20
<212> TYPE: DNA
<213> ORGANISM: Artificial Sequence

```
<220> FEATURE:
<223> OTHER INFORMATION: Description of Artificial Sequence:
      Synthetic oligonucleotide

<400> SEQUENCE: 338
tttattgtgc ttggctgcga                                            20

<210> SEQ ID NO 339
<211> LENGTH: 20
<212> TYPE: RNA
<213> ORGANISM: Homo sapiens

<400> SEQUENCE: 339
cgcagccaag cacaauaaaa                                            20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 340
ttttattgtg cttggctgcg                                            20

<210> SEQ ID NO 341
<211> LENGTH: 20
<212> TYPE: RNA
<213> ORGANISM: Homo sapiens

<400> SEQUENCE: 341
gcccuucuuu cuacccugcu                                            20

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 342
agcagggtag aaagaagggc                                            20

<210> SEQ ID NO 343
<211> LENGTH: 20
<212> TYPE: RNA
<213> ORGANISM: Homo sapiens

<400> SEQUENCE: 343
gaccucacgg gcuauuuaaa                                            20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 344
tttaaatagc ccgtgaggtc                                            20

<210> SEQ ID NO 345
```

```
<211> LENGTH: 20
<212> TYPE: RNA
<213> ORGANISM: Homo sapiens

<400> SEQUENCE: 345
uaccucccac aaggauuacc                                               20

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 346
ggtaatcctt gtgggaggta                                               20

<210> SEQ ID NO 347
<211> LENGTH: 20
<212> TYPE: RNA
<213> ORGANISM: Homo sapiens

<400> SEQUENCE: 347
cccuucuuuc uacccugcug                                               20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 348
cagcagggta gaaagaaggg                                               20

<210> SEQ ID NO 349
<211> LENGTH: 20
<212> TYPE: RNA
<213> ORGANISM: Homo sapiens

<400> SEQUENCE: 349
accucccaca aggauuaccc                                               20

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 350
gggtaatcct tgtgggaggt                                               20

<210> SEQ ID NO 351
<211> LENGTH: 20
<212> TYPE: RNA
<213> ORGANISM: Homo sapiens

<400> SEQUENCE: 351
accucacggg cuauuuaaag                                               20

<210> SEQ ID NO 352
```

```
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 352
ctttaaatag cccgtgaggt                                              20

<210> SEQ ID NO 353
<211> LENGTH: 20
<212> TYPE: RNA
<213> ORGANISM: Homo sapiens

<400> SEQUENCE: 353
auugagugcc acccauaucu                                              20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 354
agatatgggt ggcactcaat                                              20

<210> SEQ ID NO 355
<211> LENGTH: 20
<212> TYPE: RNA
<213> ORGANISM: Homo sapiens

<400> SEQUENCE: 355
gaucuuaaac aaaccuggcu                                              20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 356
agccaggttt gtttaagatc                                              20

<210> SEQ ID NO 357
<211> LENGTH: 20
<212> TYPE: RNA
<213> ORGANISM: Homo sapiens

<400> SEQUENCE: 357
ugaucuuaaa caaaccuggc                                              20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 358
gccaggtttg tttaagatca                                              20
```

```
<210> SEQ ID NO 359
<211> LENGTH: 20
<212> TYPE: RNA
<213> ORGANISM: Homo sapiens

<400> SEQUENCE: 359
aaggcgaucg cagccaagca                                                   20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 360
tgcttggctg cgatcgcctt                                                   20

<210> SEQ ID NO 361
<211> LENGTH: 20
<212> TYPE: RNA
<213> ORGANISM: Homo sapiens

<400> SEQUENCE: 361
gauugagugc cacccauauc                                                   20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 362
gatatgggtg gcactcaatc                                                   20

<210> SEQ ID NO 363
<211> LENGTH: 20
<212> TYPE: RNA
<213> ORGANISM: Homo sapiens

<400> SEQUENCE: 363
cagauugagu gccacccaua                                                   20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 364
tatgggtggc actcaatctg                                                   20

<210> SEQ ID NO 365
<211> LENGTH: 20
<212> TYPE: RNA
<213> ORGANISM: Homo sapiens

<400> SEQUENCE: 365
ccagauugag ugccacccau                                                   20
```

-continued

```
<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 366
atgggtggca ctcaatctgg                                              20

<210> SEQ ID NO 367
<211> LENGTH: 20
<212> TYPE: RNA
<213> ORGANISM: Homo sapiens

<400> SEQUENCE: 367
ucaaggcgau cgcagccaag                                              20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 368
cttggctgcg atcgccttga                                              20

<210> SEQ ID NO 369
<211> LENGTH: 20
<212> TYPE: RNA
<213> ORGANISM: Homo sapiens

<400> SEQUENCE: 369
uaaacaaacc uggcuugaag                                              20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 370
cttcaagcca ggtttgttta                                              20

<210> SEQ ID NO 371
<211> LENGTH: 20
<212> TYPE: RNA
<213> ORGANISM: Homo sapiens

<400> SEQUENCE: 371
uuaccccuuc caugaagagu                                              20

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide
```

```
<400> SEQUENCE: 372
actcttcatg gaagggtaa                                              20

<210> SEQ ID NO 373
<211> LENGTH: 20
<212> TYPE: RNA
<213> ORGANISM: Homo sapiens

<400> SEQUENCE: 373
aaacaaaccu ggcuugaagu                                             20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 374
acttcaagcc aggtttgttt                                             20

<210> SEQ ID NO 375
<211> LENGTH: 20
<212> TYPE: RNA
<213> ORGANISM: Homo sapiens

<400> SEQUENCE: 375
uaccccuucc augaagaguu                                             20

<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 376
aactcttcat ggaagggta                                              20

<210> SEQ ID NO 377
<211> LENGTH: 20
<212> TYPE: RNA
<213> ORGANISM: Homo sapiens

<400> SEQUENCE: 377
aauacaaaaa uuagcccggc                                             20

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 378
gccgggctaa ttttgtatt                                              20

<210> SEQ ID NO 379
<211> LENGTH: 20
<212> TYPE: RNA
<213> ORGANISM: Homo sapiens
```

-continued

<400> SEQUENCE: 379
aauaccaucu ccucuucggc                                          20

<210> SEQ ID NO 380
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 380
gccgaagagg agatggtatt                                          20

<210> SEQ ID NO 381
<211> LENGTH: 20
<212> TYPE: RNA
<213> ORGANISM: Homo sapiens

<400> SEQUENCE: 381
aaauaccauc uccucuucgg                                          20

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 382
ccgaagagga gatggtattt                                          20

<210> SEQ ID NO 383
<211> LENGTH: 20
<212> TYPE: RNA
<213> ORGANISM: Homo sapiens

<400> SEQUENCE: 383
auaccaucuc cucuucggcu                                          20

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 384
agccgaagag gagatggtat                                          20

<210> SEQ ID NO 385
<211> LENGTH: 20
<212> TYPE: RNA
<213> ORGANISM: Homo sapiens

<400> SEQUENCE: 385
cacuacccuu auucuugucu                                          20

<210> SEQ ID NO 386
<211> LENGTH: 20
<212> TYPE: DNA
<213> ORGANISM: Artificial Sequence
<220> FEATURE:

```
<223> OTHER INFORMATION: Description of Artificial Sequence:
      Synthetic oligonucleotide

<400> SEQUENCE: 386
agacaagaat aagggtagtg                                              20

<210> SEQ ID NO 387
<211> LENGTH: 20
<212> TYPE: RNA
<213> ORGANISM: Homo sapiens

<400> SEQUENCE: 387
auacaaaaau uagcccggca                                              20

<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 388
tgccgggcta atttttgtat                                              20

<210> SEQ ID NO 389
<211> LENGTH: 20
<212> TYPE: RNA
<213> ORGANISM: Homo sapiens

<400> SEQUENCE: 389
ucacuacccu uauucuuguc                                              20

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 390
gacaagaata agggtagtga                                              20

<210> SEQ ID NO 391
<211> LENGTH: 20
<212> TYPE: RNA
<213> ORGANISM: Homo sapiens

<400> SEQUENCE: 391
uaccaucucc ucuucggcug                                              20

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 392
cagccgaaga ggagatggta                                              20

<210> SEQ ID NO 393
<211> LENGTH: 20
```

-continued

<212> TYPE: RNA
<213> ORGANISM: Homo sapiens

<400> SEQUENCE: 393
acacccauuc agucauuuug                                               20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 394
caaaatgact gaatgggtgt                                               20

<210> SEQ ID NO 395
<211> LENGTH: 20
<212> TYPE: RNA
<213> ORGANISM: Homo sapiens

<400> SEQUENCE: 395
gacacccauu cagucauuuu                                               20

<210> SEQ ID NO 396
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 396
aaaatgactg aatgggtgtc                                               20

<210> SEQ ID NO 397
<211> LENGTH: 20
<212> TYPE: RNA
<213> ORGANISM: Homo sapiens

<400> SEQUENCE: 397
ucaugauaau cucccagaac                                               20

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 398
gttctgggag attatcatga                                               20

<210> SEQ ID NO 399
<211> LENGTH: 20
<212> TYPE: RNA
<213> ORGANISM: Homo sapiens

<400> SEQUENCE: 399
caguuuaucu uaucgcuccu                                               20

<210> SEQ ID NO 400
<211> LENGTH: 20

```
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 400
aggagcgata agataaactg                                              20

<210> SEQ ID NO 401
<211> LENGTH: 20
<212> TYPE: RNA
<213> ORGANISM: Homo sapiens

<400> SEQUENCE: 401
aguuuaucuu aucgcuccuc                                              20

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 402
gaggagcgat aagataaact                                              20

<210> SEQ ID NO 403
<211> LENGTH: 20
<212> TYPE: RNA
<213> ORGANISM: Homo sapiens

<400> SEQUENCE: 403
accucccaca aggauuaccc                                              20

<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 404
gggtaatcct tgtgggaggt                                              20

<210> SEQ ID NO 405
<211> LENGTH: 20
<212> TYPE: RNA
<213> ORGANISM: Homo sapiens

<400> SEQUENCE: 405
ccucccacaa ggauuacccc                                              20

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 406
ggggtaatcc ttgtgggagg                                              20
```

<210> SEQ ID NO 407
<211> LENGTH: 20
<212> TYPE: RNA
<213> ORGANISM: Homo sapiens

<400> SEQUENCE: 407
caugagguca gaagauagag                                               20

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 408
ctctatcttc tgacctcatg                                               20

<210> SEQ ID NO 409
<211> LENGTH: 20
<212> TYPE: RNA
<213> ORGANISM: Homo sapiens

<400> SEQUENCE: 409
cuucaugaua aucucccaga                                               20

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 410
tctgggagat tatcatgaag                                               20

<210> SEQ ID NO 411
<211> LENGTH: 20
<212> TYPE: RNA
<213> ORGANISM: Homo sapiens

<400> SEQUENCE: 411
augaggucag aagauagaga                                               20

<210> SEQ ID NO 412
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 412
tctctatctt ctgacctcat                                               20

<210> SEQ ID NO 413
<211> LENGTH: 20
<212> TYPE: RNA
<213> ORGANISM: Homo sapiens

<400> SEQUENCE: 413
acuguuuucu ccuuucuccu                                               20

```
<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 414
aggagaaagg agaaaacagt                                                      20

<210> SEQ ID NO 415
<211> LENGTH: 20
<212> TYPE: RNA
<213> ORGANISM: Homo sapiens

<400> SEQUENCE: 415
uucuccuuuc uccugacagc                                                      20

<210> SEQ ID NO 416
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 416
gctgtcagga gaaaggagaa                                                      20

<210> SEQ ID NO 417
<211> LENGTH: 20
<212> TYPE: RNA
<213> ORGANISM: Homo sapiens

<400> SEQUENCE: 417
agacccagcc uccuuucccu                                                      20

<210> SEQ ID NO 418
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 418
agggaaagga ggctgggtct                                                      20

<210> SEQ ID NO 419
<211> LENGTH: 20
<212> TYPE: RNA
<213> ORGANISM: Homo sapiens

<400> SEQUENCE: 419
cccuuauucu ugucugagcu                                                      20

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 420
```

```
agctcagaca agaataaggg                                           20

<210> SEQ ID NO 421
<211> LENGTH: 20
<212> TYPE: RNA
<213> ORGANISM: Homo sapiens

<400> SEQUENCE: 421
cucucccauu cauccgucuu                                           20

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 422
aagacggatg aatgggagag                                           20

<210> SEQ ID NO 423
<211> LENGTH: 20
<212> TYPE: RNA
<213> ORGANISM: Homo sapiens

<400> SEQUENCE: 423
caugauaauc ucccagaacc                                           20

<210> SEQ ID NO 424
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 424
ggttctggga gattatcatg                                           20

<210> SEQ ID NO 425
<211> LENGTH: 20
<212> TYPE: RNA
<213> ORGANISM: Homo sapiens

<400> SEQUENCE: 425
ucucucccau ucauccgucu                                           20

<210> SEQ ID NO 426
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 426
agacggatga atgggagaga                                           20

<210> SEQ ID NO 427
<211> LENGTH: 20
<212> TYPE: RNA
<213> ORGANISM: Homo sapiens

<400> SEQUENCE: 427
```
ccuuauucuu gucugagcuc                                               20

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 428
gagctcagac aagaataagg                                               20

<210> SEQ ID NO 429
<211> LENGTH: 20
<212> TYPE: RNA
<213> ORGANISM: Homo sapiens

<400> SEQUENCE: 429
ucucucacua cccuuauucu                                               20

<210> SEQ ID NO 430
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 430
agaataaggg tagtgagaga                                               20

<210> SEQ ID NO 431
<211> LENGTH: 20
<212> TYPE: RNA
<213> ORGANISM: Homo sapiens

<400> SEQUENCE: 431
ccuuucuugc ccucucuguc                                               20

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 432
gacagagagg gcaagaaagg                                               20

<210> SEQ ID NO 433
<211> LENGTH: 20
<212> TYPE: RNA
<213> ORGANISM: Homo sapiens

<400> SEQUENCE: 433
ccaaucuguc cauuccauuu                                               20

<210> SEQ ID NO 434
<211> LENGTH: 20
<212> TYPE: DNA
<213> ORGANISM: Artificial Sequence
<220> FEATURE:
<223> OTHER INFORMATION: Description of Artificial Sequence:

Synthetic oligonucleotide

<400> SEQUENCE: 434
aaatggaatg gacagattgg                                           20

<210> SEQ ID NO 435
<211> LENGTH: 20
<212> TYPE: RNA
<213> ORGANISM: Homo sapiens

<400> SEQUENCE: 435
cucucuccuu uaguacuucc                                           20

<210> SEQ ID NO 436
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 436
ggaagtacta aaggagagag                                           20

<210> SEQ ID NO 437
<211> LENGTH: 20
<212> TYPE: RNA
<213> ORGANISM: Homo sapiens

<400> SEQUENCE: 437
ucucuccuuu aguacuuccu                                           20

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 438
aggaagtact aaaggagaga                                           20

<210> SEQ ID NO 439
<211> LENGTH: 20
<212> TYPE: RNA
<213> ORGANISM: Homo sapiens

<400> SEQUENCE: 439
ccugagccug auuaucugaa                                           20

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 440
ttcagataat caggctcagg                                           20

<210> SEQ ID NO 441
<211> LENGTH: 20
<212> TYPE: RNA

```
<213> ORGANISM: Homo sapiens

<400> SEQUENCE: 441
ccaucuuuug ccaugaucac                                              20

<210> SEQ ID NO 442
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 442
gtgatcatgg caaaagatgg                                              20

<210> SEQ ID NO 443
<211> LENGTH: 20
<212> TYPE: RNA
<213> ORGANISM: Homo sapiens

<400> SEQUENCE: 443
uuucuccauc uuuugccaug                                              20

<210> SEQ ID NO 444
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 444
catggcaaaa gatggagaaa                                              20

<210> SEQ ID NO 445
<211> LENGTH: 20
<212> TYPE: RNA
<213> ORGANISM: Homo sapiens

<400> SEQUENCE: 445
gccaaucugu ccauuccauu                                              20

<210> SEQ ID NO 446
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 446
aatggaatgg acagattggc                                              20

<210> SEQ ID NO 447
<211> LENGTH: 20
<212> TYPE: RNA
<213> ORGANISM: Homo sapiens

<400> SEQUENCE: 447
uccaucuuuu gccaugauca                                              20

<210> SEQ ID NO 448
<211> LENGTH: 20
<212> TYPE: DNA
```

```
<213> ORGANISM: Artificial Sequence
<220> FEATURE:
<223> OTHER INFORMATION: Description of Artificial Sequence:
      Synthetic oligonucleotide

<400> SEQUENCE: 448
tgatcatggc aaaagatgga                                            20

<210> SEQ ID NO 449
<211> LENGTH: 20
<212> TYPE: RNA
<213> ORGANISM: Homo sapiens

<400> SEQUENCE: 449
cugagccuga uuaucugaaa                                            20

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 450
tttcagataa tcaggctcag                                            20

<210> SEQ ID NO 451
<211> LENGTH: 20
<212> TYPE: RNA
<213> ORGANISM: Homo sapiens

<400> SEQUENCE: 451
cuucuucgug accucuugca                                            20

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 452
tgcaagaggt cacgaagaag                                            20

<210> SEQ ID NO 453
<211> LENGTH: 20
<212> TYPE: RNA
<213> ORGANISM: Homo sapiens

<400> SEQUENCE: 453
auugacuucc ccaaacaaca                                            20

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 454
tgttgtttgg ggaagtcaat                                            20
```

```
<210> SEQ ID NO 455
<211> LENGTH: 20
<212> TYPE: RNA
<213> ORGANISM: Homo sapiens

<400> SEQUENCE: 455
cuagaaaaac cucucacaac                                               20

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 456
gttgtgagag gttttctag                                                20

<210> SEQ ID NO 457
<211> LENGTH: 20
<212> TYPE: RNA
<213> ORGANISM: Homo sapiens

<400> SEQUENCE: 457
uugacuuccc caaacaacag                                               20

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 458
ctgttgtttg gggaagtcaa                                               20

<210> SEQ ID NO 459
<211> LENGTH: 20
<212> TYPE: RNA
<213> ORGANISM: Homo sapiens

<400> SEQUENCE: 459
uagccugagc cugauuaucu                                               20

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 460
agataatcag gctcaggcta                                               20

<210> SEQ ID NO 461
<211> LENGTH: 20
<212> TYPE: RNA
<213> ORGANISM: Homo sapiens

<400> SEQUENCE: 461
aacguaucac ccacggccau                                               20
```

```
<210> SEQ ID NO 462
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 462
atggccgtgg gtgatacgtt                                               20

<210> SEQ ID NO 463
<211> LENGTH: 20
<212> TYPE: RNA
<213> ORGANISM: Homo sapiens

<400> SEQUENCE: 463
acacucaaua cagcuacacu                                               20

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 464
agtgtagctg tattgagtgt                                               20

<210> SEQ ID NO 465
<211> LENGTH: 20
<212> TYPE: RNA
<213> ORGANISM: Homo sapiens

<400> SEQUENCE: 465
gcuucuucgu gaccucuugc                                               20

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 466
gcaagaggtc acgaagaagc                                               20

<210> SEQ ID NO 467
<211> LENGTH: 20
<212> TYPE: RNA
<213> ORGANISM: Homo sapiens

<400> SEQUENCE: 467
auagccugag ccugauuauc                                               20

<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 468
```
gataatcagg ctcaggctat                                              20

<210> SEQ ID NO 469
<211> LENGTH: 20
<212> TYPE: RNA
<213> ORGANISM: Homo sapiens

<400> SEQUENCE: 469
guaacuagca agaccuguaa                                              20

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 470
ttacaggtct tgctagttac                                              20

<210> SEQ ID NO 471
<211> LENGTH: 20
<212> TYPE: RNA
<213> ORGANISM: Homo sapiens

<400> SEQUENCE: 471
auaagcaucu caagccggua                                              20

<210> SEQ ID NO 472
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 472
taccggcttg agatgcttat                                              20

<210> SEQ ID NO 473
<211> LENGTH: 20
<212> TYPE: RNA
<213> ORGANISM: Homo sapiens

<400> SEQUENCE: 473
aaacguauca cccacggcca                                              20

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 474
tggccgtggg tgatacgttt                                              20

<210> SEQ ID NO 475
<211> LENGTH: 20
<212> TYPE: RNA
<213> ORGANISM: Homo sapiens

<400> SEQUENCE: 475

```
ccguagcuag uugauaauuc                                              20

<210> SEQ ID NO 476
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 476
gaattatcaa ctagctacgg                                              20

<210> SEQ ID NO 477
<211> LENGTH: 20
<212> TYPE: RNA
<213> ORGANISM: Homo sapiens

<400> SEQUENCE: 477
auuuguuucu accccagcuc                                              20

<210> SEQ ID NO 478
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 478
gagctggggt agaaacaaat                                              20

<210> SEQ ID NO 479
<211> LENGTH: 20
<212> TYPE: RNA
<213> ORGANISM: Homo sapiens

<400> SEQUENCE: 479
aauaagcauc ucaagccggu                                              20

<210> SEQ ID NO 480
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 480
accggcttga gatgcttatt                                              20

<210> SEQ ID NO 481
<211> LENGTH: 20
<212> TYPE: RNA
<213> ORGANISM: Homo sapiens

<400> SEQUENCE: 481
uuuguuucua ccccagcucu                                              20

<210> SEQ ID NO 482
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide
```

```
<400> SEQUENCE: 482
agagctgggg tagaaacaaa                                            20

<210> SEQ ID NO 483
<211> LENGTH: 20
<212> TYPE: RNA
<213> ORGANISM: Homo sapiens

<400> SEQUENCE: 483
acguaucacc cacggccaua                                            20

<210> SEQ ID NO 484
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 484
tatggccgtg ggtgatacgt                                            20

<210> SEQ ID NO 485
<211> LENGTH: 20
<212> TYPE: RNA
<213> ORGANISM: Homo sapiens

<400> SEQUENCE: 485
uaaaaccuca acaccacaca                                            20

<210> SEQ ID NO 486
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 486
tgtgtggtgt tgaggtttta                                            20

<210> SEQ ID NO 487
<211> LENGTH: 20
<212> TYPE: RNA
<213> ORGANISM: Homo sapiens

<400> SEQUENCE: 487
guccccucuu aacccacacc                                            20

<210> SEQ ID NO 488
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 488
ggtgtgggtt aagaggggac                                            20

<210> SEQ ID NO 489
<211> LENGTH: 20
<212> TYPE: RNA
<213> ORGANISM: Homo sapiens
```

-continued

```
<400> SEQUENCE: 489
gucucagcuc cagcccguuu                                               20

<210> SEQ ID NO 490
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 490
aaacgggctg gagctgagac                                               20

<210> SEQ ID NO 491
<211> LENGTH: 20
<212> TYPE: RNA
<213> ORGANISM: Homo sapiens

<400> SEQUENCE: 491
agucucagcu ccagcccguu                                               20

<210> SEQ ID NO 492
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 492
aacgggctgg agctgagact                                               20

<210> SEQ ID NO 493
<211> LENGTH: 20
<212> TYPE: RNA
<213> ORGANISM: Homo sapiens

<400> SEQUENCE: 493
aaaaccucaa caccacacag                                               20

<210> SEQ ID NO 494
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 494
ctgtgtggtg ttgaggtttt                                               20

<210> SEQ ID NO 495
<211> LENGTH: 20
<212> TYPE: RNA
<213> ORGANISM: Homo sapiens

<400> SEQUENCE: 495
cccguagcua guugauaauu                                               20

<210> SEQ ID NO 496
<211> LENGTH: 20
<212> TYPE: DNA
<213> ORGANISM: Artificial Sequence
```

```
<220> FEATURE:
<223> OTHER INFORMATION: Description of Artificial Sequence:
      Synthetic oligonucleotide

<400> SEQUENCE: 496
aattatcaac tagctacggg                                              20

<210> SEQ ID NO 497
<211> LENGTH: 20
<212> TYPE: RNA
<213> ORGANISM: Homo sapiens

<400> SEQUENCE: 497
uaguguccau gucuccgucu                                              20

<210> SEQ ID NO 498
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 498
agacggagac atggacacta                                              20

<210> SEQ ID NO 499
<211> LENGTH: 20
<212> TYPE: RNA
<213> ORGANISM: Homo sapiens

<400> SEQUENCE: 499
cucacaacca uucacagcau                                              20

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 500
atgctgtgaa tggttgtgag                                              20

<210> SEQ ID NO 501
<211> LENGTH: 20
<212> TYPE: RNA
<213> ORGANISM: Homo sapiens

<400> SEQUENCE: 501
acaaccauuc acagcaucau                                              20

<210> SEQ ID NO 502
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 502
atgatgctgt gaatggttgt                                              20

<210> SEQ ID NO 503
```

```
<211> LENGTH: 20
<212> TYPE: RNA
<213> ORGANISM: Homo sapiens

<400> SEQUENCE: 503
gcauuuuguu auucuguccc                                              20

<210> SEQ ID NO 504
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 504
gggacagaat aacaaaatgc                                              20

<210> SEQ ID NO 505
<211> LENGTH: 20
<212> TYPE: RNA
<213> ORGANISM: Homo sapiens

<400> SEQUENCE: 505
uccgucugac agucucagcu                                              20

<210> SEQ ID NO 506
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 506
agctgagact gtcagacgga                                              20

<210> SEQ ID NO 507
<211> LENGTH: 20
<212> TYPE: RNA
<213> ORGANISM: Homo sapiens

<400> SEQUENCE: 507
cauuccauuu uguguccucu                                              20

<210> SEQ ID NO 508
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 508
agaggacaca aaatggaatg                                              20

<210> SEQ ID NO 509
<211> LENGTH: 20
<212> TYPE: RNA
<213> ORGANISM: Homo sapiens

<400> SEQUENCE: 509
uuagaguccc gugcugauga                                              20

<210> SEQ ID NO 510
```

```
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 510
tcatcagcac gggactctaa                                                  20

<210> SEQ ID NO 511
<211> LENGTH: 20
<212> TYPE: RNA
<213> ORGANISM: Homo sapiens

<400> SEQUENCE: 511
guuuuauugc accacagcau                                                  20

<210> SEQ ID NO 512
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 512
atgctgtggt gcaataaaac                                                  20

<210> SEQ ID NO 513
<211> LENGTH: 20
<212> TYPE: RNA
<213> ORGANISM: Homo sapiens

<400> SEQUENCE: 513
uaagcaucuc aagccgguag                                                  20

<210> SEQ ID NO 514
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 514
ctaccggctt gagatgctta                                                  20

<210> SEQ ID NO 515
<211> LENGTH: 20
<212> TYPE: RNA
<213> ORGANISM: Homo sapiens

<400> SEQUENCE: 515
ugcccucaca accauucaca                                                  20

<210> SEQ ID NO 516
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 516
tgtgaatggt tgtgagggca                                                  20
```

```
<210> SEQ ID NO 517
<211> LENGTH: 20
<212> TYPE: RNA
<213> ORGANISM: Homo sapiens

<400> SEQUENCE: 517
uaucacccac ggccauacag                                              20

<210> SEQ ID NO 518
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 518
ctgtatggcc gtgggtgata                                              20

<210> SEQ ID NO 519
<211> LENGTH: 20
<212> TYPE: RNA
<213> ORGANISM: Homo sapiens

<400> SEQUENCE: 519
augacaccaa gcuaauuucc                                              20

<210> SEQ ID NO 520
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 520
ggaaattagc ttggtgtcat                                              20

<210> SEQ ID NO 521
<211> LENGTH: 20
<212> TYPE: RNA
<213> ORGANISM: Homo sapiens

<400> SEQUENCE: 521
uuauugcacc acagcauauc                                              20

<210> SEQ ID NO 522
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 522
gatatgctgt ggtgcaataa                                              20

<210> SEQ ID NO 523
<211> LENGTH: 20
<212> TYPE: RNA
<213> ORGANISM: Homo sapiens

<400> SEQUENCE: 523
gcaugggcuc uuagauuaau                                              20
```

<210> SEQ ID NO 524
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 524
attaatctaa gagcccatgc                                                    20

<210> SEQ ID NO 525
<211> LENGTH: 20
<212> TYPE: RNA
<213> ORGANISM: Homo sapiens

<400> SEQUENCE: 525
auuccauuuu guguccucug                                                    20

<210> SEQ ID NO 526
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 526
cagaggacac aaaatggaat                                                    20

<210> SEQ ID NO 527
<211> LENGTH: 20
<212> TYPE: RNA
<213> ORGANISM: Homo sapiens

<400> SEQUENCE: 527
ggcuaaucuu uuucuuccc                                                     20

<210> SEQ ID NO 528
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 528
gggaagaaaa aagattagcc                                                    20

<210> SEQ ID NO 529
<211> LENGTH: 20
<212> TYPE: RNA
<213> ORGANISM: Homo sapiens

<400> SEQUENCE: 529
acagaugcuc gacagaagau                                                    20

<210> SEQ ID NO 530
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

```
<400> SEQUENCE: 530
atcttctgtc gagcatctgt                                                    20

<210> SEQ ID NO 531
<211> LENGTH: 20
<212> TYPE: RNA
<213> ORGANISM: Homo sapiens

<400> SEQUENCE: 531
gaugcucgac agaagaugug                                                    20

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 532
cacatcttct gtcgagcatc                                                    20

<210> SEQ ID NO 533
<211> LENGTH: 20
<212> TYPE: RNA
<213> ORGANISM: Homo sapiens

<400> SEQUENCE: 533 uuguuccuc caaaaacucc                                                     20

<210> SEQ ID NO 534
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 534 ggagttttg gaggaaacaa                                                     20

<210> SEQ ID NO 535
<211> LENGTH: 20
<212> TYPE: RNA
<213> ORGANISM: Homo sapiens

<400> SEQUENCE: 535
guacuuaacc uauguaggcu                                                    20

<210> SEQ ID NO 536
<211> LENGTH: 20
<212> TYPE: DNA
<213> ORGANISM: Artificial Sequence
<220> FEATURE:
<223> OTHER INFORMATION: Description of Artificial Sequence:
      Synthetic oligonucleotide

<400> SEQUENCE: 536
agcctacata ggttaagtac                                                    20

<210> SEQ ID NO 537
<211> LENGTH: 7
<212> TYPE: PRT
<213> ORGANISM: Homo sapiens
```

```
<400> SEQUENCE: 537

Pro Asn Asn Leu Ser Leu Val
1               5

<210> SEQ ID NO 538
<211> LENGTH: 7
<212> TYPE: PRT
<213> ORGANISM: Macaca mulatta

<400> SEQUENCE: 538

Pro Lys Asn Leu Ser Leu Val
1               5

<210> SEQ ID NO 539
<211> LENGTH: 7
<212> TYPE: PRT
<213> ORGANISM: Mus musculus

<400> SEQUENCE: 539

Gly Glu Asn Leu Ser Leu Val
1               5

<210> SEQ ID NO 540
<211> LENGTH: 7
<212> TYPE: PRT
<213> ORGANISM: Canis lupus familiaris

<400> SEQUENCE: 540

Ala Glu Asn Leu Thr Leu Val
1               5

<210> SEQ ID NO 541
<211> LENGTH: 7
<212> TYPE: PRT
<213> ORGANISM: Drosophila sp.

<400> SEQUENCE: 541

Lys Asp Asn Leu Thr Ala Val
1               5

<210> SEQ ID NO 542
<211> LENGTH: 7
<212> TYPE: PRT
<213> ORGANISM: Homo sapiens

<400> SEQUENCE: 542

Lys Met Gly Arg Tyr Asn Leu
1               5

<210> SEQ ID NO 543
<211> LENGTH: 7
<212> TYPE: PRT
<213> ORGANISM: Homo sapiens

<400> SEQUENCE: 543

Glu Glu Gly Ala Leu Ile Glu
1               5

<210> SEQ ID NO 544
<211> LENGTH: 7
<212> TYPE: PRT
<213> ORGANISM: Homo sapiens

<400> SEQUENCE: 544
```

```
Lys Pro Leu Val Thr His Arg
1               5

<210> SEQ ID NO 545
<211> LENGTH: 7
<212> TYPE: PRT
<213> ORGANISM: Macaca mulatta

<400> SEQUENCE: 545

Lys Ser Gly Arg Tyr Asn Leu
1               5

<210> SEQ ID NO 546
<211> LENGTH: 7
<212> TYPE: PRT
<213> ORGANISM: Macaca mulatta

<400> SEQUENCE: 546

Glu Glu Gly Ala Leu Ile Glu
1               5

<210> SEQ ID NO 547
<211> LENGTH: 7
<212> TYPE: PRT
<213> ORGANISM: Macaca mulatta

<400> SEQUENCE: 547

Lys Pro Leu Val Thr His Arg
1               5

<210> SEQ ID NO 548
<211> LENGTH: 7
<212> TYPE: PRT
<213> ORGANISM: Mus musculus

<400> SEQUENCE: 548

Lys Ile Gly Arg Tyr Asn Leu
1               5

<210> SEQ ID NO 549
<211> LENGTH: 7
<212> TYPE: PRT
<213> ORGANISM: Mus musculus

<400> SEQUENCE: 549

Glu Glu Gly Ala Leu Ile Glu
1               5

<210> SEQ ID NO 550
<211> LENGTH: 7
<212> TYPE: PRT
<213> ORGANISM: Mus musculus

<400> SEQUENCE: 550

Lys Pro Leu Val Thr His Arg
1               5

<210> SEQ ID NO 551
<211> LENGTH: 7
<212> TYPE: PRT
<213> ORGANISM: Canis lupus familiaris

<400> SEQUENCE: 551

Lys Ile Gly Arg Tyr Asn Leu
1               5
```

```
<210> SEQ ID NO 552
<211> LENGTH: 7
<212> TYPE: PRT
<213> ORGANISM: Canis lupus familiaris

<400> SEQUENCE: 552

Glu Glu Gly Ala Leu Ile Glu
1               5

<210> SEQ ID NO 553
<211> LENGTH: 7
<212> TYPE: PRT
<213> ORGANISM: Canis lupus familiaris

<400> SEQUENCE: 553

Lys Pro Leu Val Thr His Arg
1               5

<210> SEQ ID NO 554
<211> LENGTH: 7
<212> TYPE: PRT
<213> ORGANISM: Drosophila sp.

<400> SEQUENCE: 554

Lys Gln Gly Arg Tyr Asn Leu
1               5

<210> SEQ ID NO 555
<211> LENGTH: 7
<212> TYPE: PRT
<213> ORGANISM: Drosophila sp.

<400> SEQUENCE: 555

Glu Glu Gly Ala Leu Leu Glu
1               5

<210> SEQ ID NO 556
<211> LENGTH: 7
<212> TYPE: PRT
<213> ORGANISM: Drosophila sp.

<400> SEQUENCE: 556

Lys Arg Leu Val Thr His His
1               5

<210> SEQ ID NO 557
<211> LENGTH: 16843
<212> TYPE: DNA
<213> ORGANISM: Homo sapiens

<400> SEQUENCE: 557
agaaggctcc ttcgcgcagc ggcgcgccaa ccgcaggcgc cctttctgcc gacctcacgg      60
gctatttaaa ggtacgcgcc gcggccaagg ccgcaccgta ctgggcgggg gtctggggag     120
cgcagcagcc atggcaagcc gtctcctgct caacaacggc gccaagatgc ccatcctggg     180
gttgggtacc tggaaggtag gtgctcgtgg gggcgcgggc ccggggctcg cctcacactc     240
tccgcgcggc ctgtattggc gagggacccc gagtgaccct gagcagctcg ccccgcggac     300
gcccggcgtg ctgggagcca ccgcgcgggct tgcagggtcc ccagcgggct ggggtcggcc     360
ttgcagagac cggggccctt ggctccccgg gttggccctg ggcgtcaggg cagcatcctg     420
cgagtggggt ttgggagcag ctcacgggag ccccgccct accgcgggca acccttgatg     480
```

```
ggcggcccac cagtccgcat tttgggtcct agcgggcgcc ccaagcggca caacgcgaga    540
gggaggcggg gaaagtgggc ttcacagacc ggtggacctc gggcgcagac agggacgtgg    600
agccgtcggc aaggtgtggg agcgcagacc cagcctcctt tccctcgagg cacctgtagc    660
ccggttgcct cacttgtaaa tagttggtct caatcgtttc gattcttgcc ctccctgagg    720
aataagcatc tcaagccggt agagggcaga gaattaggtg gcgcgagttt gcccggaccc    780
agctgttaac aaggcgcagt gcggagctcc tcggccaggc gccgcctcgg ggtgccctgg    840
gtctggaact cgggagaaaa atctgggcac cccgtagcta gttgataatt caggaggcgc    900
caaggttagc attttccctg taaaacctca acaccacaca gcgtccccga gaagtgccta    960
gccggatgag aatgacaata ggacatgaaa catcatagga tatgaaaaat gataatatga   1020
tatgaaaaac caaaaataat agcctgagcc tgattatctg aaaattgagc aacaaaggtg   1080
gtggtatggg agctgaggca aaacctagaa ttttttaacct tctaagtatt gcatattata   1140
ttccacagcc ataacctggg tttctcagtt tctgtttttg ttgtttgctt gtttgtttgt   1200
gacagggtct cgttgcccaa gctggggtgc agtggcacaa tcatggttca ttgcagcctg   1260
gaactcctgg gctcaagtga tcctcctgcc tcagcactgc gggtagctgg gactacaggc   1320
gctcaccacc acacctggct aatcttttttt cttccccgca gagacagtct ccgcttgttg   1380
cttagggtga tctccaattc ctgggctcaa agcgctcctc ccacctcgcc tcccaaagct   1440
acaggtgtga accatctggc aggcccacgt cccaggtttt tctcttaaaa tttgaatatg   1500
ggcctgggcg ttggatattt acacacagac aagggaagaa acaacagaa agaactgagt    1560 gaactgtgag atgtttgaaa taggacagaa gagtttacat gtaccctaaa acctgctgtt   1620
gaaaattagt aaatataagg taagaaaaag gtcatttgca tcagggagag tgtttcttgg   1680
ccagaatgat cagggtacgt gatttgtttc ctccaaaaac tccagtggtg tctctaaggt   1740
tgtaattgaa ttacaaccat gacaccaagc taatttccat ctgttgcatg ttatgctctt   1800
ggaatggatg cagaaggatg ctttcttggc aatagcaaat actttctaag catgatgcaa   1860
cgcacagata tatacatgta actggaataa aaattactta acagtactta acctatgtag   1920
gctgcatttc aatattttttt tctattccat ttttccaaaa attattgtca tacctccaga   1980
agctagtttt gtgacccatc atttgaaaat cactactcta gggtaaataa ggagtaaaag   2040 tttattttttt tttttttgag acaggggctc agtgtcaccc aggctggagt gcagtggcat   2100
gatcatgatt cactgtagcc ttaacctctt gggctcaagt ggtcctcata cctcagcctc   2160
ccaagtagct gggaccacag gtgtgtgcca ccacactcgg gtagtttgtt tttaattttt   2220
tgtagagaca ggtttcccta tgttgtccag gctgaggagt aaaagtttat gaaagagggt   2280
ttcagattat tcacttgagc actcaatgcc ccaaaaagct atgtatttgt ttaagataac   2340
atcacatcat aacatctgta catttaggtt atgcattcca gtagacagag ttcattgaga   2400
aattggataa tgtctgcttc attcattact atttctagca cttctcacag tgcctggcaa   2460
atataggagt aggtatccaa aagttatgtg ttgaattcat atgaagaagt aaaacgactt   2520
tagagatagc tgtatggtga aaacgcccac ttgtattcct gtggatgagg agatcaggtt   2580
ggtgtagaat tgtacggtgg gggcagcggg gaatggtggg tcaaagtaat ggtataagga   2640
tggacttgga atcaacttcc tttttttttt taatgactta aaacctttcc ctggggccgg   2700
gcgcggtggc tcacacctgt aaccccagca ctttgggagg cagaggcggg cagatcatga   2760
ggtcagaaga tagagaccgt cctggctaac atggtgaaac cccgtctcta ctaaaaatac   2820
```

-continued

```
aaaaaattag cccggcatcg tggcacgcac ctgtagtccc agctacttgg gaggctgagg      2880
caggaaaatc gcttgaaccc cagatgtgga ggttgcagtg agccgaggtc ccgccactgc      2940
actccagcct gggcgatgga gcaagactcc atctaaaaaa acaaccaaac aaaaaaacct      3000
ttcccttgta tgtgtgtatg tattctttca cagatgctcg acagaagatg tgatcctttg      3060
cctgtctttg tgacagctgg aggaggccct gcaggcaggt gcagttcctt attctcctgg      3120
gtcttcccat gccgtagcgg ctgtgttgta cctttcagac cctcagcagg gctctggtag      3180
tctctactct tgaaggtcct caaactccat tctcttctca ggtgagggtt tcaggcagat      3240
ggggagacca tctctgcccc agacccatgt ggccttggaca gggtttcttt ctggcagtct     3300
tgccttctac attggatagt aaacaattac acctgtaatc ccagcacttt ggaaggccaa      3360
ggcgggtgga tcacctgagg tcaggagttc gagaccagct ggccaacatg gtgaaacccc      3420
ctctctacta aaaatacaaa aattagcccg gcatggtggt gggtgcctgt aatcccagct      3480
gcttgggagg ctgaggcagg agaatcactt gaatccagaa ggtagaggtt gccatgatct      3540
gagattgtgc cactgcactc cagcctaggc gacaagagca aaaaaaaact cggtctcaga      3600
aacaacaaca acaacaaaaa cccatcacac cattgtaaag ccaggaagct tttaaaacag      3660
agatgatgtc tggtgcccac cagtgtcttg ttactgatag tgttttaat ctagttgaaa       3720 aattgttgga ggtaaaagtc attgtaagtc tcctatgtat gctcacagaa tactcctagg      3780
gctgaaggta caactatgtt tctccatctt ttgccatgat cactacctcc ctcccaccta     3840
ggagccttgt gagactttt tttcccctaa tttgccccaa ataaaattg taatatcaga        3900 gataatattg tacttctgct tatggccagt agccttctag agggtcacaa gctgttctat      3960
aagctgaggg gggttttttt gccccagaga actaattttt gtctctttgg ggacaatagc      4020
acccacttta agaatgcatg aggtaaaaga aaatgtgcca ggaaagactt gctccacctt     4080
ccccaagtgg ggtaagcttg tgatggccca agatccttgg atgggtgag ggttgaggcg        4140 ctgtgggcat ggaggtaaca caggagccag atttactgtt cacttccctg gtgtctctaa      4200 agccccatc tcttcctctt caagaccaaa gacatttaaa taagccctgc ccctacaggg        4260
tcagtcctgg tccatgcaca tctcaactag ttggaaacag cagtgtctta gaatttggga     4320
caaattgatt aaaacagaac aggaggaagt taatttctgc tgccaaacct gattctgagt      4380 gatcgttttcc tgttccttgc tccaggatta tcagcacagc attctcatgc ttcctactca   4440
ggaccgtttc tttacccaaa gtgaagtttc ctttgccccc tccccttatc ctttgatttc     4500
agtagtaaca cctgctaact agagaacatt tcaaaaatga agagttccct gttcccagag      4560
atccccgtgg ttaatattgc aaaatatcca atctctgaga tactttggtt ttaccataaa     4620
cactgtcctg tgaccgtctt cctgtttagc actgtggctt gcttttgac ttgcagaggg      4680 aagagaggga ggggtatctt gaagtaacta gcaagacctg taagcaaaag ggaagaagac     4740
taggttttaa aaggagtgtt gtatctgtgt aggagggaga cactgatttt agttatcagt    4800
gtctcagagt tggtattagc cagccggtgt tatcaaagga ggaactagga ccgctgtctt    4860
gaaggaggtg gtggaggact caagggcaga ggcttctcac tgccatcact tggtgccatc    4920
agcccagagc atttcaagtc actgcccaac gtagagcttt gcagagccag aagttctggg    4980
aggaatgggc atgcatggtt ttgcccatca agggcacaca gattagtggc aggatcgggt    5040
tagaaacatg taggatttgt atgattgagc tgtaattgga gtgtttcata tactgcattt    5100
ctacagctct catcagtaat ggctgtgcct ggatgccacc cagcatgttt tcatagttta    5160
ccttcttttt agaagtcaat ctggaccct ccttctgttt gcattttctc tttgttgaca     5220
```

```
tggaatgggg agatgttgtc atcctgtgtt ggcattccca agtttagtga atggtttctc    5280
accatagctt aagttggctg cttcatttt  cataaggcaa attagtttct ctcagggaag    5340
ggctgtacat tgagatcatt aacatagaat gtggttgtgg atcctcgtac attttcattg    5400
cagaggtgac ttttccctc  cagcacctt  gatcagcctc ccagcacaca tgtctccagc    5460
gaatggcaca tatccaagga atgatcagca gcttcttcgt gacctcttgc agtcattgct    5520
gtcttttact tttctagaaa aacctctcac aacttttttt tcatgtcgtg ccaacgcaag    5580
cttgattatc ctagtctgtg ctcttttggt tccaaagaac tgaaaaacca ctttaatctt    5640
aagcaggaaa aaaaaaagtg tgtttggggt ggggattgat tgacttcccc aaacaacagc    5700
cgctgacatt aggtgtttga gattcagggt tgtaaatgtt gtcaccagga tttggcctcc    5760
ctccactttc ctgcagcagc tccaggctga cattctccca gctcagtgac ccagcagaa    5820 ccggggctgg actcaggggt tccaattcaa gtgcaaagat tgagtcttat ggcctggatt    5880
gagtcatgtt cctgtccccg caccagttgc atggcaggca gtgcgtggct aggctgagcc    5940
tgcggagtgt gccctcagca gctcctcaga gaaaaatcaa tcaaggcgcc atcaagcctg    6000
gagaaagttc agtgtgtcct gggcagtttc ctgcctgggc cccagttgtt ctttctgggg    6060
tagggatgtc ctctgctctc cctgctgtca tcagtggtgg ttgtgcccgg acaccactca    6120
gggcctgtgg taaggcattc tttctggaaa ttgagattct ctgttccttc aaccgtgcag    6180
agtggggaag gctgcaagag cagcttctga ggtcctccag tcaaataaga ggtcgccagg    6240
tcctctgagg gtcgtcccct cttaacccac accttcgatg agcatcccca ccctgcctcg    6300
ctgctccctc tgaggtggag agtgagctcc atgctaacag gctctggtaa cgggcttgtt    6360
caactgggcc cctttcttcc ccaaagcctg ttgaaaatag ctgatgtcaa aacacagatg    6420
tctgcagctg ctatggccct gggggtttt  tcttttcatt tgtttctacc ccagctctcc    6480
aaaggaatgt gctctgttca ttcaacagcc cgctgcacat gtttattgct cagctctgtg    6540
atcatagcag gatagtgaaa gttggggat  acgtgtccat gcagcctacc tgggtgccag    6600
tgaagcgcga tgccatgtag gcacttcctc ctcctcttca gtagccaggc tcccacagc    6660 tgttctggtt actcagatgg tcaggtggct tggccatgga cacccattca gtcatttgc     6720 caggtcagcc actaaccatt tggtgatctt ccatgatcca cattcccct  cgtttccctt    6780 taacttattt ctctctgctg atacctctga ggggccatct cccgtgtctc caccccttga    6840
agcagatcct catacagtga gaattgacac atgggccttt gaataaacat cagtgatgtg    6900
cttaacttca tgataatctc ccagaaccgc ttgaaaacaa gcgactgccg gtatcagaag    6960
ccatgcatga aaagagagcg taagggcag  gcattcactg gctgaactgg ggagccacat    7020
gggaattggg gtccatagga catctatttt tgaaatattt tgagatattt gaaggaaatg    7080
gtttccctta ctatctcagc attcagagtg tggggaaatg tttttaatac agtggtttgc    7140
aaatcagtgg atgtgaagaa gcaagaaaat gagatggctt cagcatatct tttaaaagtg    7200
atctcaccta cacttaagtg gctgtcagat tctcctacag ggcaatgctg tgtggccttt    7260
cacttccatc ccccgcgtct gaggctgata gtccagaatg ctgctgagga agtgcacgtg    7320
gtctgtcttt gctgaacaaa gtggcaggct ggtcagcagg tatcggtggc tgccactgcc    7380
cctcctcctt gctgtgcaga ctctgcattc tgcgggctc  acgttctttc tcctttcagt    7440
cccctccagg gcaggtgact gaggccgtga aggtggccat tgacgtcggg taccgccaca    7500
tcgactgtgc ccatgtgtac cagaatgaga atgaggtggg ggtggccatt caggagaagc    7560
```

```
tcagggagca ggtggtgaag cgtgaggagc tcttcatcgt cagcaaggta tcgttccgcg   7620
gtggggctgg aagggctct cggtcccatc atctgttggt gcatcagccc aaagccaagt   7680
ccacactcaa tacagctaca cttttcactg atgggcgatt cttcccgggg aaacgtatca   7740
cccacggcca tacagggctc cagagctcgc ccatccttgg ctctctgttg aatggtcatt   7800
ccatctgggc ccattgctta gagtcccgtg ctgatgaggc tgaggttgtg gattggccct   7860 cccttttccag ggagtcgctt tcaaggatgg aacttggttc ccatctgcaa actgaatctc   7920
cagtgctagc cactgtcttt gacctgagat actgatgcac aaaggacatg aggcaggagg   7980
atggggctgg ctccacaaac caagcccgg ggggaaagtt tcgagagttc ttgcttaggc   8040
ctagggcagg ctagccaatc tgtccattcc attttgtgtc ctctggtcct tgtaagaggt   8100
ctctgtgacc tggtcatcct gcctgccttt ggaaagttag gatccagtac gcagtggaaa   8160
tgccctcaca accattcaca gcatcatggt aaagcaaatg ggttttgggg agaggagact   8220
gctctgtctt tccagccagg aagctgcctt gtggctggca atgatgacat gtgccctctc   8280
gctggcttag ctgtggtgca cgtaccatga aagggcctg gtgaaaggag cctgccagaa   8340
gacactcagc gacctgaagc tggactacct ggacctctac cttattcact ggccgactgg   8400 cttttaaggta tgggatgcct ggtgcagacc aggtcccttg gggctcaggt gcaacctgtg   8460
gtgtgttttg agctccctta gcagattacg tgtgggtgac tttctgttct tgctgctcaa   8520
ggtatagcca gtgaccatc agcactggca tcacctggga gcgtcttaga aatcacagtc   8580
tcgggcccca cgcaggccat ttgaatccgc accagcagtg actcatacgc acacttcttc   8640
aaagtttgag gagcactgct ctttgccagt tggtagatgt gcaatttaaa actgtcagca   8700
aacacagctg ctgtctgtag tgcacacagc catgaggcac ggtcagccct ggccctcccc   8760
tccaggcacg tgcacacacc aaccccata cacatgagtc cctacccacg ttctacatgc   8820
ataccctgtc ctgtggaggc ccggtaacta tttgcagtct agttgttggc acaagaagaa   8880
cttgagagtt actttgtctt ttgccttttt tctagccact gcctcagttt tctgctgtga   8940
gccaggttca agtgtgggt ttagctttat cccgtagccc tgttttattg caccacagca   9000
tatcagggct gaagggactt gacttttatc ttttgatttt aggggtaagc tggggaggct   9060
gggccaggtg gtagttttat aggccagtga cccgccaggc cttgggccct gtgagtcctg   9120
gtcttgagtc cttcctgtat ccacacattg cagtcagtgg cggggctagt ctctgtgacc   9180
aagtagtgtc catgtctccg tctgacagtc tcagctccag cccgtttgat aaagaagtgt   9240
tggctatctg cctatttcct tttcatagtg gcacacagat tatccctagc cagctgtggt   9300
ggtttagaat tgttttagat gccagcttcc cccagcaggt ctgtgaagga ctattactga   9360 ttgtttttgtt tgtttgtttt ttattgtaat gacagcctgg gaaggaattt ttcccattgg   9420
atgagtcggg caatgtggtt cccagtgaca ccaacattct ggacacgtgg gcggtaagac   9480 agccctggt tggaccttgt tttcgtgact ggttccctct tcttcttaga agcaatctgc   9540
ctgccatttc tcacattgca ttttgttatt ctgtccctgt tgtttgctct ctcttttttt   9600
ttttttgagt tggggtctcc ctctgttgcc caggctggag tgcagtggca caatctcggc   9660
tcactgcaag ctccacctcc tgggttcacg ccattctcct gcctcagcct cctgagtagc   9720
tgggactaca ggtgcccgcc accacgcccg gctaatttt ttgtattttt agtagagacg   9780
gggtttcacc gtgttagcca ggatggtctt gatctcctga cctcgtgatc cgcccgcctc   9840
agcctcccaa agtgctggga ttacaggcgt gagccaccgc gcccggcctg tttgctcttc   9900
ttatctcatt aaagccagcc tggctttcgt ctcactgtct cttagcttct gaaaggtcta   9960
```

```
attcactggc actgaagagt gagggcagga cccgttaaac tggtgcaaac gacacttctg  10020
atcctgtcct ttctgggttc gtttctgcac cacacagaca cttttctctg taggccatgg  10080
aagagctggt ggatgaaggg ctggtgaaag ctattggcat ctccaacttc aaccatctcc  10140
aggtggagat gatcttaaac aaacctggct tgaagtataa gcctgcagtt aaccaggtaa  10200
acatccccca acgacactgg cattgcaacg ttgctgtttt actgtctgat gctggtaggg  10260
atttctcgtc cacctcaccc agcaagtggc caggaggcag ctcctgggtg ttggcagagt  10320
cctgagttat gattcagcat gacacagcac atctgggaga ggaaacttac aggaagaaa   10380 gagtttgagc ctggcttgtg acgatttggg gtctgacaaa gaggcagcca tgagatcctc  10440
agaactgtga tagttgataa gtggctaaag ccaagaaaag cctctagggc ccatgagaac  10500
atctataata agataataat aacaccaagg atactacctg gaactgtag gaagttacag   10560 cttatctggg aaataggtg tttgttatac atagttttct gtatggggta gggagggact   10620
ttagcatagg aagcttcatc tgtgtcccat cagcgtgtag ccacagtgct cccatcagct   10680 cttgttttg catttgcaga ttgagtgcca cccatatctc actcaggaga agttaatcca   10740
gtactgccag tccaaaggca tcgtggtgac cgcctacagc cccctcggct ctcctgacag   10800
gccctggtga gcttcccaca ggctcatgct cctgtgtcac ttggtgaaga ttagaaaaga   10860 ctaaaagaa caattcagcc tcaaggaaga tgtttctggg ggtgatctgc aaaacttccc    10920
ctgagcctct tgctggtttt cctggaaggg ttggagtttc tagtagcaag acacctactc   10980
tttttccaaa gggttggggg ttcttaaccc agctctgagg aggagactgg tggctgccct   11040
ctgaggtcga tgggaggatt agggttgggg tttctggctg ctgtgagtgg tggccatgat   11100
ggtgtgacct ggactgtctt tctatcctca gggccaagcc cgaggaccct tctctcctgg   11160
aggatcccag gatcaaggcg atcgcagcca agcacaataa aactacagcc caggtacagc   11220
cacttcaggt gttgctgacc gtccacaact gcctgcattc ctgacagtcc tgttagccaa   11280
gaggaggaag tgactgagcc tgttacaccc tcacaggaag tatggttagg ggtcctcaag   11340
tacagagtgg aaagggcaca gatcggggtt ttagaagact ctggcatggg ctcttagatt   11400
aatagtgcct gcccccacta ctgcaagggt gactgccacg agggccagcg cttgttcatt   11460
catgtggaac ctcatctgta caaatgtaag agctcttagc cgtgcaggga atgttctttc    11520
tcctgagtgg tagtgtgcat ttctagccag tggagggcct catgtggtct catgatatgc   11580
ctgagacact gaagcgtgtg gcacagtggc tagcgcagga ctctggagtc agatctggac   11640
ctgaatgcgt cgcctacctg ttgctagctg tgacctgaca tcttggagcc cctctctgat   11700
cacctgtgga gttctagcac gtccttctgc aggttgtgtg tgtgagagac tgagatgatg   11760
ggtgcgagtg cctggcatgt atacacactc actgtctcct tgggctcaca ggtcctgatc   11820
cggttcccca tgcagaggaa cttggtggtg atccccaagt ctgtgacacc agaacgcatt   11880
gctgagaact ttaaggtaag atcttggctg gtcaggcctg gccctcctcc atggagtggg   11940
ggatggggga ggcctctcat cctgtctctg gagtgtcatc tgtgggatca ccaccatcct   12000
ctcttctgag gccagggagc tgtggcgagc aagccaagac tgagactgac acctcaccag   12060
tggagccgtg tgcaggggca ggccttggc ctccagggcc ccgtgctgtg cacgcataca    12120
cctacacctt tgctcaggcc cttcagccac accgagaggt tacccgggga gaatctcgct   12180
cttgagcttc actgcctgga cctgccctgc actggagctc tgtcagctac cagctgcata   12240
accctgggca agtcgcttaa ctgctcgatg cctcagcttc cctatctata aataatatc    12300
```

```
cattttgagg gttgttacga agattaagtg atgcatcaga gcacttcaca tggtgcttaa    12360
taccttagta agtgatcgag aaatgttgct gtgctgataa gtccagggac tgcaaaggac    12420
cctctgggcc atttagtcca ttcaccagct ctgcaaggag ttcgtgtgat gatgggcaga    12480
gcctagacct gtgtcaggac tctggcgaag cgctcagtgt ggcagctgga gcagctcagg    12540
ctacttggcg ccacctccct ccctgcctgc ccttgcagca ttggtggcgg gggtgtgggg    12600
gagggggggg gcacgcccaa aggagagcag ctcaggggag tcctgatggc caagagcct     12660
ctgttctcac tgagcaaagt ggctctgcca gggatgctct gtctttatcc aagatctgtg    12720
ccgagcgcag cacagccatg ggcctgggc tcttgggcag gccccagctt aggtgagcag     12780
ctgattttgc ccaattccac tgcccaaaga ctgtggccat agtgcctgcc acctgtcaca    12840
tatgagacag ggatgagagt gatccctgaa gagggaagtg gagctcattg tttaggagag    12900
gagacgtttt tcttcttacg tgcaggtaga tgttctaagt acacaagata aaatggcaaa    12960
acagtggcca ctgagggaaa ggcatatccc accagagatg catcgtttgt ttcgtatttc    13020
atttttaag gaattaggaa agaaaaaata aatgactaat ctcaaaatgc taacctaatt     13080
atttatttt tgcatcttac tgtatagctt ttgcacattt ttctgtgatc ataaccacag     13140
agcctgtagc agactctctt tctgcacatt ctgtgatcat ctgaagctaa gagcccttcg    13200
gctctgggag tgtgtgtcag cctcttgtgg gtctcaccca gtggtgcctg cctgcctccc    13260
tccctcccag cctccatgcc agctgagttc tgtaccgtct gctgccttca tgcaggtggt    13320
tctcttctcc cagtatacct ttcttgccct ctctgtcaaa atcttatact cttaggcca    13380
tgtcaaatac catctcctct tcggctgtgg ttgttcagtt tcccggctgg aatccctttg    13440
gaatacctct gcccttcctg tgctgttgag tgtcttatac agtgtgtgat tagttatttg    13500
tattacagtt gtagaaatac ctctgccctt tgtttgcttc ataaaataga ggcaaagaca    13560
catcttaccc ataattatat tcctcactgc aacttatcac aatagaagtg ctcagtagtg    13620
ttttttgaaa tgaaataaaa tgtatcattt ccctgggagg ttctggaaag gaaggactgt    13680
ttccatcgtt ccatatatta tctagcccaa catgcacatt tcctgaatac taatatatca    13740
gcttttccta agttcagttt atcttatcgc tcctctctgc tcaaagccat ggaagacatc    13800
tgggtcctgc acagtatttt gtcttttatt tttatttgca gagcttactg gattttttg    13860
tttgtttttt aggtctttga cttttgaactg agcagccagg atatgaccac cttactcagc    13920
tacaacagga actggagggt ctgtgccttg ttgaggtgag tgagccccag tgtgaggagc    13980
agttcccagg agatattcag atgctgcaca gcaagagagt gatccctgca ggcctcagcg    14040
ccaatgtgct ctcgtcacag ctgttcttgc tttgcacatt accttgcttt tcagccacg     14100
tgacttgcat cagctgaact gcatggagcc aagatgccaa gagatccgct cttgatatct    14160
tcttccagcc ctggggcatt gttggcctgg cctgaagtaa ctacatattt tggctttcca    14220
ttcaatttt aaatcctagc agttcatctg aaactaggtg atcccaggtg accctggatc     14280
aaactctgga agaatttgcc tgtgactttt tgtcttaatg accctaatga aaggggtttg    14340
gtcgggagcc cctggggctg aggtttgaga cagtcccggc tctgacctgg taagccacat    14400
ggctccaaaa caggccctcc ctctgagcag caggcacctc agttcctcca gccacacatc    14460
ctctggttct gtttcctctg catggtagtt tggaaggagc tgcctaggaa ggttttctgt    14520
ggggttttct cttttcctac cattacaata actaggtgac gcatgtaact cactttctgc    14580
tttcaagaag gaacttctca ttttgcagtg gagactgaga ctctgtttct ctctcactac    14640
ccttattctt gtctgagctc tgtgtttcca cactctctcc tttagtactt cctcttctaa    14700
```

```
gcaaaatgtg aacattccct aagatggggt gggctaccag ctttcccttt ccagcgtctg   14760
tcccatctcc ctccccggag tttgcactgc tggtggcttc agccaccgcc ccaggcagat   14820
gtttgcccag tctgcgtcct ggacaataac tctggccctg cttcaggcat atgcgtgcct   14880
ggcaagcctg ctgctgccac actgtggcct cacactcaaa ataggccgca aacagagcat   14940
gtcacaggca gccccaggcc agtgcccttt cagacatctc tgttaatgct acttagccct   15000
agacattaaa atcatttttg gatctagtgg acaaggagga gaggagtgaa tcagtcacca   15060
agctacattc gttctccttt cagaatctct cccattcatc cgtcttcctt ttcccctccc   15120
acttgagaca gagtggattg aagctttcag ggctgaggaa acacagtggt tttctcattg   15180 ctcccttta c agttaggctc ctctgccctc cagtattgtg ctagaaactt ctgttcgatt   15240
atcctgttgc gtggcggtga gtgggaggaa gaggctagcc ctgacatgct caggtctcct   15300
agggagtttt cgctaactac acacacacca ccctctggc agataatgct ttactgagcc   15360
tgacctgctg atgtcagtgt cactgtgggt atacaaaaaa ggcagaccat ggagaacttt   15420
tgaataagag ttacagactg taagcaccca gctcagatta cataactctg gccttgcgtg   15480
agctgcccag ctatctgtcc agtgttcctg cctttatgtt cctagcacag ccattggccc   15540
tactagatgg acagtgagtg agccttgaca aacacgtctg cacctgtgct ccctgccatg   15600
tgctccctgc cctgtgctcc ctgccctgtt tccaatataa aatcgccgac cgttgattgg   15660
gctcacttca gccccactg atacaaggag gctccctctg tcctcagagc acttgccgtt   15720
gcttctctta tcctttgaga ttcagtcaca tacagacttt taacatccct tttttttttt   15780
gaaatgggct cctactctgt cacccaggct ggaatgtaat ggcatgatca cagctcactg   15840
cagccttgac ctcctgggct caaatgatcc tcccacctca gcctcccaag tagctggggc   15900
catgggcatg caccaccatg cctggttaat ttaaaaagtt tttttattaa gatggaaatc   15960
ttgctatgtt gcccaggcta gtcgcaaacc cctagcctca agtgatcctc tcgcttcagc   16020
ctgggattac aggcgtgagc cactgtgtct ggcctgcctt tcatattat tacacaagat   16080 gtttaagacc acaaaatact gtctggtcct gccagctaga ctgagttact ggaaggcaga   16140
aatcgtgttg ccgtcctgca cggcccaggc acagtgctgg gcacatgggg agggtggtgt   16200
ccctcacaca tgtgctgctt gatgacagta gtggtagagg ggtctggagg gtgagttgct   16260
tcccccagct gcagaaccat catctgcaca ctcagaacta gcttgttgcc tctgaggttc   16320
tattttattt cttcagtgag acacatcatt tctctgttgg gagttgggta tagtcaaaat   16380
cacctcttca aaaagcaact gttttctcct ttctcctgac agctgtacct cccacaagga   16440 ttacccctc catgaagagt tttgaagctg tggttgcctg ctcgtcccca agtgacctat   16500
acctgtgttt cttgcctcat tttttccctt gcaaatgtag tatggcctgt gtcactcagc   16560
agtgggacag caacctgtag agtggccagc gagggcgtgt ctagcttgat gttggatctc   16620
aagagccctg tcagtagagt agaagtctct tccagtttgc tttgcccttc tttctaccct   16680 gctgggaaa gtacaacctg aatacccttt tctgaccaaa gagaagcaaa atctaccagg   16740
tcaaaatagt gccactaacg gttgagtttt gactgcttgg aactggaatc ctttcagcaa   16800
gacttctctt tgcctcaaat aaaaagtgct tttgtgagct tgg                      16843
```

TREATMENT AND DETECTION OF INHERITED NEUROPATHIES AND ASSOCIATED DISORDERS

CROSS REFERENCE TO RELATED APPLICATIONS AND INCORPORATION BY REFERENCE OF MATERIAL SUBMITTED ELECTRONICALLY

This application is a Continuation of U.S. patent application Ser. No. 17/517,227, filed Nov. 2, 2021, which is a Continuation of International Patent Application No. PCT/US2020/031708, filed May 6, 2020, which claims the benefit of U.S. Provisional Patent Application No. 62/844,370, filed May 7, 2019, and U.S. Provisional Patent Application No. 62/987,151, filed Mar. 9, 2020, each of the foregoing are incorporated herein by reference in their entireties.

GRANT FUNDING DISCLOSURE

This invention was made with government support under grant numbers NS065712, NS075764 and GM119018 awarded by the National Institutes of Health (NIH). The government has certain rights in the invention.

SEQUENCE LISTING

Incorporated by reference in its entirety is a computer-readable nucleotide/amino acid sequence listing submitted concurrently herewith and identified as follows: Filename: 761350_000281_SL.txt; Size: 147,687 bytes; Created: Dec. 15, 2021.

FIELD OF THE INVENTION

The present disclosure relates to methods of detecting and treating inherited neuropathy.

BACKGROUND

Peripheral neuropathies are amongst the most frequent neurodegenerative diseases, with diabetic neuropathy and hereditary origins amongst the most common mechanisms of action. For the inherited neuropathies, also known as Charcot-Marie-Tooth disease (CMT), the remaining diagnostic gap of patients is ~50%. In our understanding, CMT represents an umbrella concept for clinically and genetically heterogeneous inherited monogenic highly phenotypically penetrant conditions affecting the peripheral nerves. CMT is classified depending on conduction velocity as demyelinating (CMT1) and axonal (CMT2) types. Distal hereditary motor neuropathy (dHMN) represents a form of CMT2 in which the burden of disease falls predominantly or exclusively on motor nerves (Rossor, Tomaselli, and Reilly 2016). A similar condition includes ALS4 (juvenile dHMN+brisk reflexes as sign of upper motoneuron involvement). As opposed to CMT1, for which over 90% of cases have mutations in known genes, only 20 to 30% of CMT2 and distal HMN patients receive a genetic diagnosis (Fridman et al. 2015).

SUMMARY

The disclosure provides a method of treating and/or detecting inherited neuropathy. In various aspects, the method comprises detecting the presence of a mutation in the sorbitol dehydrogenase (SORD) gene in a sample from a subject. In various embodiments, the SORD mutation is a DNA variant classified as pathogenic or likely pathogenic according to American College of Medical Genetics and Genomics (ACMG) criteria. Optionally, the method comprises diagnosing the subject with inherited neuropathy when the presence of a mutation in the SORD gene is detected. Optionally, the method comprises administering to the subject a composition that comprises an agent selected from the group consisting of an aldose reductase inhibitor; an aldose reductase antisense oligonucleotide; a polynucleotide that encodes a SORD peptide; a SORD peptide; an agent that blocks expression of a mutant SORD gene; and an agent that corrects the mutation in SORD gene. In various aspects, the method comprises administering to the subject Alrestatin, Epalrestat, Diepalrestat, Fidarestat, Imirestat, Lidorestat, Minalrestat, Ponalrestat, Ranirestat, Salfredin $B_{11}$, Sorbinil, Tolrestat, Zenarestat, or Zopolrestat (or a combination thereof). In various aspects, the method comprises administering to the subject an aldose reductase antisense oligonucleotide; a polynucleotide that encodes a SORD peptide; an agent that blocks expression of a mutant SORD gene; an agent that corrects the mutation in SORD gene; or a combination of any of the foregoing. In various aspects, the method comprises administering to the subject a SORD peptide. Administration of a combination of any of the foregoing is also contemplated. Optionally, the method comprises measuring sorbitol levels in a sample from the subject.

Also provided is use of an (i) aldose reductase inhibitor (e.g., Alrestatin, Epalrestat, Diepalrestat, Fidarestat, Imirestat, Lidorestat, Minalrestat, Ponalrestat, Ranirestat, Salfredin $B_{11}$, Sorbinil, Tolrestat, Zenarestat, and/or Zopolrestat); (ii) an aldose reductase antisense oligonucleotide, a polynucleotide that encodes a SORD peptide, an agent that blocks expression of a mutant SORD gene, and/or an agent that corrects the mutation in a SORD gene; and/or (iii) a SORD peptide for the treatment of inherited neuropathy (or use in the preparation of a medicament for treatment of inherited neuropathy) in a subject which has been tested for the presence of a mutation in the sorbitol dehydrogenase (SORD) gene.

The disclosure further provides a method of characterizing a neuropathy in a mammalian subject, the method comprising measuring the level of sorbitol in a subject suffering from a neuropathy, wherein a sorbitol level of greater than about 10 g/L indicates that the neuropathy is associated with a mutation in the sorbitol dehydrogenase (SORD) gene. The disclosure also provides a method of evaluating the efficacy of a treatment for an inherited neuropathy in a subject, the method comprising administering to the subject an agent selected from the group consisting of an aldose reductase inhibitor (e.g., Alrestatin, Epalrestat, Diepalrestat, Fidarestat, Imirestat, Lidorestat, Minalrestat, Ponalrestat, Ranirestat, Salfredin $B_{11}$, Sorbinil, Tolrestat, Zenarestat, and/or Zopolrestat), an aldose reductase antisense oligonucleotide, a polynucleotide that encodes a SORD peptide, a SORD peptide, an agent that blocks expression of a mutant SORD gene, and an agent that corrects the mutation in SORD gene (or a combination of any of the foregoing); and measuring the level of sorbitol in a subject.

It is understood that each feature or embodiment, or combination, described herein is a non-limiting, illustrative example of any of the aspects of the disclosure and, as such, is meant to be combinable with any other feature or embodiment, or combination, described herein. For example, where features are described with language such as "one embodiment," "some embodiments," "various embodiments," "related embodiments," each of these types of embodiments is a non-limiting example of a feature that is intended to be combined with any other feature, or combination of features, described herein without having to list every possible combination. Such features or combinations of features apply to any of the aspects of the invention.

The headings herein are for the convenience of the reader and not intended to be limiting. Additional aspects, embodiments, and variations of the invention will be apparent from the Detailed Description and/or drawings and/or claims.

BRIEF DESCRIPTION OF THE DRAWINGS

(FIG. 1A) Representative pedigrees of dHMN/CMT2 families carrying biallelic mutations in SORD. The squares indicate males and the circles females. The diagonal lines are used for deceased individuals. Patients are indicated with filled shapes. (FIG. 1B) Schematic diagram showing all exons, introns and untranslated regions (UTRs) of SORD on the basis of NCBI Reference Sequence: NM_003104.6. The gray and white boxes represent the coding sequence and UTRs of SORD, respectively. Variants identified in the families considered in the present study map throughout the coding region of the gene. The nonsense c.757delG; p.(Ala253GlnfsTer27) variant on exon 7, was identified at particular high frequency. (FIG. 1C) Distribution of mutation across SORD protein domains. (FIG. 1D) SORD protein orthologs alignments showing that the four missense substitutions identified in dHMN/CMT2 families in this study are located at highly conserved residues across species from humans to elephants (FIGS. 1E and 1F) Magnification the nucleotide sequence of a highly homologous region in exon 7 in SORD (reverse strand) and SORD2P (forward strand). Nucleotides differing in SORD2P from SORD are indicated with an arrow, including a FIG. 1C deletion in SORD2P. Representative electropherograms shows that in SORD the c.757delG; p.(Ala253GlnfsTer27) variant found in homozygous state in dHMN/CMT2 patients and heterozygous state in available patents (right box, upper plot) is absent in biallelic state from healthy controls (right box, lower plot), but it is fixated in SORP2P (left box, lower plot).

FIGS. 2A-C. Decreased SORD expression and sorbitol accumulation in patients fibroblasts. (FIG. 2A) Schematic representation of the two-step polyol pathway converting glucose to fructose. (FIG. 2B) Immunoblot showing protein level of SORD using the polyclonal antibody ab189248 and normalized to Tubulin in healthy control (n=4, lane 1-4), heterozygous carriers of c.757delG; p.(Ala253GlnfsTer27) variant in SORD (n=2, lane 10-11) and patients carrying homozygous c.757delG; p.(Ala253GlnfsTer27) change (n=4, lane 5-8) or compound heterozygous c.757delG; p.(Ala253GlnfsTer27) variant together with a second nonsense c.895C>T; p.(Arg299Ter) mutation (n=1, lane 9). (FIG. 2C) Levels of intracellular sorbitol as measured by UPLC and normalised to protein content in healthy controls (n=5) and patients carrying biallelic nonsense mutations in SORD (n=5). The graphs show the mean±s.d. and data distribution (dots). A two-tailed t-test was performed to compare SORD encoded protein (FIG. 2B) or sorbitol level (FIG. 2C) across groups. Statistical significance is indicated as *,  or * if P-value <0.05, <0.01 or <0.001, respectively. All experiments were repeated independently twice with similar results.

FIGS. 3A-F. Loss of *Drosophila* Sord2 causes age-dependent synaptic degeneration. (FIG. 3A) 3D structure of *Drosophila* visual system showing the lamina, medulla, and lobula. The xy- and xz-planes showing the photoreceptor terminals and lamina neurons are indicated. (FIG. 3B) Lamina of yw control fly at 2 DAE. The organized lamina cartridges and columnar photoreceptor neurons are shown in the xy-plane and xz-plane, respectively. (FIG. 3C) Laminae of Sodh2$^{MB01265/MB01265}$ homozygous flies at 2 DAE and 10 DAE. Arrowheads indicate the lamina vacuoles. Boxes indicate higher magnification areas of the lamina. The intensity of BRP is indicated. Dotted lines indicate the area of lamina vacuoles. Scale bar: 30 µm. (FIG. 3D) Quantification of the vacuole number, size, and BRP intensity. A total of 3 laminae of each group were quantified. Data are presented as mean±s.d. Statistical analysis was performed using Two-Way ANOVA followed by post-hoc Tukey's multiple comparison test. *P<0.05, P<0.01, P<0.0001. (FIGS. 3E-3F) Locomotor activity of control flies (yw) and Sodh2$^{MB01265/MB01265}$ (FIG. 3E) or Sodh1 and Sodh2 pan-neuronal double knockdown (RNAi) (FIG. 3F) flies. n=10 in each group. Data are presented as mean±s.d. Statistical analysis was performed using Two-Way ANOVA followed by post-hoc Tukey's multiple comparison test. **P<0.0001

(FIG. 4A) Intracellular sorbitol level as measured by UPLC and normalised to protein content in fibroblasts from healthy controls (n=5, circle dots) and patients carrying biallelic nonsense mutations in SORD (n=5, square dots) after three days of treatment with Epalrestat 100 µM, Ranirestat 10 µM or DMSO. (FIG. 4B) Sorbitol level as measured by UPLC from brain/head homogenates and normalised to protein concentration from wild-type (yw, empty circle dots), Sodh2$^{MB01265/MB01265}$ (full circle dots) and neuron-specific knock-down of Sodh1 and Sodh1 by RNAi (square dots) *Drosophilae* at 10 days after eggs enclosure. Sodh2 Mimic and Sodh1 and Soh2 RNAi *Drosophilae* were fed with either 80 µM Epalrestat, 80 µM Ranirestat or DMSO. The graphs show the mean±s.d. A two-tailed t-test was performed to compare sorbitol level. Statistical significance is indicated as *,  or * if P-value <0.05, <0.01 or <0.001, respectively, unless otherwise specified. All experiments were repeated independently twice with similar results. (FIG. 4C) Locomotor activity of control flies (yw) feeding with DMSO, Sodh2$^{MB01265/MB01265}$ flies feeding with DMSO, 80 µM Epalrestat, or 80 µM Ranirestat (n=10 in each group). Data are presented as mean±s.d. Statistical analysis was performed using Two-Way ANOVA followed by post-hoc Tukey's multiple comparison test. *P<0.05, ***P<0.001 (FIGS. 4D-4F) Laminae of Sodh2$^{MB01265/MB01265}$ homozygous flies at 10 DAE and 40 DAE fed with DMSO (FIG. 4D), 80 µM Epalrestat (FIG. 4E), or 80 µM Ranirestat (FIG. 4F). Arrowheads indicate the lamina vacuoles. Boxes indicate higher magnification areas of the lamina. The intensity of BRP is indicated. Dotted lines indicate the area of lamina vacuoles. Scale bar: 30 µm. (FIG. 4G) Quantification of the vacuole number, size, and BRP intensity of (FIGS. 4D-4F). n=3. Data are presented as mean±s.d. Statistical analysis was performed using Two-Way ANOVA followed by post-hoc Tukey's multiple comparison test. *P<0.05, P<0.01, **P<0.0001.

FIGS. 6A-B. Double knockdown of *Drosophila* Sodh1 and Sodh2 lead to age-dependent synaptic degeneration. (FIG. 6A) Laminae of Sodh1 and Sodh2 double knockdown homozygous flies at 2 DAE and 10 DAE. Arrowheads indicate the lamina vacuoles. Boxes indicate higher magnification areas of the lamina. The intensity of BRP is indicated. Dotted lines indicate the area of lamina vacuoles. Scale bar: 30 µm. (FIG. 6B) Quantification of the vacuole number, size, and BRP intensity. A total of 3 laminae of each group were quantified. Data are presented as mean±s.d. Statistical analysis was performed using Two-Way ANOVA followed by post-hoc Tukey's multiple comparison test. *P<0.05, P<0.01, **P<0.0001.

FIG. 9. An exemplary complete AAV vector DNA sequence including the SORD coding sequence (pAAV-SORD) (SEQ ID NO: 1).

FIG. 10. SORD primer sequences and thermocycling conditions. PCR: polymerase chain reaction; Fw: forward; Rv: reverse.

FIG. 11. Clinical features of patients with hereditary neuropathy and carrying biallelic mutations in SORD.

FIG. 12. Clinical features of patients affected by hereditary neuropathy and carrying the biallelic mutations in SORD. Categorical data are expressed as N (%) if data is available in all individuals or N/number individuals considered (%). Continuous variables are expressed as mean±standard deviation (min-max). CMT, Charcot-Marie-Tooth, dHMN, distal hereditary motor neuropathy.

FIGS. 14A-14C. Exemplary vector design for SORD gene replacement therapy. (FIG. 14A) AAV-9 packaged vector design for a SORD gene replacement therapy. CB7 promotors have been shown to be effective in driving high expression, followed by the SORD cDNA (NCBI Reference Sequence: NM_003104.6), a Posttranscriptional Regulatory Element (WPRE) to further enhance expression and target specificity, and the transcription termination poly(A) element. Further origin of replication (pUC-ori) and ITR sequences (inverted terminal repeat). (FIG. 14B) SORD cDNA sequence. (FIG. 14C) SORD polypeptide sequence.

FIGS. 15A-15D. Significant knock-down of aldose reductase (AR) (AKR1B1 gene) via an antisense oligonucleotide (ASO) (AR 1A, (SEQ ID NO: 22)). Targeting ASO (AR 1A) sequence and ASO-S scrambled sequence (AR-S 1A, (SEQ ID NO: 47)) are shown in FIG. 15A. FIG. 15B shows the modifications to the nucleotide backbone of the ASOs. This was carried out in a SORD patient fibroblast and control fibroblasts and normalized to β-tubulin and measured via Western blot (FIGS. 15C-15D). A further control is a scrambled version of the ASO-S (AR-S 1A) exhibiting random nucleotides was used (FIG. 15C).

FIG. 16. A table of antisense oligonucleotide sequences and target sites in *Homo sapiens* aldo-keto reductase family 1 member B (AKR1B1), exon targets only. Filter criteria: A) 40%<=GC %<=60%; B) Antisense oligo binding energy <=−8 kcal/mol; C) No GGGG in the target sequence.

FIG. 17. A table of antisense oligonucleotide (ASO) sequences an target sites in *Homo sapiens* aldo-keto reductase family 1 member B (AKR1B1), exon targets only. Filter criteria: A) 40%<=GC %<=60%; B) No GGGG in the target sequence; C) Average unpaired probability for target site nucleotides >=0.5; D) For each peak in the accessibility profile that is above the threshold probability of 0.5, all sites targeted to this same peak are ranked by their average unpaired probability (the higher the better) and at most n sites are selected for each peak, where n is determined by max([width of peak/site length], 2); E) Among sites satisfying criteria A-D, the top 20 unique ones with the highest average unpaired probability are listed.

FIG. 18. A table of antisense oligonucleotide (ASO) sequences and target sites in *Homo sapiens* aldo-keto reductase family 1 member B (AKR1B1), hg19_dna range=chr7:134127102-134143944 (intronic targets only). Filter criteria: A) 40%<=GC %<=60%; B) No GGGG in the target sequence; C) Average unpaired probability for target site nucleotides >=0.5; D) For each peak in the accessibility profile that is above the threshold probability of 0.5, all sites targeted to this same peak are ranked by their average unpaired probability (the higher the better) and at most n sites are selected for each peak, where n is determined by max([width of peak/site length], 2); E) Among sites satisfying criteria A-D, the top 20 unique ones with the highest average unpaired probability are listed.

DETAILED DESCRIPTION

Figure 1A:
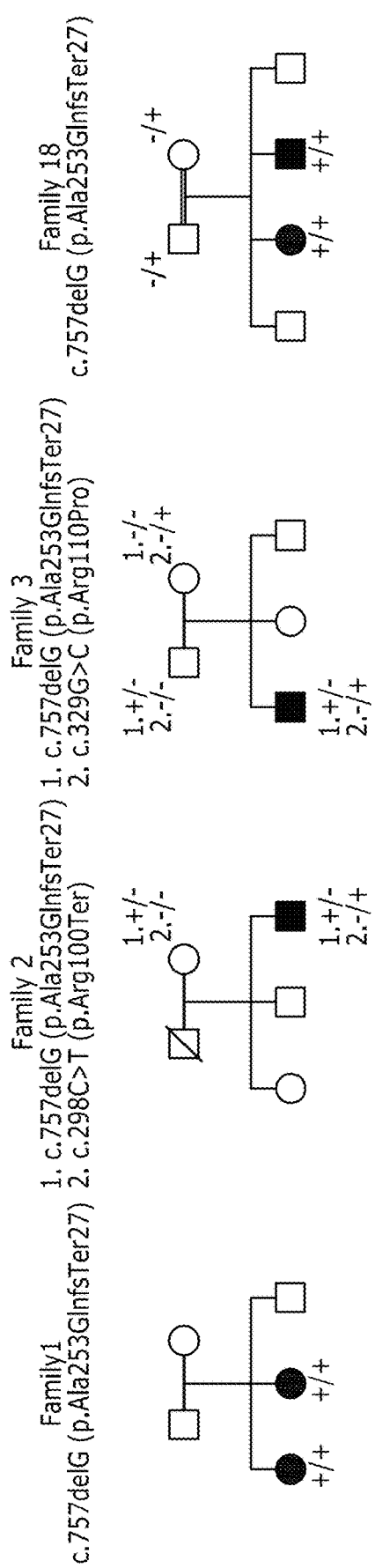
FIGS. 1A-F. SORD gene and pedigrees. Biallelic mutation in SORD cause autosomal recessive dHMN/CMT2.
Figure 1B:
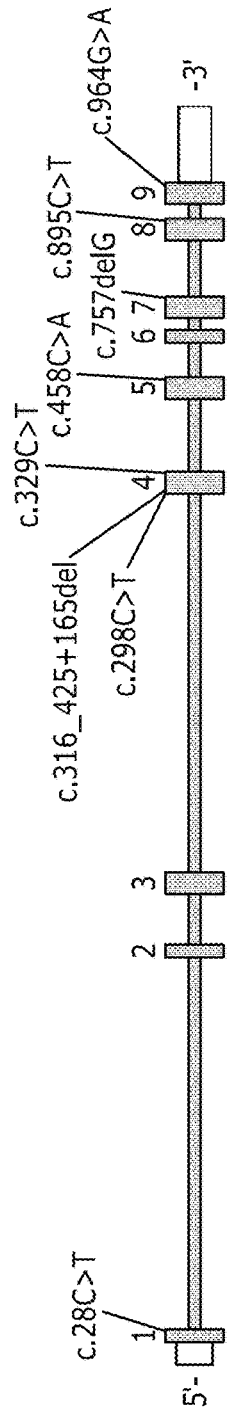
Figures 1C, 1D:
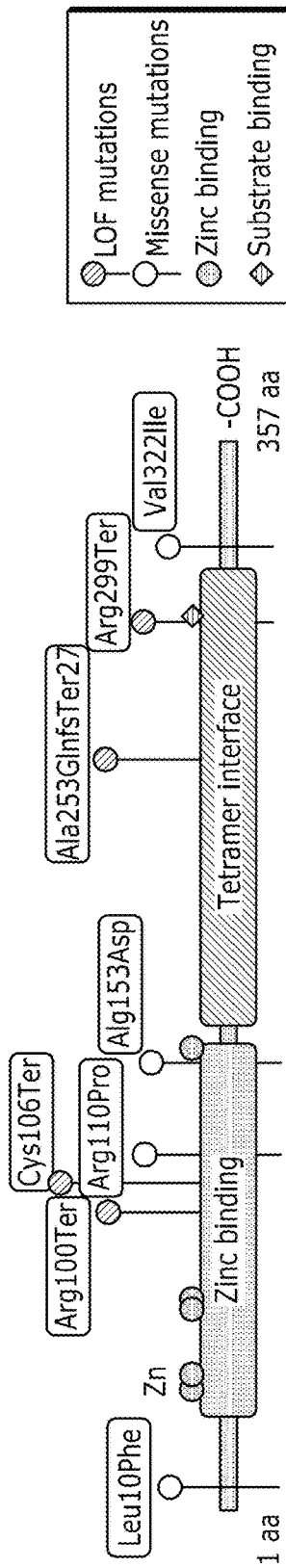

The disclosure provides a method of detecting and/or treating inherited neuropathy and related inherited conditions.

Inherited (or hereditary) neuropathies include, but are not limited to Charcot-Marie-Tooth disease (CMT), hereditary motor and sensory neuropathy, hereditary motor neuropathy, distal hereditary motor neuropathy (dHMN), axonal neuropathies, intermediate neuropathies, and amyotrophic lateral sclerosis type ALS4.

In various aspects, the disclosure provides a method wherein the presence of a mutation in the sorbitol dehydrogenase (SORD) gene is detected in a sample from a subject. The mutation may be detected by examining the DNA sequence of the gene, examining RNA, or examining proteins with mutations that result in some loss of function.

Disclosed herein is the identification of biallelic mutations in the Sorbitol dehydrogenase gene (SORD) associated with the most frequent recessive form of CMT. SORD encodes sorbitol dehydrogenase, an enzyme which converts sorbitol to fructose. It belongs to the two-step polyol pathway previously identified as pivotal to nerve damage in hyperglycemic condition of diabetes. Forty-two cases of CMT across different ethnicities were identified as carrying a nonsense mutation in SORD, c.757delG; p.Ala253GlnfsTer27, either in homozygous or compound heterozygous state. By screening the p.Ala253GlnfsTer27 change in additional cases and multiple control sets, this variant was established as one of the most common pathogenic alleles in men inherited according to Mendel's law (MAF=0.003). Patient fibroblast cultures exhibit a complete loss of SORD protein as well as loss of intracellular sorbitol accumulation, which causes tissue damage. Loss of Sodh1 in *Drosophila* led to synaptic degeneration and progressive motor impairment. Notably, reduction of polyol influx by treatment with aldose reductase inhibitors fully rescued intracellular sorbitol levels in patient fibroblasts and a Sodh1 *Drosophila* model. In the latter model, the treatment also completely ameliorated motor and eye phenotypes. Together, these findings demonstrate a major role of the polyol pathway and sorbitol accumulation in hereditary neuropathies and establish the molecular cause for a potentially treatable condition in a significant fraction of cases. These findings also represent an example of converging pathomechanisms of hereditary and acquired neuropathies with a broader impact in the field of diabetes.

Thus, in various aspects of the disclosure, the method comprises detecting the SORD gene mutation 753delG; p.(Ala253GlnfsTer27), c.757delG; p.Ala253GlnfsTer27, c.28C>T; p.Leu10Phe, c.316_425+165del; p.Cys106Ter, c.329G>C; p.Arg110Pro, c.298C>T; p.Arg100Ter, c.295C>T; p.Arg299Ter, c.964G>A; p.Val322Ile, c.458C>A; p.Ala153Asp; a deletion of individual or multiple coding exons or the entire SORD gene via a copy number variation; or any protein truncating mutation and/or mutation that leads to a "loss of function" or a hypomorphic function of the protein.

In various aspects, the SORD mutation is detected using DNA sequencing methods such as whole exome sequencing, whole genome sequencing (WGS) and/or next-generation sequencing (NGS), allele specific oligonucleotides, polymerase chain reaction (PCR), quantitative or real-time PCR (qPCR), multiplex PCR, nested PCR, Amplification Refractory Mutation System (ARMS) PCR, Multiplex ligation-dependent probe amplification (MLPA), Denaturing gradient gel electrophoresis (DGGE), Single-Strand Conformation Polymorphism (SSCP), Protein Truncation Test (PTT), RFLP, DNA microarray, RNA-seq, using CRISPR-based mutation detection (e.g., CRISPR-Chip, Hajian et al., *Nature Biomedical Engineering* 3, 427-437 (2019)) or other DNA or RNA mutation detection methods suitable for mutation detection.

In various aspects, the SORD mutation is detected by examining proteins using western blotting (immunoblot), High-performance liquid chromatography (HPLC), Liquid chromatography-mass spectrometry (LC/MS), antibody dependent methods such as enzyme-linked immunosorbent assay (ELISA), protein immunoprecipitation, protein immunostaining, protein chip methods or other protein detection methods suitable for mutation detection.

Optionally, the method further comprises measuring sorbitol levels in a sample of the subject. Methods of measuring sorbitol include, e.g., enzymatic assays, fluorimetric assays, chromatography-based methods, and spectroscopy-based methods. An exemplary method of sorbitol measurement is provided in the Examples.

The disclosure further provides a method of characterizing a neuropathy (e.g., inherited neuropathy) and related conditions involving a SORD mutation. In various aspects, the method comprises measuring sorbitol levels in a biological sample of a subject suffering from a neuropathy. In various aspects, the method comprises detecting increased levels of sorbitol in the biological sample. By "increased levels of sorbitol" is meant, e.g., sorbitol levels above about 10 mg/L. SORD-related neuropathy leads to high levels of sorbitol in patients, as described in the Examples and FIG. 13. As such, detection of sorbitol levels above about 10 mg/L indicates that the neuropathy is an inherited neuropathy associated with a SORD mutation, thereby allowing a clinician to characterize the neuropathy afflicting the subject. Optionally, the method comprises a treatment step comprising administering to the subject an agent selected from the group consisting of an aldose reductase inhibitor; an aldose reductase antisense oligonucleotide; a polynucleotide that encodes a SORD peptide; a SORD peptide; an agent that blocks expression of a mutant SORD gene; and an agent that corrects the mutation in SORD gene.

In various aspects, the disclosure provides a method comprising identifying a mutation in the sorbitol dehydrogenase (SORD) gene in a sample from a subject before or after a step of measuring sorbitol levels in the subject. In this regard, the method may be used to confirm a diagnosis of inherited neuropathy. Similarly, the disclosure provides a method for identifying a SORD mutation that is pathogenic, the method comprising measuring sorbitol levels in a subject comprising a mutation in the SORD gene. The presence of increased sorbitol levels (e.g., greater than about 10 mg/L) indicates that the SORD mutation is pathogenic.

Alternatively (or in addition), the method may be used to evaluate the efficacy of a treatment for an inherited neuropathy in a subject. In this regard, the method comprises administering a therapy to the subject, then measuring sorbitol levels in a biological sample. A decrease in sorbitol levels compared to the level of sorbitol observed pretreatment (e.g., a reduction of sorbitol levels below about 10 g/L) indicates an improvement in the subject's condition. The materials and methods described herein may also characterize patient compliance in taking medication for treatment of SORD-related inherited neuropathies or monitor the success of candidate therapeutics in clinical trials.

The sample may be any biological sample taken from the subject, including, but not limited to, any tissue, cell, or fluid (e.g., blood, plasma, serum, or urine) which can be analyzed for a trait of interest, such as the presence or amount of a nucleic acid (e.g., SORD mRNA), a protein (e.g., SORD protein), or sorbitol. In various embodiments, the biological sample is a plasma, serum, saliva, urine, or skin sample.

A "subject" as referred to herein, can be any mammal, such as humans. Animals of agricultural importance, such as bovine, equine, and porcine animals, are contemplated, as well as animals important as domestic pets, including canines and felines; animals important in research, including rodents and primates; and large endangered species and zoo animals such as primates, felines, giraffes, elephants, rhinos.

In various aspects, the method comprises treating the subject by administering to the subject a composition that comprises one or more aldose reductase inhibitors. In some embodiments, the aldose reductase inhibitor is Alrestatin, Epalrestat, Diepalrestat, Fidarestat, Imirestat, Lidorestat, Minalrestat, Ponalrestat, Ranirestat, Salfredin $B_{11}$, Sorbinil, Tolrestat, Zenarestat, or Zopolrestat. Aldose reductase inhibitors are reviewed in *Expert Opin Ther Pat.* 2019; 29(3):199-213; Chatzopoulou et al., *Expert Opin Ther Pat.* 2012; 22(11):1303-23 (incorporated by reference in their entirety).

In some embodiments, enzyme replacement therapy is employed, and a SORD peptide is administered to the subject. As such, the therapy supplements SORD peptide levels where endogenous SORD levels are inadequate or absent. An exemplary SORD peptide is provided in SEQ ID NO: 46. The disclosure contemplates use of a peptide that comprises at least 80%, at least 85%, at least 90%, at least 95%, or 100% identity to SEQ ID NO: 46.

In various embodiments, the method comprises administering to the subject a polynucleotide (e.g., an aldose reductase antisense oligonucleotide, a polynucleotide that encodes the SORD peptide/protein, an agent that blocks expression of a mutant SORD gene, and/or an agent that corrects the mutation in SORD gene). Polynucleotides are typically delivered to a host cell via an expression vector, which includes the regulatory sequences necessary for delivery and expression, although use of expression vectors are not required in the context of the disclosure. In some aspects, the constructs described herein include a promoter (e.g., cytomegalovirus (CMV) promoter or CB7 promoter), a protein coding region (optionally with non-coding (e.g. 3'-UTR) regions that facilitate expression), transcription termination sequences, and/or regulator elements sequences (e.g., Posttranscriptional Regulatory Element (WPRE), poly (A) element, origin of replication (pUC-ori) and/or ITR sequences (inverted terminal repeat)). In various aspects, the constructs described herein include one or more of vector features listed in Table 1. Vector features are also reviewed in Powell et al., *Discov Med.* 2015; 19(102): 49-57 (incorporated by reference in its entirety). For example, the Cre-loxP system may be utilized to express a peptide of interest (e.g., a SORD peptides, optionally in a specific tissue of interest). Expression vectors may be viral-based (e.g., retrovirus-, adenovirus-, or adeno-associated virus-based) or non-viral vectors (e.g., plasmids). Non-vector based methods (e.g., using naked DNA, DNA complexes, etc.) also may be employed. Optionally, the vector is a viral vector, such as a lentiviral vector or baculoviral vector, and in various preferred embodiments the vector is an adeno-associated viral vector (AAV). The expression vector may be based on any AAV serotype, including AAV-1, AAV-2, AAV-3, AAV-4, AAV-5, AAV-6, AAV-7, AAV-8, AAV-9, AAV-10, AAV-11, AAV-12, or AAV-13. Polynucleotides also may be delivered via liposomes, nanoparticles, exosomes, microvesicles, hydrodynamic-based gene delivery, or via a "gene-gun."

Figure 8:
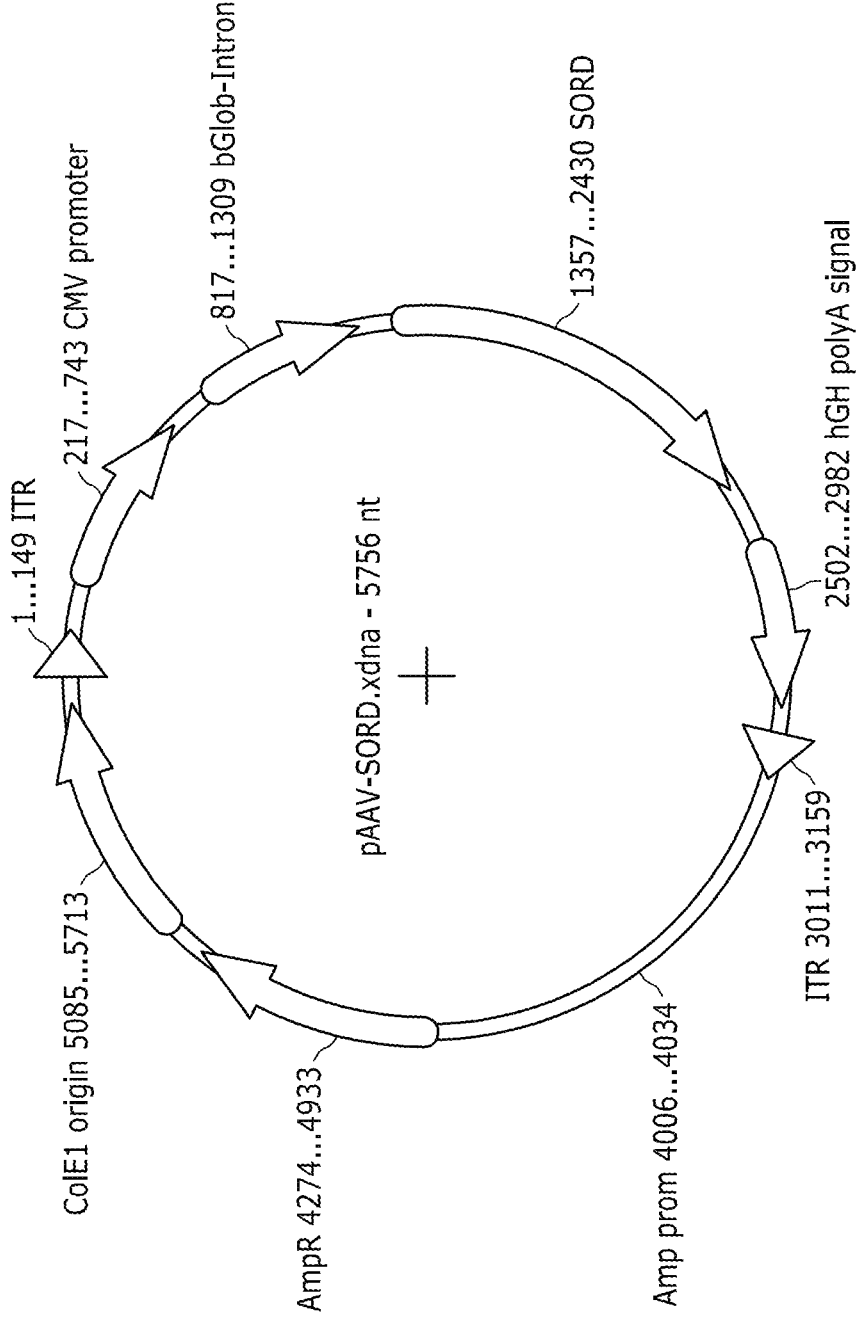
FIG. 8. An illustration of an exemplary expression vector encoding the SORD peptide (pAAV-SORD).

In various embodiments, a polynucleotide that encodes a SORD peptide is administered to the subject. The amino acid sequence of SORD is provided as SEQ ID NO: 46 (FIG. 14C, NCBI Reference Sequence: NP_003095.2). The polynucleotide used in the method optionally encodes the amino acid sequence of SEQ ID NO: 46 or a sequence that is at least 80%, at least 85%, at least 90%, at least 95%, or 100% identical to the amino acid sequence of SEQ ID NO: 46 (which retains the function of SORD). Optionally, the polynucleotide comprises SEQ ID NO: 45 (FIG. 14B) or a sequence that is at least 80%, at least 85%, at least 90%, at least 95%, or 100% identical to the polynucleotide sequence of SEQ ID NO: 45 (and which encodes SORD). Exemplary expression vectors comprising a polynucleotide encoding the SORD peptide are illustrated in FIGS. 8 and 14A. The polynucleotide, in at least one aspect of the disclosure, comprises the nucleic acid sequence shown in FIG. 9 (SEQ ID NO: 1), which corresponds to the sequence of an AAV vector comprising a polynucleotide encoding SORD.

In various embodiments, the method comprises administering to the subject an agent that blocks expression of a mutant SORD gene. An agent that blocks expression of a mutant SORD gene refers to an agent that interferes with expression of a SORD gene so that SORD gene expression and/or SORD protein levels are reduced compared to basal/wild-type levels. It will be appreciated that "blocking" expression of a mutant SORD gene does not require 100% abolition of expression and SORD production; any level of reduced expression of aberrant SORD may be beneficial to a subject. Exemplary agents include, but are not limited to, antisense oligonucleotides (ASO), short hairpin RNA (shRNA), small interfering RNA (siRNA), or micro RNA (miRNA).

In various embodiments, the method comprises administering to the subject an aldose reductase antisense oligonucleotide which targets the aldose reductase sequence such that expression of the enzyme is blocked. An aldose reductase, aldo-keto reductase family 1 member B (AKR1B1), is encoded by SEQ ID NO: 48 (NCBI Reference Sequence: NM_001628). An aldose reductase antisense oli-

TABLE 1

Vector feature elements

| Ubiquitous Promoters | Neuronal specific promoter | Introns (enhanced expression) | Post-transcriptional regulatory elements | Polyadenylation signal enhancers | Bacterial resistance |
|---|---|---|---|---|---|
| CMV, Cba, CAG, CBh, EF1-α, PGK, UBC | NFL, NFH, synapsin, CaMKII, Hb9, MeCP2 | b-Glob, MVM, I.IX, adenovirus SD/ immuno-globulin SA, SV40 late SD/SA | HPRE, WPRE | hGH, bGHpA, SPA, SV40 late | Ampicillin Kanamycin |

Titers of AAV to be administered in methods of the disclosure will vary depending, for example, on the particular AAV, the mode of administration, the treatment goal, the individual, and the cell type(s) being targeted, and may be determined by methods known in the art. Titers of AAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg).

gonucleotide interferes with expression of an aldose reductase gene (AKR1B1), so that AKR1B1 gene expression and/or aldose reductase protein levels are reduced compared to basal/wild-type levels. It will be appreciated that "blocking" expression of an aldose reductase gene (the AKR1B1 gene) does not require 100% abolition of expression and aldose reductase production; any level of reduced expression of aldose reductase may be beneficial to a subject. For example, in various aspects, the aldose reductase antisense oligonucleotide that reduces the expression of aldose reductase. An ASO is a single-stranded deoxyribonucleotide, which is complementary to an mRNA target sequence. In various aspects, the aldose reductase antisense oligonucleotide targets an exonic or intronic sequence of the aldose reductase gene.

Figure 15D:
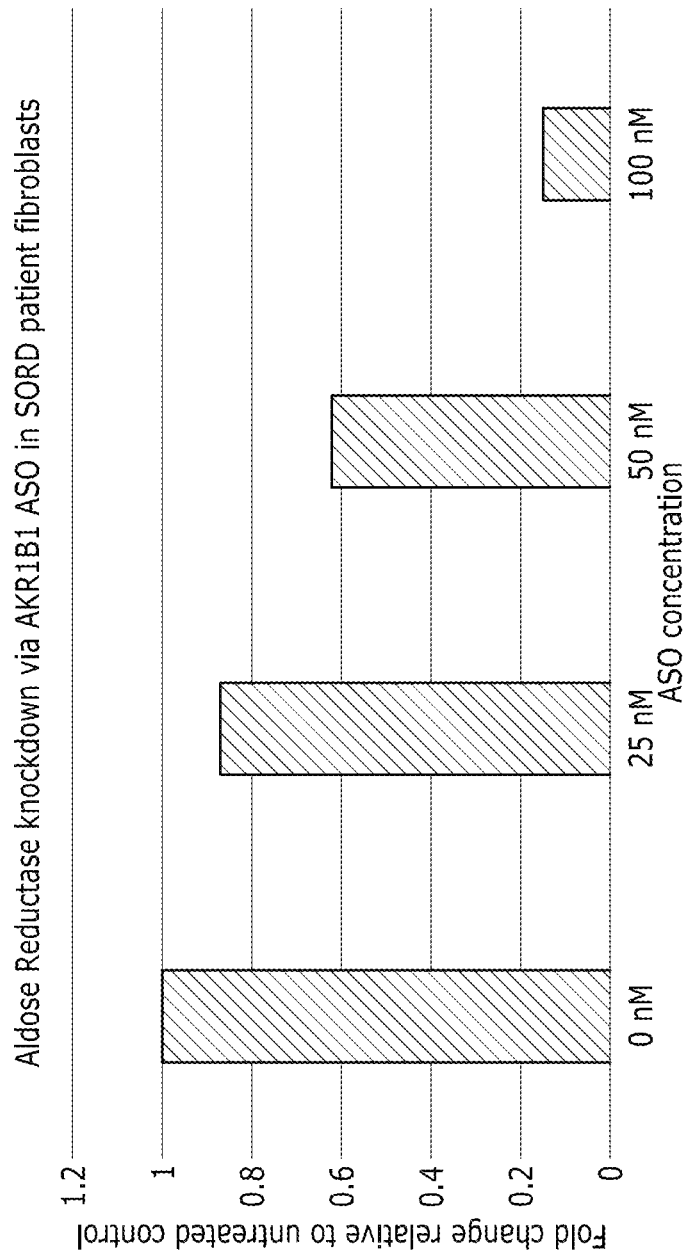

In an exemplary method for identifying ASO sequences targeting aldose reductase, the following criteria were used: A) sequences targeting aldose reductase (AKR1B1) were selected which contained <=40% GC or <=60% GC content; B) sequences containing GGGG nucleotides were excluded; C) sequences with an average unpaired probability for target site nucleotides >=0.5 were selected; D) for each peak in the accessibility profile that was above the threshold probability of 0.5, all sites targeted to the same peak were ranked by their average unpaired probability (the higher the better) and at most n sites are selected for each peak, where n is determined by max width of peak/site length. Exemplary agents satisfying these criteria are provided in Table 2. Additional exemplary ASO sequences and filter criteria are shown in FIGS. 16-18.

an ASO sequence is shown in FIGS. 15A-15B. Modifications to ASO sequences are reviewed in Scoles et al., *Neurol Genet.* 2019; 5(2):e323. (incorporated by reference in its entirety).

In various aspects, the method employs RNA interference (RNAi) to regulate expression of SORD. The RNAi pathway is summarized in Duan (Ed.), Section 7.3 of Chapter 7 in Muscle Gene Therapy, Springer Science+Business Media, LLC (2010). Suitable agents include, e.g., siRNA, miRNA, and shRNA. A shRNA/Hairpin Vector is an artificial RNA molecule (nucleotide) with a tight hairpin turn that can be used to silence target gene expression via RNAi. shRNA is an advantageous mediator of RNAi in that it has a relatively low rate of degradation and turnover, but it often requires use of an expression vector. In exemplary aspects, the disclosure includes the production and administration of an AAV vector expressing one or more shRNAs targeting SORD. The expression of shRNAs is regulated by the use of various promoters. In various aspects, polymerase II promoters, such as U6 and H1, and polymerase III promoters

TABLE 2

ASO sequences targeting AKR1B1/ aldose reductase.

| Starting target position | Ending target position | Target Seq (5'-3') | SEQ ID NO | antisense oligo (5'-3') | SEQ ID NO | GC content | Average unpaired probability | Binding site disruption |
|---|---|---|---|---|---|---|---|---|
| 475 | | AGGUGGAGAUGAUCUUAAAC | 21 | GTTTAAGATCATCTCCACCT | 22 | 40.00% | 0.594 | 12.5 |
| 476 | 495 | GGUGGAGAUGAUCUUAAACA | 23 | TGTTTAAGATCATCTCCACC | 24 | 40.00% | 0.592 | 12.6 |
| 484 | 503 | UGAUCUUAAACAAACCUGGC | 25 | GCCAGGTTTGTTTAAGATCA | 26 | 40.00% | 0.66 | 12.5 |
| 490 | 509 | UAAACAAACCUGGCUUGAAG | 27 | CTTCAAGCCAGGTTTGTTTA | 28 | 40.00% | 0.633 | 9.2 |
| 534 | 555 | CAGGUGGAGAUGAUCUUAAACA | 29 | TGTTTAAGATCATCTCCACCTG | 30 | 40.90% | 0.584 | 12.6 |
| 545 | 566 | GAUCUUAAACAAACCUGGCUUG | 31 | CAAGCCAGGTTTGTTTAAGATC | 32 | 40.90% | 0.611 | 10.3 |
| 548 | 569 | CUUAAACAAACCUGGCUUGAAG | 33 | CTTCAAGCCAGGTTTGTTTAAG | 34 | 40.90% | 0.646 | 9.5 |
| 567 | 588 | AAGUAUAAGCCUGCAGUUAACC | 35 | GGTTAACTGCAGGCTTATACTT | 36 | 40.90% | 0.584 | 7.7 |
| 739 | 760 | UCAAGGCGAUCGCAGCCAAGCA | 37 | TGCTTGGCTGCGATCGCCTTGA | 38 | 59.10% | 0.669 | 10 |
| 741 | 762 | AAGGCGAUCGCAGCCAAGCACA | 39 | TGTGCTTGGCTGCGATCGCCTT | 40 | 59.10% | 0.694 | 9.3 |
| 1025 | 1046 | ACCUGUGUUUCUUGCCUCAUUU | 41 | AAATGAGGCAAGAAACACAGGT | 42 | 40.90% | 0.641 | 5.5 |

In various embodiments, the nucleotide backbone of ASO sequences are modified to a chimeric or gapmer design to reduce gene expression when compared to basal/wild-type levels. In various embodiments, a gapmer design requires a designation of 3-5 nucleotides on each end of the antisense oligonucleotide sequence to harbor modifications in the ribose sugar moiety resistant to RNase H recognition and other nucleases, while all other nucleotides contain an RNase H compatible modification. RNase H is responsible for cleaving RNA-DNA duplexes such as those formed between aberrant mRNA transcripts and synthetically designed DNA antisense oligonucleotides. In various embodiments, the modification to the ASO sequences includes, but is not limited to Phosphorothioate (PS)—RNase H recognizable, phosphorodiamidate morpholino (PMO)—RNase H resistant, 2'-O-methyl—RNase H resistant, 2'-O-methoxyethyl (MOE)—RNase H resistant, locked Nucleic Acid (LNA)—RNase H resistant, ethylene-bridged nucleic acid (ENA)—RNase H resistant, or (S)-constrained ethyl (cEt)—RNase H resistant. Exemplary modification of are used. In some aspects, U6 shRNAs are used. It will be appreciated that RNAi also may be used to downregulate (i.e., block) expression of aldose reductase (e.g., AKR1B1); as such, the disclosure contemplates sue of siRNA, miRNA, and shRNA which targets aldose reductase intronic or extronic sequences to block the expression of aldose reductase.

Traditional small/short hairpin RNA (shRNA) sequences are usually transcribed inside the cell nucleus from a vector containing a Pol III promoter such as U6. The endogenous U6 promoter normally controls expression of the U6 RNA, a small RNA involved in splicing, and has been well-characterized (Kunkel et al., Nature. 322(6074):73-7 (1986); Kunkel et al., Genes Dev. 2(2):196-204 (1988); Paule et al., Nucleic Acids Res. 28(6):1283-98 (2000)). The disclosure includes both murine and human U6 or H1 promoters. The shRNA containing the sense and antisense sequences from a target gene connected by a loop is transported from the nucleus into the cytoplasm where Dicer processes it into siRNAs.

In some aspects of the disclosure, an agent that corrects the mutation in the SORD gene is employed. An agent that corrects the mutation in SORD gene refers to an agent capable of modifying the SORD coding sequence or a regulatory element and/or non-coding region associated with the SORD gene to achieve a desired change in the sequence. In various aspects, genome editing may be used to replace part or all of the SORD gene sequence or alter SORD protein expression levels. In various embodiments, the agent may comprise components employed in genome-editing techniques, such as designer zinc fingers, transcription activator-like effectors nucleases (TALENs), or CRISPR-Cas (clustered regularly interspaced short palindromic repeats-CRISPR associated) systems. An exemplary agent for use in the method of the disclosure is, DNA encoding Cas9 molecules and/or gRNA molecules. Cas9 and gRNA can be present in a single expression vector or separate expression vectors. Adenoviral delivery of the CRISPR/Cas9 system is described in Holkers et al., *Nature Methods* (2014), 11(10):1051-1057 which is incorporated by reference in its entirety.

Other publications describing the CRISPR systems and Cas9 include the following: Cong et al. *Science* (2013) 339:819-23; Jinek et al., *Elife.* (2013) 2:e00471; Lei et al. *Cell* (2013) 152: 1173-1183; Gilbert et al. *Cell* (2013) 154:442-51; Lei et al. *Elife* (2014) 3:e04766; Perez-Pinela et al. *Nat Methods* (2013) 10: 973-976; Maider et al. *Nature Methods* (2013) 10, 977-979; U.S. Pat. Nos. 8,697,359; 8,771,945; 8,795,965; 8,865,406; 8,871,445; 8,889,356; 8,895,308; 8,906,616; 8,932,814; 8,945,839; 8,993,233; 8,999,641; U.S. Application Publication No. 2014/0068797; and International Patent Publication No. WO 2014/197568, all incorporated by reference in their entirety.

In some embodiments, CRISPR/Cas9 multiplexing may be used to target multiple genomic loci wherein two or more guide RNAs are expressed as described in CRISPR 101:A Desktop Resource (1$^{st}$ Edition), *Addgene*, January 2016 which is incorporated by reference in its entirety.

The terms "treating" or "treatment" refer to reducing or ameliorating inherited neuropathy and/or associated disorders and/or symptoms associated therewith. These terms include reducing or delaying the frequency of occurrence or recurrence of the neuropathy or symptoms associated therewith (i.e., lengthening the period of remission in a patient who had suffered from the disorder), as well as reducing the severity of the disorder or any symptoms associated therewith. It is appreciated that, although not precluded, "treating" or "treatment" of a disorder or condition does not require that the disorder, condition, or symptoms associated therewith be completely eliminated.

A dose of an active agent (e.g., an aldose reductase inhibitor, an aldose reductase antisense oligonucleotide, a polynucleotide that encodes a SORD peptide, a SORD peptide, an agent that blocks expression of a mutant SORD gene, or an agent that corrects the mutation in SORD gene) will depend on factors such as route of administration (e.g., local vs. systemic), patient characteristics (e.g., gender, weight, health, side effects), the nature and extent of the inherited neuropathy or associated disorder, and the particular active agent or combination of active agents selected for administration.

The active agents described herein are provided in a composition (e.g., a pharmaceutically-acceptable composition) which may contain formulation components suitable for administration to a subject, as well as additional therapeutic agents. Suitable methods of administering a physiologically-acceptable composition, such as a pharmaceutical composition comprising an agent described herein, are well known in the art. In various aspects, more than one route can be used to administer one or more of the agents disclosed herein. A particular route can provide a more immediate and more effective reaction than another route. For example, in certain circumstances, it will be desirable to deliver the composition orally; through injection or infusion by intravenous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means; by controlled, delayed, sustained or otherwise modified release systems; by implantation devices; using nanoparticles; or as a conjugate.

It is contemplated the two or more active agents described herein may be administered as part of a therapeutic regimen. Alternatively or in addition, one or more of the active agents may be administered with other therapeutics as part of a therapeutic regimen. The active agent(s) may be administered as a monotherapy or as a combination therapy with other treatments administered simultaneously or metronomically. The term "simultaneous" or "simultaneously" refers to administration of two agents within six hours or less (e.g., within three hours or within one hour each other). In this regard, multiple active (or therapeutic) agents may be administered the same composition or in separate compositions provided within a short period of time (e.g., within 30 minutes). The term "metronomically" means the administration of different agents at different times and at a frequency relative to repeat administration. Active agents need not be administered at the same time or by the same route; preferably, in various embodiments, there is an overlap in the time period during which different active agents are exerting their therapeutic effect. Additional aspects and details of the disclosure will be apparent from the following examples, which are intended to be illustrative rather than limiting.

EXAMPLES

General Methods
Families

All families provided written informed consent to participate in the study. The study protocol was approved by the institutional review board of giving institutions. All patients were clinically evaluated by neurologists.

Whole Exome and Sanger Sequencing

Whole exome sequencing was performed in index individuals from sporadic and recessive CMT and dHMN families. The SureSelect Human A11 Exon 50 MB Kit (Agilent) was used for in-solution enrichment, and the HiSeq 2500 instrument (Illumina) was used to produce about 120 bp paired-end sequence reads. The Burrows-Wheeler aligner, and Freebayers were used to align sequence reads and call variants. Final data were uploaded into GENESIS software for analysis. A filtering approach to search for families sharing the same homozygous variants were applied across all exomes in the database. Sanger sequencing, performed by Eurofins Genomics, confirmed segregation of the SORD variants. Polymerase chain reaction (PCR) was carried out in the Veriti Thermocycler (Applied Biosystem) and Platinum Taq (ThermoFisher) was used to amplify the regions containing the target mutations. The following primers were used to target specifically SORD and not SOR2P (FIG. 10).

Fibroblasts Culture

Fibroblasts were obtained from patients and cultured in Dulbecco's Modified Eagle Medium (ThermoFisher) supplemented with 10% fetal bovine serum (FBS), penicillin and streptomycin (Gibco). Cells were maintained in 5% $CO_2$ at 37° C. in a humidified incubator. Asynchronous cell cultures were grown to approximately 80% confluency and treated with epalrestat (100 μM), ranirestat (10 μM) or DMSO for 72 hours. Media containing the drugs or DMSO were changed every 24 hours.

Western Blot

Fibroblasts were lysed in RIPA buffer (ThermoFisher) containing protease inhibitor (Roche) and sonicated for 5 minutes with the Bioruptor sonication device (Diagenode). Cell lysates were centrifuged at 13,000×g for 10 minutes at 4° C., and the supernatant was collected for protein quantification (Pierce BCA Protein Assay Kit). 30 μg of protein sample was mixed with Bolt LDS Sample Buffer and Sample Reducing Agent (ThermoFisher) and heated at 90° C. for 5 min. Samples were loaded on Bolt 4-12% Bis-Tris Plus mini-gel followed by transfer into a nitrocellulose membrane (Bio-Rad). Membrane was blocked with 5% non-fat milk and incubated with anti-SORD (ab189248, Abcam) antibody for 2 hours, washed with TBS containing 0.01% Tween 20 (Bio-Rad) and incubated with a secondary anti-rabbit antibody (Cell Signaling). Membrane was subsequently incubated with GAPDH primary antibody (Santa Cruz) and secondary anti-mouse antibody (Cell Signaling). Chemoluminescence detection was performed with the SuperSignal West Pico PLUS Chemiluminescent Substrate and imaged with the FluorChem E (ProteinSimple).

Sorbitol Measurement

Fibroblasts were collected and lysed as described in Western blot section in the absence of proteinase inhibitor. Sorbitol determination in human fibroblast lysates was performed in ultra-performance liquid chromatography-tandem mass spectrometry (UPLC-MS/MS) (Waters Acquity UPLC & TQD mass spectrometer—Waters, Milford, MA, USA). Fibroblasts were collected and lysed as described in Western blot section in the absence of proteinase inhibitor. Proteinase inhibitor contains high concentration mannitol, which is a sorbitol enantiomer, and can interfere with UPLC-MS/MS sorbitol determination. Lysate samples underwent protein precipitation with Acetonitrile (1:5), ten-time dilution with Acetonitrile-water (50/50) and clean up on Oasis HLB cartridges (10 mg/1 ml), before injection in UPLC (3 μL). UPLC conditions: column, BEH Amide 1.7 μm (2.1×100 mm) at 88° C., eluent A, Acetonitrile 90%-water 5%-Isopropanol 5%, eluent B, Acetonitrile 80%-water 20%, gradient elution 0 min., 100% A, 3.6 min. 100% B, flow rate, 0.45 ml/min. The retention time of sorbitol was 2.7 min. MS/MS conditions: interface, Electrospray interface in negative ion mode, Multiple Reaction Monitoring acquisition, m/z 180.9→88.9 (CV 24, CE 15).

For fasting sorbitol level testing, blood was collected after overnight fasting (last meal the evening before) in serum separator tubes. Samples were centrifuged at 500 g for 10 min. Serum was separated and frozen within an hour from blood collection. Sorbitol level was tested by UPLC using a method adapted from Li et al. Biochem Biophys Res Commun. 2009 Oct. 2; 387(4):778-83. Conditions were as follows: column, BEH Amide 1.7 μm maintained at 25° C. (instead of 45° C.); eluent A, 10 mM ammonium acetate pH10; eluent B, Acetonitrile. Flow rate, 0.6 ml/min with the 20 same gradient. The retention time of Sorbitol was 6.0 min. MS/MS conditions were the same of fibroblast analysis. Serum samples underwent protein precipitation with cold Methanol (1:5), five time dilution with Acetonitrile-water (50/50) and clean up on Oasis HLB cartridges (10 mg/1 ml), before injection in UPLC (3 μL). Calibration curve was done in serum in sorbitol concentration range 0.1-20 mg/L.

Drosophila Stocks and Genetics

Unless specified, all flies were kept on cornmeal-molasses-yeast medium at 25° C., 65% humidity, with 12 h light/12 h dark cycles. The following fly strains used in this study were obtained from Bloomington Drosophila Stock Center: elav$^{C155}$-GAL4, GMR-GAL4, Sdh2$^{MB01265}$, UAS-Sdh1RNAi, and UAS-Sdh2RNAi.

Drug Feeding

Epalrestat or ranirestat was dissolved in dimethyl sulfoxide (DMSO) to achieve a stock concentration of 10 mg/ml, and then mixed into 10 ml fly food at a final concentration of 80 μg/ml. Equal amount of DMSO was mixed into the fly food as control. The vials were dried at room temperature for 12 h before feeding.

Drosophila Lifespan Assay and Negative Geotaxis Assay

For lifespan assay, 100 newly enclosed female flies of each group were collected and placed in vials of 20 individuals. Flies were transferred into new vials every 2 days and the number of dead flies was counted. Survival data was plotted using Kaplan-Meier plot and compared between groups using log-rank test. For negative geotaxis behavior assay, 10 age-matched female flies were placed in a vial marked with a black line drawn horizontally 8 cm above the bottom. Flies were given 60 min to fully recover from $CO_2$ anesthesia, and were gently tapped onto the bottom and given 10 s to climb. Flies that crossed the 8 cm line were counted. For each vial, this assay was repeated 10 times, and 10 independent vials of each group (a total 100 flies per group) were tested. To minimize observer-expectancy bias, this assay was performed with the examiner masked to the group assignment.

Drosophila Brain Dissection, Immunostaining, and Confocal Microscopy

Brain dissection and staining were carried out as previously described (Brazill et al., J Vis Exp. 2018; (138)). Briefly, fly brains were dissected in phosphate-buffered saline (PBS, pH 7.4), fixed in 4% formaldehyde for 10 min, and washed in PBTX (PBS containing 0.4% v/v Triton X-100) for 3 times (15 mins each). Brains were then incubated with primary mouse anti-BRP antibody (nc82, Developmental Studies Hybridoma Bank) at 1:250 dilution in 0.4% PBTX with 5% normal goat serum at 4° C. overnight with gentle shaking. After that, brains were incubated with Cy3-conjugated anti-mouse secondary antibody (Rockland) and Cy5-conjugated anti-HRP (Jackson ImmunoLab) at 1:250 dilution at 4° C. overnight with gentle shaking, followed by 4',6-diamidino-2-phenylindole (DAPI, 1:300, Invitrogen) staining at room temperature for 10 min. Samples were mounted on glass slides with VECTASHIELD Antifade Mounting Medium (Vector Laboratories Inc.). Fly brain slides were imaged using an Olympus IX81 confocal microscope with 60× oil immersion objective lens with a scan speed of 8.0 μs per pixel and spatial resolution of 1024×1024 pixels. Images were processed and analyzed using FluoView 10-ASW (Olympus).

Additional aspects and details of the disclosure will be apparent from the following examples, which are intended to be illustrative rather than limiting.

Example 1: Identification of DNA Variants in CMT Using GENESIS Analysis

Inherited neuropathies, including Charcot-Marie-Tooth disease (CMT), represent an umbrella concept for clinically and genetically heterogeneous conditions affecting the peripheral nerves. CMT is classified depending on conduction velocity as demyelinating (CMT1) and axonal (CMT2) types. Distal hereditary motor neuropathy (dHMN) represents a form of CMT2 in which the burden of disease falls predominantly or exclusively on motor nerves (Rossor, Tomaselli, and Reilly 2016). As opposed to CMT1, for which over 90% of cases have mutations in known genes, only 20 to 30% of CMT2 and distal HMN patients receive a genetic diagnosis (Fridman et al. 2015). Since up to 70% of CMT2 and dHMN cases are sporadic, it becomes more challenging to identify candidate pathogenic genes from single case whole exome and genomic sequences; therefore, large collective datasets are necessary. Using the data aggregation of over 1,100 CMT whole exome sequencing (WES) and whole genome sequencing (WGS) available at the GENESIS analysis platform provided the largest collection of such high quality data available (Gonzalez et al. 2015). Genes with significant DNA variants present in multiple families were identified, as well as individual alleles overrepresented in CMT cases. When querying a subset of 598 undiagnosed CMT patients for recessive non-sense variants in genes shared by >3 families and with minor allele frequency in the gnomAD control database of <1%, 12 cases were identified from 11 unrelated families carrying a homozygous c.757delG; p.(Ala253GlnfsTer27) mutation in SORD. Four more cases from three unrelated families carried the heterozygous c.757delG; p.(Ala253GlnfsTer27) variant together with a second variant, c.298C>T; p.(Arg100Ter) in family 2 c.329G>C; p.(Arg110Pro) in family 3, and c.458C>A; p.(Ala153Asp) in II-1 and II-2 of family 14 (FIG. 1A-D and FIG. 5). All mutations represented loss-of-function (LOF) alleles except c.329G>C; p.(Arg110Pro). Interestingly, the Arg110Pro change is adjacent to the previously reported Tyr111Phe (corresponding to Tyr110Phe in rat), which was shown to abolish SORD enzymatic activity and destabilize the protein (Hellgren et al. 2007).

Figure 1E:
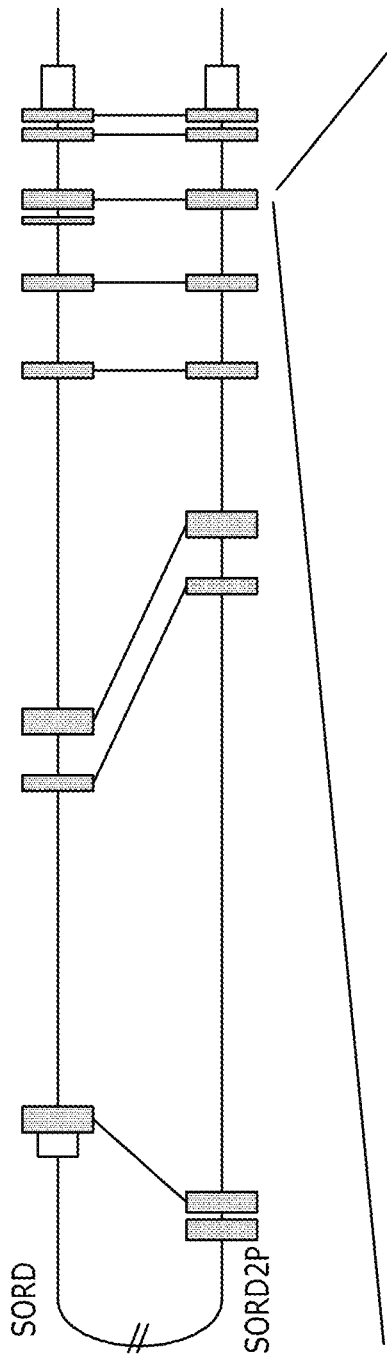
Figure 1F:
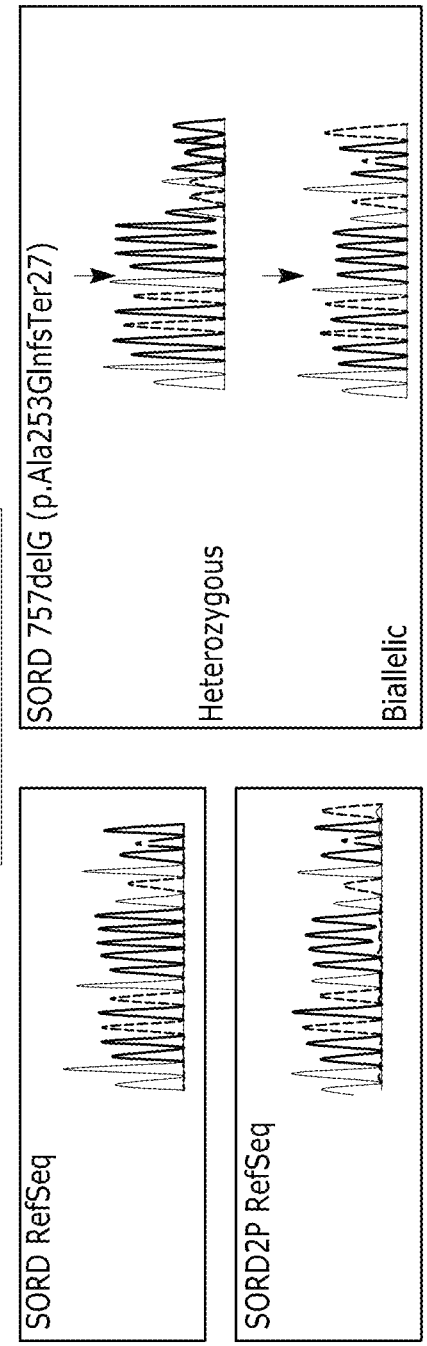
Figure 5:
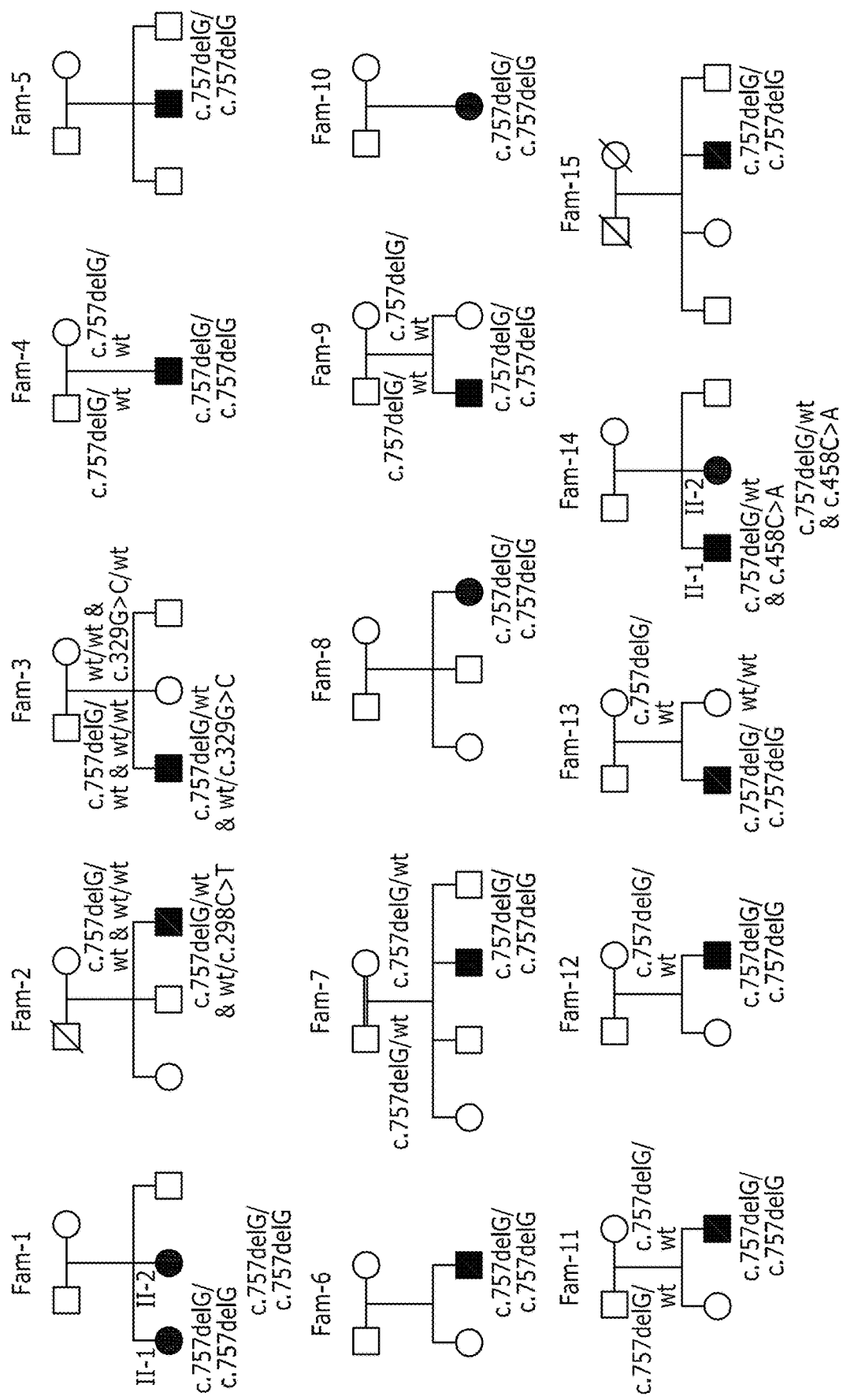
FIG. 5. Pedigrees of families carrying biallelic mutations in SORD. The squares indicate males and the circles females. The diagonal lines are used for deceased individuals. Patients are indicated with filled shapes.

Interestingly, SORD has a non-functional highly homologous paralogue, the pseudogene SORD2P, which is thought to arise from the duplication of SORD within a 0.5 Mb region on chromosome 15 (Carr et al. 2016) (FIG. 1E). In order to specifically amplify SORD, but not SORD2P, in Sanger confirmation studies, primers were designed that took advantage of nucleotide sequence differences and distinct retrotransposon insertions in both genic regions (FIG. 5). Notably, the c.757delG; p.(Ala253GlnfsTer27) mutation in exon 7 of SORD is fixated in the pseudogene SORP2P in over 95% of control chromosomes, along with numerous additional exonic indel mutations, which prevent effective translation of SOPR2P (1000 Genomes Project Consortium et al. 2015; Lek et al. 2016). Because of the high similarity of the regions, a nested PCR approach was necessary to obtain specific amplification of exon 7 of SORD and distinguish it from the homologous region in SORD2P. The presence of the variants detected by WES was confirmed by Sanger sequencing in all cases and segregation data in immediate relative carriers was provided. (FIG. 1F and FIG. 5).

An independent set of 103 unresolved CMT2/dHMN cases WES at the (UCL Institute of Neurology in London (UK)) were screened. Nine cases from six unrelated families were identified carrying the homozygous c.757delG; p.(Ala253GlnfsTer27) mutation in SORD (8.7%). A third independent set of 297 recessive or sporadic CMT2/dHMN patients was screened by targeted Sanger sequencing of exon 7 of SORD, which was extended to the other coding exons if one c.757delG; p.(Ala253GlnfsTer27) was identified, and revealed 20 additional cases (7%) from 18 families with biallelic mutations in SORD: 16 cases with a homozygous c.757delG; p.(Ala253GlnfsTer27) mutation and four cases with c.757delG; p.(Ala253GlnfsTer27) in compound heterozygous state with a second likely pathogenic variant. The latter included c.964G>A; p.(Val322Ile) in family 29, a 275 bp deletion c.316_425+165del in exon 4 in family 30, a de novo c.28C>T; p.(Leu10Phe) in family 32, and c.895C>T; p.(Arg299Ter) in family 33. All changes have a minor allele frequency (MAF) of <0.0001 in gnomAD (Lek et al. 2016). The residues affected by missense mutations are highly conserved across multiple species (FIG. 1D) with GERP scores greater than 3. Further, biallelic non-sense variants in SORD were absent from 4,598 index cases affected by distinct neurological disorders other than CMT present in the GENESIS database.

The allelic carrier frequency of the c.757delG; p.(Ala253GlnfsTer27) variant in the normal population is 0.003% based on an allelic count of 94 out of 30,872 in gnomAD genomes (Lek et al. 2016). Of note, the gnomAD exome set detected the c.757delG; p.(Ala253GlnfsTer27) change at a significantly lower rate at MAF=0.00008, due to failure to pass random forest filters. GENESIS uses the FreeBayes software for variant calling (Gonzalez et al. 2015), which may have resulted in an allele frequency closer to the gnomAD genome based call set ($MAF_{GENESIS}$=0.002, 22 out of 9,196). Sanger sequencing of 600 healthy controls was performed, including 200 samples of European, 100 samples of Turkish and 200 samples of Middle Eastern origin, and identified three heterozygous, but no homozygous, c.757delG; p.(Ala253GlnfsTer27) alleles (MAF=0.0025). These calculations support an estimated prevalence of the homozygous c.757delG; p.(Ala253GlnfsTer27) allele alone of ~1/100,000 individuals, making it the most common individual pathogenic allele in axonal neuropathies and one of the most common alleles for any Mendelian disease.

Overall 45 individuals affected by hereditary neuropathy from 38 unrelated families were identified in the present study to carry biallelic mutations in SORD (FIGS. 11 and 12). Of note, 71% of cases were sporadic with no evidence of family history or consanguinity. The formal clinical diagnosis was axonal CMT in 51% (n=16), distal HMN in 40% (n=18), and intermediate CMT in 9% (n=4) of cases The mean age of onset of the neuropathy was 17±8 years and walking difficulties was the most common complain at onset. Delayed motoric development milestones were uncommon, but two thirds of the patients reported foot deformities, indicating that the neuropathy probably started earlier in life. At first examination all individuals had limb weakness, but only half showed sensory impairment. Weakness was mild in distal upper limbs and ranged from mild to near complete paralysis in the distal lower limbs. Proximal muscles of the upper and lower limbs were typically unaffected. Seven patients had upper limb tremor, four had mild scoliosis and two had mild hearing loss. One case had a concurrent and likely unrelated syndromic disorder encompassing dysmorphic features, non-progressive mental retardation since the age of three years, and spastic ataxia with evidence of cerebellar atrophy at brain MRI. None of the patients had cataract nor involvement of other organs. According to the CMT neuropathy score, the neuropathy was mild in 67% (n=30), moderate in 31% (n=14) and severe in one case. 42% of patients (n=19) needed ankle-foot orthosis to sustain feet during walking, one patient required unilateral support and one patient was wheelchair dependent. Detailed nerve conduction studies were available in 42 patients and invariably showed a motor axonal neuropathy, with intermediate reduction of conduction velocities in 26% (n=11) and decreased sensory action potentials in 26% (n=65).

Figure 13:
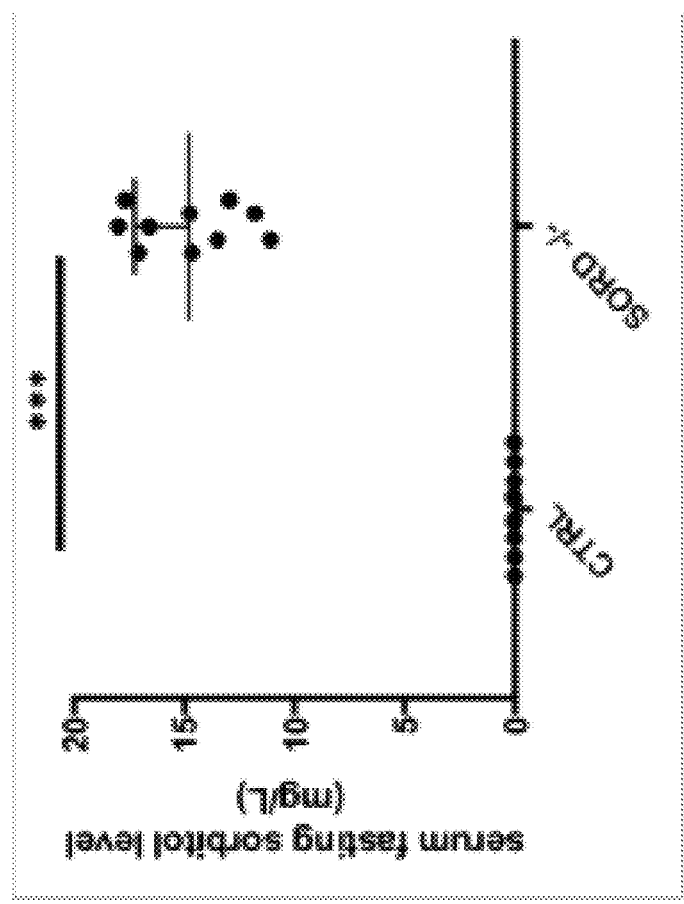
FIG. 13. Fasting sorbitol level in serum from ten unrelated healthy controls and ten patients carrying biallelic p.Ala253GlnfsTer27 mutations in SORD. The graphs show the mean±s.d. and data distribution (dots), and the p-value of two-tailed t-tests comparing SORD protein and sorbitol levels across groups—*p<0.05, p<0.01, and *p<0.001. All experiments were twice repeated independently.

Example 2: Assessing SORD Protein Expression in Human Fibroblasts and SORD Levels in Blood Sorbitol dehydrogenase is a homotetrameric enzyme of 38-kDa subunits, which is widely distributed in mammalian tissues (Johansson et al. 2001; Hellgren et al. 2007; Lindstad, Teigen, and Skjeldal 2013). It represents the second enzyme of the two-step polyol pathway, in which glucose is converted to sorbitol, a relatively non-metabolizable sugar, by the enzyme aldose reductase (AR). Sorbitol is then oxidized to fructose by SORD (FIG. 2A). To gather further insights into the functional consequences of recessive mutations in SORD, next SORD expression was assessed in fibroblasts from five unrelated affected individuals with homozygous c.757delG; p.(Ala253GlnfsTer27) (n=4) or c.757delG; p.(Ala253GlnfsTer27) & c.895C>T; p.(Arg299Ter) (n=1) variants as well as two unaffected carriers of c.757delG; p.(Ala253GlnfsTer27) in heterozygous state. SORD protein was absent in all patients and the wild-type levels were reduced in unaffected carriers compared to controls (FIG. 2B). Accordingly, intracellular sorbitol concentrations were over 10 times higher in patients' fibroblasts compared to controls, in keeping with a loss of SORD enzymatic activity (FIG. 2C). Fasting sorbitol levels in serum from ten patients carrying the homozygous p.Ala253GlnfsTer27 mutation and ten unrelated controls and found it was over 100 times higher (14.82±0.780 vs 0.046±0.004 mg/L, p<0.0001) was determined, confirming the lack of SORD enzymatic activity in patients (FIG. 13). This study also demonstrates that sorbitol is a useful marker for detecting or characterizing inherited neuropathy associated with SORD mutation in a mammalian subject.

Example 3: Investigating the SORD Mutation in Models of SORD Deficiency

To further explore the pathophysiology of SORD mutation in vivo, *Drosophila melanogaster* models of SORD deficiency were established. *Drosophila* has two functional SORD genes (Sodh1 and Sodh2) that share 90% residue identity (Luque et al. 1998). SORD is conserved across distant phyla and *Drosophila* Sodh1 (NP_001287203.1) and Sodh2 (NCBI Reference Sequence: NP_524311.1) encoded proteins share 75% and 73% identity with human SORD protein (NCBI Reference Sequence: NP_003095.2 (SEQ ID NO: 46)), respectively. A mutant allele of Sodh2 was obtained where the gene is disrupted by a transposon Minos mediated integration cassette (MiMIC) insertion (Sodh2$^{MB01265}$) (Bellen et al. 2011). Homozygous Sodh2 (Sodh2$^{MB01265/MB01265}$) mutants are viable with normal life span. To characterize neurodegenerative phenotypes, the *Drosophila* visual system was used to take advantage of the highly organized parallel axons of the compound eye that allow in vivo detection of subtle neuronal and synaptic pathological changes (Bausenwein, Dittrich, and Fischbach 1992). Axons of the outer photoreceptor axons traverse the lamina cortex and make synaptic connections with lamina monopolar neurons in the lamina layer (FIG. 3A). In the control flies (yw) at 2 days after eclosion (DAE), the organized lamina cartridges of photoreceptor synapses can be visualized in the xy- and xz-planes, respectively (FIG. 3B). A loss of photoreceptor terminals in the lamina layer of Sodh2$^{MB01265/MB01265}$ mutants was observed at 2 days after eclosion (DAE) (FIG. 3C). The phenotype became progressively severe at 10 DAE, with vacuoles being more numerous and larger in size distributed across the synaptic lamina layer (FIG. 3C, D). These vacuoles exhibited a loss of neuronal membrane (marked by HRP labelling), as well as a reduced Bruchpilot (BRP, a synaptic active zone cytomatrix protein) labelling, indicating synaptic degeneration (FIG. 3C, D). To validate the findings described herein, a second SORD model was generated by specific knockdown of both Sodh1 and Sodh2 expression in neurons using a pan-neuronal driver elav$^{C155}$. Loss of both Sodh1 and Sodh2 resulted in age-dependent synapse degeneration, similar to that of homozygous Sodh2 (Sodh2$^{MB01265/MB01265}$) (FIG. 6). The behavioral phenotypes of SORD deficiency the Sodh2$^{MB01265/MB01265}$ homozygous flies with a systemic loss of function in Sodh2 were characterized and although these flies exhibited a normal life-span, their locomotor activity was significantly compromised at a late-stage (40 DAE) (FIG. 3E, F). This indicated a progressive, age-dependent neuromuscular dysfunction reminiscent of hereditary neuropathies. Moreover, the sorbitol levels were measured in fly heads at 10 DAE and observed a significant increase in the Sodh2$^{MB01265/MB01265}$ model (FIG. 4B), consistent with the observation in patient fibroblasts. Taken together, *Drosophila* models of SORD deficiency were successfully established that recapitulate typical pathological phenotypes in human patients, including (1) a normal lifespan, (2) progressive and age-dependent synaptic degeneration and locomotor deficiency, and (3) increased sorbitol levels.

Figure 4A:
FIGS. 4A-G. Treatment with aldose reductase inhibitors Epalrestat and Ranirestat decrease sorbitol level and restore function.
Figure 4B:
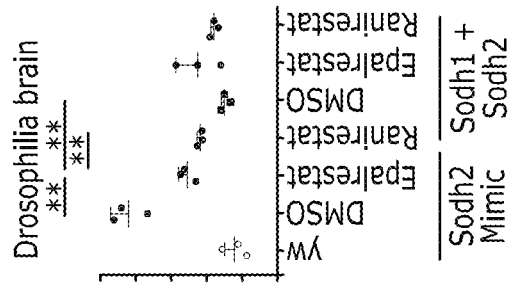
Figure 4C:
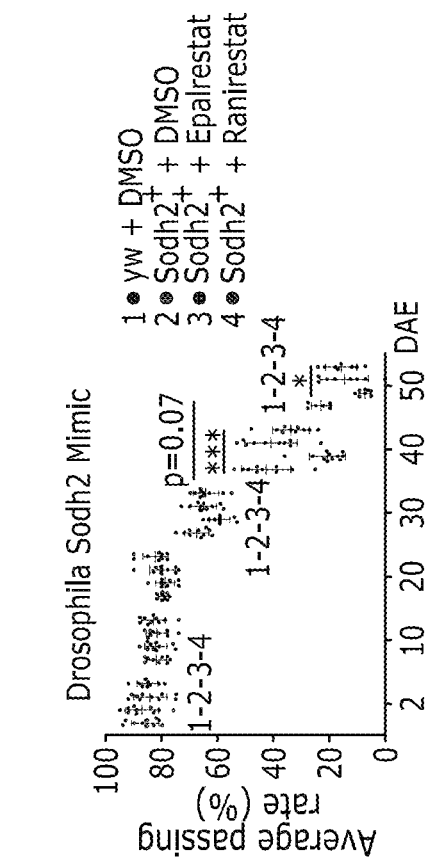
Figure 4D:
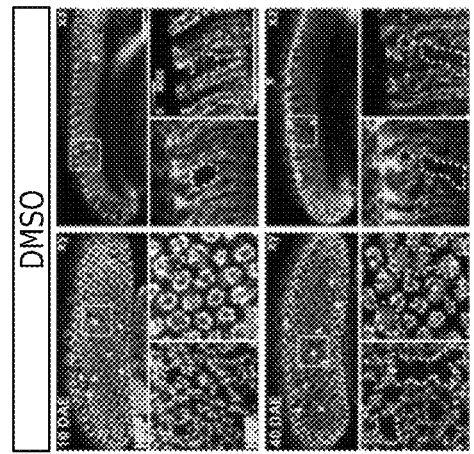
Figure 4G:
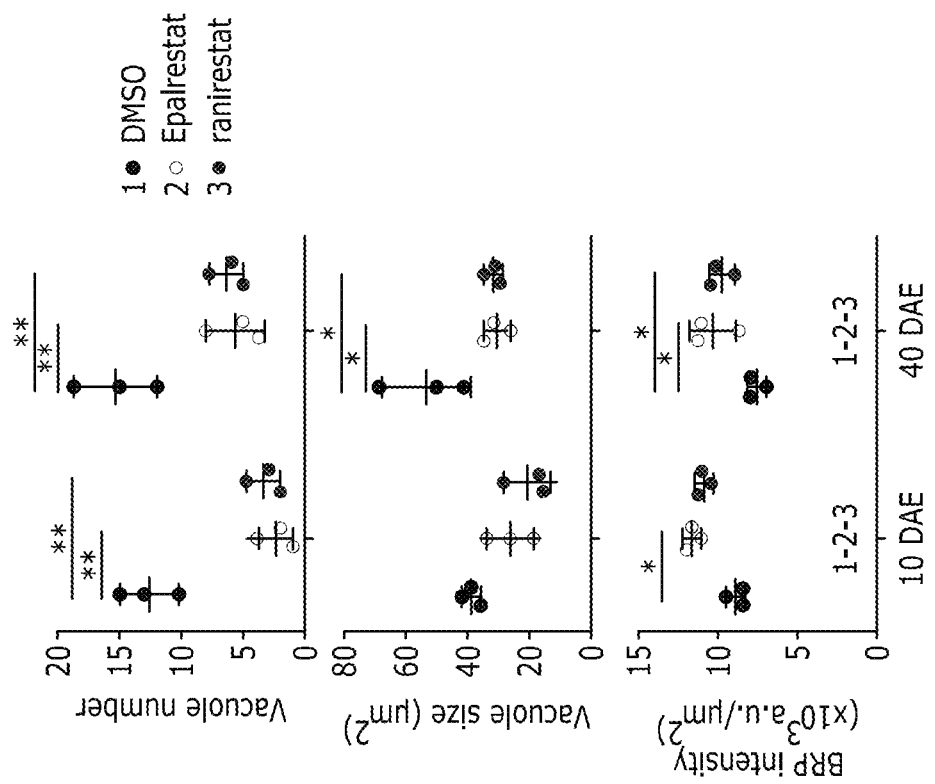
Figure 4E:
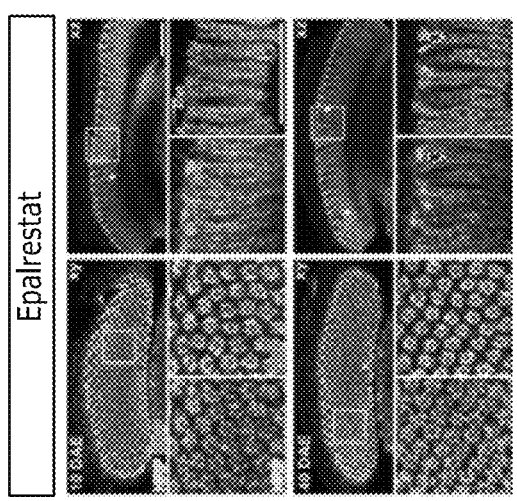
Figure 4F:
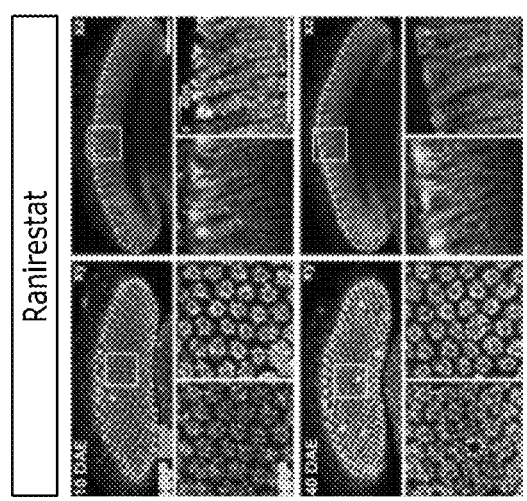
Figure 7:
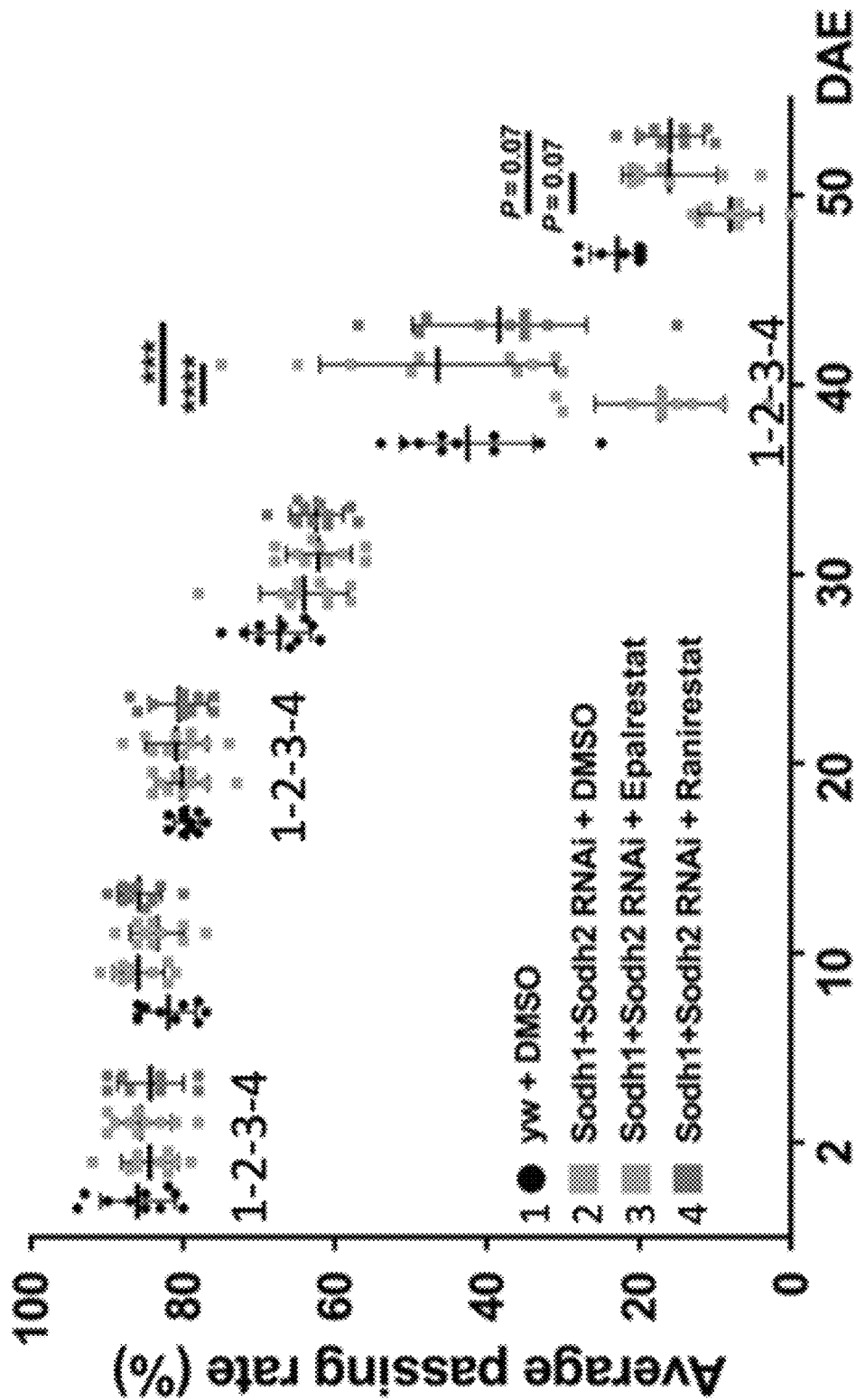
FIG. 7. Treatment with aldose reductase inhibitors Epalrestat and Ranirestat restore locomotor function in Sodh1 and Sodh2 double knockdown flies. Locomotor activity of control flies (yw) feeding with DMSO (dots, first data point from the left for each DAE point indicated), or flies with neuronal specific knockdown of Sodh1 and Sodh2 feeding with DMSO (squares, second data point from the left for each DAE point indicated), 80 µM Epalrestat (squares, third data point from the left for each DAE point indicated), or 80 µM Ranirestat (squares, forth data point from the left for each DAE point indicated). n=10 in each group. Data are presented as mean±s.d. Statistical analysis was performed using Two-Way ANOVA followed by post-hoc Tukey's multiple comparison test. *P<0.001, **P<0.0001.

After establishing loss-of-function as the mechanism of action and a known enzymatic pathway, treatment options for SORD associated hereditary neuropathy were investigated. It had previously been shown that the pharmacological inhibition of aldose reductase, the enzyme upstream of SORD, represents a successful strategy to reduce toxic sorbitol accumulation in cellular and animal model of diabetes (Kikkawa et al. 1983; Matsumoto et al. 2008; Ramirez and Borja 2008; Hao et al. 2015; Grewal et al. 2016) and, arguably, also humans (Chalk, Benstead, and Moore 2007; Polydefkis et al. 2015; Sekiguchi et al. 2019). The effect of two commercially available aldose reductase inhibitors (ARI), Epalrestat and Ranirestat, were tested on intracellular sorbitol accumulation in patient fibroblasts lacking functional SORD. Patient and control fibroblasts were grown for 72 hrs in the presence or absence of Epalrestat (100 µM) or Ranirestat (10 µM) and intracellular sorbitol levels were measured thereafter. Both ARI, Epalrestat and Ranirestat, achieved a significant reduction of sorbitol to a level comparable to controls (FIG. 4A). Further, *Drosophila* models of SORD were fed with Epalrestat and Ranirestat starting at 2 DAE. A significant reduction of sorbitol level was observed in the Sodh2$^{MB01265/MB01265}$ fly heads at 10 DAE (FIG. 4B). Importantly, the locomotor activities of Sodh2$^{MB01265/MB01265}$ flies and flies with neuronal specific knockdown of both Sodh1 and Sodh2 were rescued to the levels of yw control flies (FIG. 4C, FIG. 7). Furthermore, Epalrestat or Ranirestat feeding restored the age-dependent synaptic defects in Sodh2$^{MB01265/MB01265}$ mutant flies. In DMSO vehicle treated flies, the loss of synaptic termini was highly prominent in the advanced age of 40 DAE where the expansion of neighboring vacuoles resulted in fused, much larger vacuoles encompassing multiple synaptic cartridges (FIG. 4D). Remarkably, epalrestat/ranirestat feeding reduced the number of vacuoles and restored the localization of synaptic cytomatrix protein BRP at both 10 and 40 DAE (FIG. 4E-G).

In summary, SORD represents a novel recessive gene causing axonal/intermediate, motor predominant CMT. Genetic data from the cohort as well as from control databases suggest that the predominant pathogenic variant in SORD, c.757delG; p.(Ala253GlnfsTer27), with a carrier frequency in of ~3/1,000 individuals in the population, may represent one of the most common specific alleles causing a recessive Mendelian disease. Indeed, with a frequency in undiagnosed CMT2 and dHMN cases of up to ~10%, it will likely account for a significant portion of the diagnostic gap in inherited axonal neuropathies. It is intriguing that, despite their frequency, mutations in SORD were not identified as a cause of CMT by previous studies. The presence of the human SORD2P gene duplication may have hampered the detection of variants in the functional SORD, since available annotation programs are highly dependent on the unique mapping of 150-300 bp long reads generated by current next-generation sequencing technologies. Other known pathogenic variants have previously been shown to be concealed by the presence of pseudogenes (De Vos et al. 2004). The pathogenicity of SORD mutations is further supported by in vitro data in patient-derived fibroblasts, which showed absent SORD protein and intracellular sorbitol accumulation. Two in vivo Drosophila models recapitulated the human phenotype with progressive synaptic degeneration and motor impairment, SORD deficiency, and in increased sorbitol levels.

The studies described herein demonstrate that enzymatic loss-of-function and subsequent sorbitol accumulation is a mechanism of action for SORD associated CMT. Previous studies in cellular and animal models of diabetes have shown that an increased polyol influx with intracellular sorbitol accumulation is paralleled by an increase in cellular osmolarity, oxidative stress and decreased NADPH levels, which can all have a detrimental effects on peripheral nerves (Schmidt et al. 2001; Obrosova 2005; Sango et al. 2006). However, previous studies on adult C57BL/LiA mice expressing reduced level of SORD protein due to an intronic splicing mutation did not identify overt neurological defects (Holmes, Duley, and Hilgers 1982; Lee, Chung, and Chung 1995; Ng et al. 1998). Based on patient clinical data and the late-onset phenotype in flies, it will be important to extend the observation to aging C57BL/LiA mice or create complete knock-out SORD mouse or rat models. The study further unravels a central role of the polyol pathway in peripheral nerve metabolism and survival in normoglycemic conditions. Although the mechanism by which intracellular sorbitol accumulation can lead to selective degeneration of peripheral nerves is yet unknown, the observation of increased sorbitol levels in patient derived cells in this study has promising implications, both as a biomarker of the disease and as a target of future therapeutic interventions, including methods for substrate reduction, gene replacement or correction, and SORD enzyme substitution. Accordingly, disclosed herein are preclinical studies demonstrating the beneficial effects of substrate reduction via ARI application in human derived cells and Drosophila models. Epalrestat is currently marketed in few countries for the treatment of diabetic complications (Grewal et al. 2016) while Ranirestat has been advanced into late stages of clinical trials (Polydefkis et al. 2015; Sekiguchi et al. 2019).

REFERENCES

Auton, et al. 1000 Genomes Project Consortium, 2015. "A Global Reference for Human Genetic Variation." Nature 526 (7571): 68-74.

Bausenwein, et al. 1992. "The Optic Lobe of Drosophila melanogaster. II. Sorting of Retinotopic Pathways in the Medulla." Cell and Tissue Research 267 (1): 17-28.

Bellen, et al. 2011. "The Drosophila Gene Disruption Project: Progress Using Transposons with Distinctive Site Specificities." Genetics 188 (3): 731-43.

Brazill, et al. 2018. "Quantitative Cell Biology of Neurodegeneration in Drosophila Through Unbiased Analysis of Fluorescently Tagged Proteins Using ImageJ." Journal of Visualized Experiments: JoVE, no. 138 (03).

Callaghan, et al. 2012. "Diabetic Neuropathy: Clinical Manifestations and Current Treatments." The Lancet. Neurology 11 (6): 521-34.

Carr, et al. 2016. "A Study of the Neuropathy Associated with Transthyretin Amyloidosis (ATTR) in the UK." Journal of Neurology, Neurosurgery, and Psychiatry 87 (6): 620-27.

Chalk, et al. 2007. "Aldose Reductase Inhibitors for the Treatment of Diabetic Polyneuropathy." The Cochrane Database of Systematic Reviews, no. 4 (October): CD004572.

De Vos, et al. 2004. "Novel PMS2 Pseudogenes Can Conceal Recessive Mutations Causing a Distinctive Childhood Cancer Syndrome." American Journal of Human Genetics 74 (5): 954-64.

Dyck, et al. 1993. "The Prevalence by Staged Severity of Various Types of Diabetic Neuropathy, Retinopathy, and Nephropathy in a Population-Based Cohort: The Rochester Diabetic Neuropathy Study." Neurology 43 (4): 817-24.

Fridman, et al. 2015. "CMT Subtypes and Disease Burden in Patients Enrolled in the Inherited Neuropathies Consortium Natural History Study: A Cross-Sectional Analysis." Journal of Neurology, Neurosurgery, and Psychiatry 86 (8): 873-78.

Gonzalez, et al. 2015. "Innovative Genomic Collaboration Using the GENESIS (GEM.App) Platform." Human Mutation 36 (10): 950-56.

Grewal, et al. 2016. "Updates on Aldose Reductase Inhibitors for Management of Diabetic Complications and Non-Diabetic Diseases." Mini Reviews in Medicinal Chemistry 16 (2): 120-62.

Hao, et al. 2015. "Hyperglycemia Promotes Schwann Cell De-Differentiation and De-Myelination via Sorbitol Accumulation and Igf1 Protein Down-Regulation." The Journal of Biological Chemistry 290 (28): 17106-15.

Hellgren, et al. 2007. "A Hydrogen-Bonding Network in Mammalian Sorbitol Dehydrogenase Stabilizes the Tetrameric State and Is Essential for the Catalytic Power." Cellular and Molecular Life Sciences: CMLS 64 (23): 3129-38.

Holmes, et al. 1982. "Sorbitol Dehydrogenase Genetics in the Mouse: A 'null' Mutant in a 'European' C57BL Strain." Animal Blood Groups and Biochemical Genetics 13 (4): 263-72.

Johansson, et al. 2001. "Crystal Structure of Sorbitol Dehydrogenase." Chemico-Biological Interactions 130-132 (1-3): 351-58.

Kikkawa, et al. 1983. "Effect of a New Aldose Reductase Inhibitor, (E)-3-Carboxymethyl-5-[(2E)-Methyl-3-Phenyl-propenylidene]Rhodanine (ONO-2235) on Peripheral Nerve Disorders in Streptozotocin-Diabetic Rats." Diabetologia 24 (4): 290-92.

Lee, et al. 1995. "Demonstration That Polyol Accumulation Is Responsible for Diabetic Cataract by the Use of Transgenic Mice Expressing the Aldose Reductase Gene in the Lens." Proceedings of the National Academy of Sciences of the United States of America 92 (7): 2780-84.

Lek, et al. 2016. "Analysis of Protein-Coding Genetic Variation in 60,706 Humans." Nature 536 (7616): 285-91.

Lindstad, et al. 2013. "Inhibition of Sorbitol Dehydrogenase by Nucleosides and Nucleotides." Biochemical and Biophysical Research Communications 435 (2): 202-8.

Luque, et al. 1998. "Sorbitol Dehydrogenase of *Drosophila*. Gene, Protein, and Expression Data Show a Two-Gene System." The Journal of Biological Chemistry 273 (51): 34293-301.

Matsumoto, et al. 2008. "Long-Term Treatment with Ranirestat (AS-3201), a Potent Aldose Reductase Inhibitor, Suppresses Diabetic Neuropathy and Cataract Formation in Rats." Journal of Pharmacological Sciences 107 (3): 340-48.

Ng, et al. 1998. "Effects of Sorbitol Dehydrogenase Deficiency on Nerve Conduction in Experimental Diabetic Mice." Diabetes 47 (6): 961-66.

Obrosova I. 2005. "Increased Sorbitol Pathway Activity Generates Oxidative Stress in Tissue Sites for Diabetic Complications." Antioxidants & Redox Signaling 7 (11-12): 1543-52.

Polydefkis, et al. 2015. "Safety and Efficacy of Ranirestat in Patients with Mild-to-Moderate Diabetic Sensorimotor Polyneuropathy." Journal of the Peripheral Nervous System: JPNS 20 (4): 363-71.

Ramirez, et al. 2008. "Epalrestat: An Aldose Reductase Inhibitor for the Treatment of Diabetic Neuropathy." Pharmacotherapy 28 (5): 646-55.

Rossor, et al. 2016. "Recent Advances in the Genetic Neuropathies." Current Opinion in Neurology 29 (5): 537-48.

Sango, et al. 2006. "High Glucose-Induced Activation of the Polyol Pathway and Changes of Gene Expression Profiles in Immortalized Adult Mouse Schwann Cells IMS32." Journal of Neurochemistry 98 (2): 446-58.

Schmidt, et al. 2001. "Inhibition of Sorbitol Dehydrogenase Exacerbates Autonomic Neuropathy in Rats with Streptozotocin-Induced Diabetes." Journal of Neuropathology and Experimental Neurology 60 (12): 1153-69.

Sekiguchi, et al. 2019. "Aldose Reductase Inhibitor Ranirestat Significantly Improves Nerve Conduction Velocity in Diabetic Polyneuropathy: A Randomized Double-Blind Placebo-Controlled Study in Japan." Journal of Diabetes Investigation 10 (2): 466-74.

What is claimed:

1. A method for treating inherited neuropathy associated with a mutation in the sorbitol dehydrogenase (SORD) gene in a mammalian subject, comprising administering to the subject an effective amount of an inhibitor of aldose reductase.

2. The method of claim 1, wherein the inhibitor of aldose reductase is selected from the group consisting of Alrestatin, Epalrestat, Diepalrestat, Fidarestat, Imirestat, Lidorestat, Minalrestat, Ponalrestat, Ranirestat, Salfredin B11, Sorbinil, Tolrestat, Zenarestat, and Zopolrestat.

3. The method of claim 1, wherein the inhibitor of aldose reductase is Epalrestat.

4. The method of claim 1, wherein the inhibitor of aldose reductase is Zopolrestat.

5. The method of claim 1, wherein the inhibitor of aldose reductase is Ranirestat.

6. The method of claim 1, wherein the mutation in the sorbitol dehydrogenase (SORD) gene is selected from the group consisting of c.329G>C; p.Arg110Pro, c.298C>T; p.Arg100Ter, and c.458C>A; p. Ala 153 Asp, wherein the mutations are defined with reference to the nucleotide sequence of SEQ ID NO: 45 and the amino acid sequence of SEQ ID NO: 46.

7. The method of claim 1, wherein the mutation in the sorbitol dehydrogenase (SORD) gene selected from the group consisting of c.28C>T; p.Leu10Phe, c.316_425+165del; p.Cys106Ter, c.895C>T; p.Arg299Ter, and c.964G>A; p. Val322Ile, wherein the mutations are defined with reference to the nucleotide sequence of SEQ ID NO: 45 and the amino acid sequence of SEQ ID NO: 46.

8. The method of claim 1, wherein the effective amount of an aldose reductase inhibitor reduces the level of intracellular sorbitol in the subject.

9. The method of claim 1, further comprising detecting the mutation in the sorbitol dehydrogenase gene of the subject.

10. The method of claim 1, further comprising measuring the level of sorbitol in a subject, wherein a sorbitol level of greater than about 10 mg/L in blood indicates that the subject has neuropathy associated with the mutation in the sorbitol dehydrogenase (SORD) gene.

11. The method of claim 1, wherein the subject has a deletion of individual or multiple coding exons that encode the amino acid of SEQ ID NO:46 or a deletion of the entire SORD gene that encodes the amino acid of SEQ ID NO:46.

12. The method of claim 1, wherein the mutation in the SORD gene leads to hypomorphic function of SORD.

13. The method of claim 1, wherein the mutation in the SORD gene leads to loss of function of SORD.

14. The method of claim 1, wherein the mutation in the sorbitol dehydrogenase (SORD) gene is c.757delG; p.Ala253GlnfsTer27, wherein the mutation is defined with reference to the nucleotide sequence of SEQ ID NO: 45 and the amino acid sequence of SEQ ID NO: 46.

* * * * *